(12) United States Patent
Poyser

(10) Patent No.: US 7,001,904 B1
(45) Date of Patent: Feb. 21, 2006

(54) GUANIDINE DERIVATIVES QUINAZOLINE AND QUINOLINE FOR USE IN THE TREATMENT OF AUTOIMMUNE DISEASES

(75) Inventor: Jeffrey Philip Poyser, Macclesfield (GB)

(73) Assignee: AstraZeneca AB, (SE)

( * ) Notice: Subject to any disclaimer, the term of this patent is extended or adjusted under 35 U.S.C. 154(b) by 241 days.

(21) Appl. No.: 10/311,587

(22) PCT Filed: Jun. 19, 2001

(86) PCT No.: PCT/GB01/02698

§ 371 (c)(1),
(2), (4) Date: Dec. 18, 2002

(87) PCT Pub. No.: WO02/00644

PCT Pub. Date: Jan. 3, 2002

(30) Foreign Application Priority Data

| | | | |
|---|---|---|---|
| Jun. 24, 2000 | (GB) | .................................. | 0015376 |
| Dec. 19, 2000 | (GB) | .................................. | 0030989 |

(51) Int. Cl.
*C07D 403/12* (2006.01)
*C07D 413/12* (2006.01)
*A61K 31/505* (2006.01)

(52) U.S. Cl. .............................. 514/234.5; 514/266.2; 514/266.22; 514/266.24; 514/266.4; 544/119; 544/293

(58) Field of Classification Search ................ 544/119, 544/293, 234.5, 266.2, 266.22, 266.24, 266.4
See application file for complete search history.

(56) References Cited

U.S. PATENT DOCUMENTS

| | | | |
|---|---|---|---|
| 5,773,459 A | 6/1998 | Tang et al. | |
| 6,806,274 B1 * | 10/2004 | Crawley et al. | ......... 514/266.2 |

FOREIGN PATENT DOCUMENTS

| | | |
|---|---|---|
| WO | 95/15758 A | 6/1995 |
| WO | 97/03069 | 1/1997 |
| WO | 98/38984 | 9/1998 |
| WO | 98/50047 | 11/1998 |
| WO | 98/50370 | 11/1998 |
| WO | 98/52558 | 11/1998 |
| WO | 99/09024 | 2/1999 |
| WO | 01/04102 A | 1/2001 |

OTHER PUBLICATIONS

Casanova et al., PubMed Abstract (Rev Neurol 28(9):909-15), May 1999.*
Gibson et al., "Epidermal growth factor receptor tyrosine kinase: structure-activity relationships and antitumour activity of novel quinazolines", Bioorganic & Medicinal Chemistry Letters, vol. 7, No. 21, Nov. 4, 1997, pp. 2723-2728, XP004136520, ISSN: 0960-894X.
Hong et al.; "Synthesis and Billogical Activities of Some $N^4$-Substituted 4-Aminopyrazolo 3,4-$d$-pyrimidines"; Journal of Medicinal Chemistry, 1976, vol. 19, No. 4, pp. 555-558.
Myers et al.; "The Preparation and SAR of 4-(Anilino), 4-(Phenoxy), and 4-Thiophenoxy)-Quinazolines: Inhibitors of $p56^{lck}$ and EGF-R Tyrosine Kinase Activity"; Bioorganic & Medicinal Chemistry Letters, 1997, vol. 7, No. 4, pp. 417-420.
van Muijlwijk-Koezen et al.; "Isoquinoline and Quinazoline Urea Analogues as Antagonists for the Human Adenosine $A_3$ Receptor"; J. Med. Chem., 2000, vol. 43, pp. 2227-2238.

* cited by examiner

Primary Examiner—Deepak Rao
(74) Attorney, Agent, or Firm—Morgan Lewis & Bockius LLP

(57) ABSTRACT

The invention concerns quinazoline and quinoline derivatives of Formula (I) wherein $Q^1$ includes a quinazoline or quinoline ring optionally substituted with a group such as halogeno, trifluoromethyl and cyano, or a group of the formula: $Q^3$—$X^1$— wherein $X^1$ includes a direct bond and O and $Q^3$ includes aryl, aryl-(1-6C)alkyl, heterocyclyl and heterocyclyl-(1-6C)alkyl; each of $R^2$, $R^3$ and $R^5$ is hydrogen or (1-6C)alkyl, provides that one of the parts of groups $R^2$ and $R^4$ together, $R^3$ and $R^4$ together and $R^5$ and $R^4$ together forms a bond; $R^6$ is an optionally substituted group selected from (2-6C) alkenyl, (2-6C) alkynyl, (3-7C)cycloalkyl and (3-7C) cycloalkenyl, or $R^6$ is a substituted (1-6C) alkyl group; and $Q^2$ includes aryl and aryl-(1-3C)alkyl or a pharmaceutically-acceptable salt thereof; processes for their preparation, pharmaceutical compositions containing them and their use in the manufacture of a medicament for use in the prevention or treatment of T cell mediated diseases or medical conditions in a warm-blooded animal.

9 Claims, No Drawings

GUANIDINE DERIVATIVES QUINAZOLINE AND QUINOLINE FOR USE IN THE TREATMENT OF AUTOIMMUNE DISEASES

This application is a 371 of PCT/GB01/02698 filed Jun. 19, 2001.

This invention concerns certain novel quinazoline derivatives which possess pharmacological properties of use in the treatment of autoimmune diseases or medical conditions, for example T cell mediated disease such as transplant rejection or rheumatoid arthritis. The invention also concerns processes for the manufacture of the quinazoline derivatives of the invention, pharmaceutical compositions containing them and their use in therapeutic methods, for example by virtue of inhibition of T cell mediated disease.

A critical requirement of the immune system is the ability to differentiate between "self" and "non-self" (i.e. foreign) antigens. This discrimination is required to enable the immune system to mount a response to foreign proteins such as those on the surface of pathogens whilst maintaining tolerance to endogenous proteins and thereby preventing damage to normal tissues. An autoimmune disease results when self-tolerance breaks down and the immune system reacts against tissues such as the joints in rheumatoid arthritis or nerve fibres in multiple sclerosis. Stimulation of the human immune response is dependent on the recognition of protein antigens by T cells. However T cells do not become activated by and respond to antigen alone but are only triggered into action when the antigen is complexed with major histocompatibility complex (MHC) molecules on the surface of an antigen-presenting cell such as a B cell, macrophage or dendritic cell. Thus T cell activation requires the docking into the T cell receptor of the peptide/MHC complex expressed on an antigen-presenting cell. This interaction, which confers the antigen specificity to the T cell response, is essential for full activation of T lymphocytes. Subsequent to this docking, some of the earliest signal transduction events leading to full T cell activation are mediated through the action of multiple tyrosine-specific protein kinases (E. Hsi et al., *J. Biol. Chem.*, 1989, 264, 10836) including $p56^{lck}$ and ZAP-70. The tyrosine kinase $p56^{lck}$ is a lymphocyte specific member of the src family of non-receptor protein tyrosine kinases (J. D. Marth et al., *Cell*, 1985, 43, 393). The enzyme is associated with the inner surface of the plasma membrane where it binds to the T cell receptor associated glycoproteins CD4 (in helper T cells) and CD8 (in cytotoxic or killer T cells) (C. E. Rudd et al., *Proc. Natl. Acad. Sci. USA*, 1988, 85, 5190 and M. A. Campbell et al., *EMBO J*, 1990, 9, 2125).

It is believed that $p56^{lck}$ tyrosine kinase plays an essential role in T cell activation as, for example, the loss of $p56^{lck}$ expression in a human Jurkat T cell line prevents the normal T cell response to stimulation of the T cell receptor (D. B. Straus et al., *Cell*, 1992, 70, 585) and a deficiency in $p56^{lck}$ expression causes severe immune deficiency in humans (F. D. Goldman et al., *J. Clin. Invest*, 1988, 102, 421).

Certain autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes are believed to be associated with inappropriate T cell activation (see, for example, J. H. Hanke et al., *Inflamm. Res.*, 1995, 44, 357). In addition the acute rejection of transplanted organs can also be interpreted as a consequence of inappropriate T cell activation. Therefore, compounds which modulate T cell activation by way of inhibition of one or more of the multiple tyrosine-specific protein kinases which are involved in the early signal transduction steps which lead to full T cell activation, for example by way of inhibition of $P56^{lck}$ tyrosine kinase, are expected to provide therapeutic agents for such pathological conditions.

Without wishing to imply that the compounds disclosed in the present invention possess pharmacological activity only by virtue of an effect on a single biological process, it is believed that the compounds modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase.

In particular, the quinazoline derivatives of the invention are expected to be useful as immunoregulation or immunosuppressive agents for the prevention or treatment of organ rejection following transplant surgery.

Agents of this kind would offer therapy for transplant rejection and autoimmune diseases whilst avoiding toxicities associated with the commonly used, less selective immunosuppressants. The leading agent for the prevention or treatment of transplant rejection is cyclosporin A which, although effective, is often associated with side-effects such as renal damage and hypertension which results in kidney failure in a substantial number of patients. It is contemporary practice to treat rheumatoid arthritis initially with symptom relief agents such as NSAIDs, which do not have any beneficial effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

As stated above, the present invention is based, in particular, on the discovery that the quinazoline derivatives of the invention modulate T cell activation by way of inhibition of one or more of the multiple tyrosine-specific protein kinases which are involved in the early signal transduction steps which lead to full T cell activation. Accordingly compounds of the present invention possess higher inhibitory potency against particular non-receptor tyrosine kinases such as $p56^{lck}$ tyrosine than against other non-receptor tyrosine kinases or against receptor tyrosine kinases (RTKs) such as epidermal growth factor (EGF) RTK. In general, the quinazoline derivatives of the invention possess sufficient potency in inhibiting non-receptor tyrosine kinases such as $p56^{lck}$ tyrosine kinase that they may be used in an amount sufficient to inhibit, for example, $p56^{lck}$ tyrosine kinase whilst demonstrating reduced potency, preferably whilst demonstrating no significant activity, against RTKs such as EGF RTK. Thus the quinazoline derivatives of the invention can be used in the clinical management of those particular diseases which are sensitive to inhibition of such non-receptor tyrosine kinases, for example autoimmune diseases or medical conditions, for example T cell mediated disease such as transplant rejection or rheumatoid arthritis.

It is disclosed by K. H. Gibson et al., *Bioorganic & Medicinal Chemistry Letters*, 1997, 7, 2723–2728 that certain 4-anilinoquinazoline derivatives possess useful EGF RTK inhibitory properties. It is also disclosed that 1-(6,7-dimethoxyquinazolin-4-yl)-3-phenylurea is inactive as an EGF RTK inhibitor.

It is disclosed in International Patent Application WO 98/50370 that certain 5-substituted quinazoline derivatives may be useful as inhibitors of serine/threonine protein kinases. Whilst most of the examples are 4-amino-5-phenoxyquinazolines, there is the disclosure of three 4-ureido-5-phenoxyquinazolines, namely of:—

1-[5-(4-methoxyphenoxy)quinazolin-4-yl]-3-phenylurea, 1-[5-(4-methoxyphenoxy)quinazolin-4-yl]-3-(3-bromophenyl)urea and 1-[5-(4-methoxyphenoxy)quinazolin-4-yl]-3-(3-methoxyphenyl)urea.

It is disclosed by C. I. Hong et al., *J. Med. Chem.*, 1976, 19, 555–558 that certain 4-aminopyrazolo[3,4-d]pyrimidine derivatives possess growth inhibitory activity against cultured L1210 leukemia cells. The disclosed compounds include:—

1-phenyl-3-(pyrazolo[3,4-d]pyrimidin-4-yl)urea, 1-(2-chlorophenyl)-3-(pyrazolo[3,4-d]pyrimidin-4-yl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea.

It is disclosed in International Patent Application WO 97/03069 that certain quinoline and quinazoline derivatives may be useful as protein tyrosine kinase inhibitors. All of the disclosed examples are 4-heteroarylaminoquinazoline derivatives and none of them are 1-heteroaryl-3-(quinazolin-4-yl)urea derivatives.

It is disclosed in International Patent Application WO 98/43960 that certain 3-cyanoquinoline derivatives may be useful as protein tyrosine kinase inhibitors. Almost all of the 398 disclosed examples were 3-cyano-4-anilinoquinoline or 3-cyano-4-benzylaminoquinoline derivatives. There is no disclosure of any (3-cyanoquinolin-4-yl)urea derivatives.

It is disclosed in International Patent Application WO 99/09024 that certain 1-phenyl-3-(quinolin-4-yl)urea derivatives may be useful as antagonists of the human HFGAN72 receptor, a G-protein coupled neuropeptide receptor, and hence may be of potential use in the treatment of obesity. There is no disclosure as examples of any 1-phenyl-3-(quinazolin-4-yl)urea or 1-phenyl-3-(3-cyanoquinolin-4-yl)urea compounds.

According to one aspect of the invention there is provided a quinazoline derivative of the Formula I

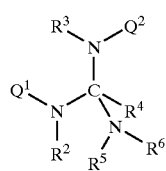

I wherein $Q^1$ is a quinazoline-like ring such as a group of the formula Ia, Ib, Ic or Id

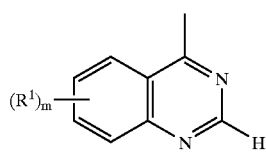

Ia

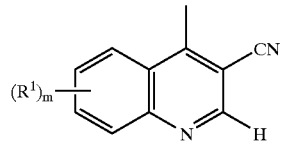

Ib

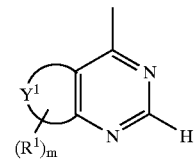

Ic

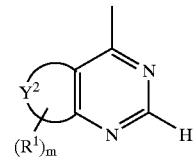

Id wherein:

$Y^1$ together with the carbon atoms to which it is attached forms a 5- or 6-membered aromatic or partially unsaturated ring comprising 1 to 3 heteroatoms selected from O, N and S;

$Y^2$ together with the carbon atoms to which it is attached forms a 5- or 6-membered aromatic or partially unsaturated ring comprising 1 to 3 heteroatoms selected from O, N and S;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1,6C)alkyl-(3-6C)alkenoylamino, (3-6C)alkynoylamino, N-(1-6C)alkyl-3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^3-X^1-$ wherein $X^1$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $OC(R^7)_2$, $SC(R^7)_2$ and $N(R^7)C(R^7)_2$, wherein $R^7$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkenedioxy, and wherein adjacent carbon atoms in any (2-6C)alkylene chain within a $R^1$ substituent are optionally separated by the insertion into the chain of a group selected from O, S, SO, $SO_2$, $N(R^8)$, CO, $CH(OR^8)$, $CON(R^8)$, $N(R^8)CO$, $SO_2N(R^8)$, $N(R^8)SO_2$, $CH=CH$ and $C\equiv C$ wherein $R^8$ is hydrogen or 1-6C)alkyl, and wherein any $CH_2=CH-$ or $HC\equiv C-$ group within a $R^1$ substituent optionally bears at ther terminal $CH_2=$ or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino (1-6C)alkyl or from a group of the formula:

$$Q^4-X^2-$$

wherein $X^2$ is a direct bond or is selected from CO and $N(R^9)CO$, wherein $R^9$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno substituents or a substituent selected from hydroxy, cyano, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6-C)alkyl-(1-6C)alkanesulphonylamino, or from a group of the formula:

$$-X^3-Q^5$$

wherein $X^3$ is a direct bond or is selected from O, S, SO, $SO_2$, $N(R^{10})$, CO, $CH(OR^{10})$, $CON(R^{10})$, $N(R^{10})CO$, $SO_2N(R^{10})$, $N(R^{10})SO_2$, $C(R^{10})_2O$, $C(R^{10})_2S$ and $N(R^{10})C(R^{10})_2$, wherein $R^{10}$ is hydrogen or (1-6C)alkyl, and $Q^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^4-R^{11}$$

wherein $X^4$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl or N,N-di-[(1-6C)akyl]carbamoyl-(1-6C)alkyl, or from a group of the formula:

$$-X^5-Q^6$$

wherein $X^5$ is a direct bond or is selected from O and $N(R^{13})$, wherein $R^{13}$ is hydrogen or (1-6C)alkyl, and $Q^6$ is aryl, aryl-(1-6C)alkyl, heteroaryl, heteroaryl-(1-6C)alkyl, heterocyclyl or heterocyclyl-(1-6C)alkyl, and any $Q^6$ group optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo or thioxo substituents;

$R^2$ is hydrogen or (1-6C)alkyl and $R^3$ is hydrogen or (1-6C)alkyl, or $R^2$ and $R^3$ together form a $CH_2$, $(CH_2)_2$ or $(CH_2)_3$ group, $R^5$ is hydrogen or (1-6C)alkyl, or $R^5$ and $R^6$ together with the N atom to which they are attached form a 4- to 7-membered heterocyclic ring optionally containing a further heteroatom selected from O, N and S, provided that one of the pairs of groups $R^2$ and $R^4$ together, $R^3$ and $R^4$ together and $R^5$ and $R^4$ together forms a bond;

$Q^2$ is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituted with 1, 2, 3, or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^6-R^{14}$$

wherein $X^6$ is a direct bond or is selected from O and $N(R^{15})$, wherein $R^{15}$ is hydrogen or (1-6C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

$$-X^7-Q^7$$

wherein $X^7$ is a direct bond or is selected from O, S, SO, $SO_2$, $N(R^{16})$, CO, $CH(OR^{16})$, $CON(R^{16})$, $N(R^{16})CO$, $SO_2N(R^{16})$, $N(R^{16})SO_2$, $C(R^{16})_2O$, $C(R^{16})_2S$ and $C(R^{16})_2N(R^{16})$, wherein each $R^{16}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl, or $Q^2$ is optionally substituted with a (1-3C)alkylenedioxy group, and wherein any aryl, heteroaryl or heterocyclyl group within a substituent on $Q^2$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]

sulphamoyl, (1-6C)alkanesulphonylamino and N-(1-6C)alkyl-(1-6C)alkanesulphonylamino, or from a group of the formula:

$$-X^8-R^{17}$$

wherein $X^8$ is a direct bond or is selected from O and N($R^{18}$), wherein $R^{18}$ is hydrogen or (1-6C)alkyl, and $R^{17}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within a substituent on $Q^2$ optionally bears 1 or 2 oxo or thioxo substituents; and $R^6$ is an optionally substituted group selected from (2-6C)alkenyl, (2-6C)alkynyl, (3-7C)cycloalkyl and (3-7C)cycloalkenyl, or $R^6$ is a substituted (1-6C)alkyl group, and wherein adjacent carbon atoms in any (2-6C)alkylene chain within a $R^6$ group are optionally separated by the insertion into the chain of a group selected from O, S, SO, $SO_2$, N($R^{19}$), CO, CH(O$R^{19}$), CON($R^{19}$), N($R^{19}$)CO, $SO_2$N($R^{19}$), N($R^{19}$)$SO_2$, CH=CH and C≡C wherein $R^{19}$ is hydrogen or (1-6C)alkyl, and wherein any $CH_2$=CH or HC≡C— group within a $R^6$ group optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^8-X^9-$$

wherein $X^9$ is a direct bond or is selected from CO and N($R^{20}$)CO, wherein $R^{20}$ is hydrogen or (1-6C)alkyl, and $Q^8$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^6$ group optionally bears on each said $CH_2$ or $CH_3$ group one or more of the following substituents, provided that the $R^6$ group when it is (1-6C)alkyl must bear at least one such substituent, one or more halogeno substituents or a substituent selected from hydroxy, cyano, amidino, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, (1-6C)alkoxycarbonylamino, N-(1-6C)alkyl-(1-6C)alkoxycarbonylamino, N-[hydroxy-(2-6C)alkyl]carbamoyl, N-[(1-6C)alkoxy-(2-6C)alkyl]carbamoyl, N-[amino-(2-6C)alkyl]carbamoyl, N-[(1-6C)alkylamino-(2-6C)alkyl]carbamoyl, N-{di -[(1-6C)alkyl]amino-(2-6C)alkyl}carbamoyl, N,N-di-[hydroxy-(2-6C)alkyl]carbamoyl, N,N-di-[(1-6C)alkoxy-(2-6C)alkyl]carbamoyl, N,N-di-[amino-(2-6C)alkyl]carbamoyl, N,N-di-[(1-6C)alkylamino-(2-6C)alkyl]carbamoyl and N,N-di-{di-[(1-6C)alkyl]amino-(2-6C)alkyl}carbamoyl, or from a group of the formula:

$$-X^{10}-Q^9$$

wherein $X^{10}$ is a direct bond or is selected from O, S, SO, $SO_2$, N($R^{21}$), CO, CH(O$R^{21}$), CON($R^{21}$), N($R^{21}$)CO, $SO_2$N($R^{21}$), N($R^{21}$)$SO_2$, C($R^{21}$)$_2$O, C($R^{21}$)$_2$S and N($R^{21}$)C($R^{21}$)$_2$, wherein $R^{21}$ is hydrogen or (1-6C)alkyl, and $Q^9$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a $R^6$ group, or any heterocyclic group formed when $R^5$ and $R^6$ together with the N atom to which they are attached form a ring, optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^{11}-R^{22}$$

wherein $X^{11}$ is a direct bond or is selected from O and N($R^{23}$), wherein $R^{23}$ is hydrogen or (1-6C)alkyl, and $R^{22}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl, or from a group of the formula:

$$-X^{12}-Q^{10}$$

wherein $X^{12}$ is a direct bond or is selected from O and N($R^{24}$), wherein $R^{24}$ is hydrogen or (1-6C)alkyl, and $Q^{10}$ is aryl, aryl-(1-6C)alkyl, heteroaryl, heteroaryl-(1-6C)alkyl, heterocyclyl or heterocyclyl-(1-6C)alkyl, and any $Q^{10}$ group optionally bears 1 or 2 substituents, which may be the same or different, selected from halogeno, (1-6C)alkyl and (1-6C)alkoxy, and wherein any heterocyclyl group within a $R^6$ group, or the heterocyclic group formed when $R^5$ and $R^6$ together with the N atom to which they are attached form a ring, optionally bears 1 or 2 oxo or thioxo substituents;

or a tautomer thereof or a pharmaceutically-acceptable salt thereof.

According to a further aspect of the invention, there is provided a quinazoline derivative of the Formula I as disclosed hereinbefore wherein $Q^1$ is a quinazoline-like ring such as a group of the formula Ia, Ib, Ic or Id as disclosed hereinbefore wherein:

$Y^1$ together with the carbon atoms to which it is attached forms a 5- or 6-membered aromatic or partially unsaturated ring comprising 1 to 3 heteroatoms selected from O, N and S;

$Y^2$ together with one carbon atoms to which it is attached forms a 5- or 6-membered aromatic or partially unsaturated ring comprising 1 to 3 heteroatoms selected from O, N and S;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$Q^3—X^1—$$

wherein $X^1$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $OC(R^7)_2$, $SC(R^7)_2$ and $N(R^7)C(R^7)_2$, wherein $R^7$ is hydrogen or (1-6C)alkyl, and $Q^3$ is aryl, aryl-(1-6C)alkyl, (3-7C)cycloalkyl, (3-7C)cycloalkyl(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^8)$, CO, $CH(OR^8)$, $CON(R^8)$, $N(R^8)CO$, $SO_2N(R^8)$, $N(R^8)SO_2$, CH=CH and C≡C wherein $R^8$ is hydrogen or (1-6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^2—$$

wherein $X^2$ is a direct bond or is selected from CO and $N(R^9)CO$, wherein $R^9$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno substituents or a substituent selected from hydroxy, cyano, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$—X^3—Q^5$$

wherein $X^3$ is a direct bond or is selected from O, S, SO, $SO_2$, $N(R^{10})$, CO, $CH(OR^{10})$, $CON(R^{10})$, $N(R^{10})CO$, $SO_2N(R^{10})$, $N(R^{10})SO_2$, $C(R^{10})_2O$, $C(R^{10})_2S$ and $N(R^{10})C(R^{10})_2$, wherein $R^{10}$ is hydrogen or (1-6C)alkyl, and $Q^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$—X^4—R^{11}$$

wherein $X^4$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl, or from a group of the formula:

$$—X^5—Q^6$$

wherein $X^5$ is a direct bond or is selected from O and $N(R^{13})$, wherein $R^{13}$ is hydrogen or (1-6C)alkyl, and $Q^6$ is aryl, aryl-(1-6C)alkyl, heteroaryl, heteroaryl-(1-6C)alkyl, heterocyclyl or heterocyclyl-(1-6C)alkyl, and any $Q^6$ group optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo or thioxo substituents;

$R^2$ is hydrogen or (1-6C)alkyl and $R^3$ is hydrogen or (1-6C)alkyl, or $R^2$ and $R^3$ together form a $CH_2$, $(CH_2)_2$ or $(CH_2)_3$ group, $R^5$ is hydrogen or (1-6C)alkyl, or $R^5$ and $R^6$ together with the N atom to which they are attached form a 4- to 7-membered heterocyclic ring optionally containing a further heteroatom selected from O, N and S, provided that one of the pairs of groups $R^2$ and $R^4$ together, $R^3$ and $R^4$ together and $R^5$ and $R^4$ together forms a bond;

$Q^2$ is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituent with 1, 2, 3, or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)

alkylsulphamoyl, N,N-di-[(1-6C)alkyl]sulphamoyl, (1-6C) alkanesulphonylamino and N-(1-6C)alkyl-(1-6C) alkanesulphonylamino, or from a group of the formula:

$$-X^6-R^{14}$$

wherein $X^6$ is a direct bond or is selected from O and N($R^{15}$), wherein $R^{15}$ is hydrogen or (1-6C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

$$-X^7-Q^7$$

wherein $X^7$ is a direct bond or is selected from O, S, SO, $SO_2$, N($R^{16}$), CO, CH(O$R^{16}$), CON($R^{16}$), N($R^{16}$)CO, $SO_2$N($R^{16}$), N($R^{16}$)$SO_2$, C($R^{16}$)$_2$O, C($R^{16}$)$_2$S and C($R^{16}$)$_2$N($R^{16}$), wherein each $R^{16}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl, or $Q^2$ is optionally substituted with a (1-3C)alkylenedioxy group, and wherein any aryl, heteroaryl or heterocyclyl group within a substituent of $Q^2$ optionally bears 1, 2 or 3 substituents, which may be the same or different, selected from halogeno, influoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^8-R^{17}$$

wherein $X^8$ is a direct bond or is selected from O and N($R^{18}$), wherein $R^{18}$ is hydrogen or (1-6C)alkyl, and $R^{17}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within a substituent on $Q^2$ optionally bears 1 or 2 oxo or thioxo substituents; and $R^6$ is an optionally substituted group selected from (2-6C)alkenyl, (2-6C)alkynyl, (3-7C)cycloalkyl and (3-7C)cycloalkenyl, or $R^6$ is a substituted (1-6C) group, and wherein adjacent carbon atoms in any (2-6C)alkylene chain within a $R^6$ group are optionally separated by the insertion into the chain of a group selected from O, S, SO, $SO_2$, N($R^{19}$), CO, CH(O$R^{19}$), CON($R^{19}$), N($R^{19}$)CO, $SO_2$N($R^{19}$), N($R^{19}$)$SO_2$, CH=CH and C≡C wherein $R^{19}$ is hydrogen or (1-6C)alkyl, and wherein any $CH_2$=CH— or HC≡C— group within a $R^6$ group optionally bears at the terminal $CH_2$— or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^8-X^9-$$

wherein $X^9$ is a direct bond or is selected from CO and N($R^{20}$)CO, wherein $R^{20}$ is hydrogen or (1-6C)alkyl, and $Q^8$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^6$ group optionally bears one each said $CH_2$ or $CH_3$ group one or more of the following substituents, provided that the $R^6$ group when it is (1-6C)alkyl must bear at least one such substituent, one or more halogeno substituents or a substituent selected from hydroxy, cyano, amidino, amino, carboxy, carbamoyl, (1-6C)alkyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, (1-6C)alkoxycarbonylamino and N-(1-6C)alkyl-(1-6C)alkoxycarbonylamino, or from a group of the formula:

$$-X^{10}-Q^9$$

wherein $X^{10}$ is a direct bond or is selected from O, S. SO, $SO_2$, N($R^{21}$), CO, CH(O$R^{21}$), CON($R^{21}$), N($R^{21}$)CO, $SO_2$N($R^{21}$), N($R^{21}$)$SO_2$, C($R^{21}$)$_2$O, C($R^{21}$)$_2$S and N($R^{21}$)C($R^{21}$)$_2$, wherein $R^{21}$ is hydrogen or (1-6C)alkyl, and $Q^9$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a $R^6$ group, or any heterocyclic group formed with $R^5$ and $R^6$ together with the N atom to which they are attached form a ring, optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^{11}-R^{22}$$

wherein $X^{11}$ is a direct bond or is selected from O and N($R^{23}$), wherein $R^{23}$ is hydrogen or (1-6C)alkyl, and $R^{22}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl, or from a group of the formula:

$$-X^{12}-Q^{10}$$

wherein $X^{12}$ is a direct bond or is selected from O and N($R^{24}$), wherein $R^{24}$ is hydrogen or (1-6C)alkyl, and $Q^{10}$ is aryl, aryl-(1-6C)alkyl, heteroaryl, heteroaryl-(1-6C)alkyl, heterocyclyl or heterocyclyl-(1-6C)alkyl, and any $Q^{10}$ group optionally bears 1 or 2 substituents, which may be the same or different, selected from halogeno, (1-6C)alkyl and (1-6C)alkoxy, and wherein any heterocyclyl group within a $R^6$ group, or the heterocyclic group formed when $R^5$ and $R^6$ together with the N atom to which they are attached form a ring, optionally bears 1 or 2 oxo or thioxo substituents;

or a tautomer thereof or a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that the compounds of Formula I defined above may exhibit the phenomenon of tautomerism. In particular, tautomerism may affect the guanidino group formed when one of the pairs of groups $R^2$ and $R^4$ together, $R^3$ and $R^4$ together and $R^5$ and $R^4$ together forms a bond. For example, when each of $R^2$ and $R^3$ is hydrogen and $R^5$ and $R^4$ together form a bond, the generic structure of Formula I becomes the first of the three structures shown below and tautomeric equilibrium may give rise to the other two structures.

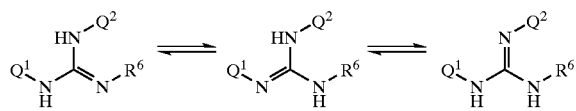

It is to be understood that the present invention includes in its definition any such tautomeric form, or a mixture thereof, which possesses the above-mentioned activity and is not to be limited merely to any one tautomeric form utilised within the formate drawings or named in the Examples.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that the hydrogen atom which is shown at the 2-position in each of the part structures of the formulae Ia, Ib, Ic and Id indicates that position remains unsubstituted by any $R^1$ group.

Suitable values for the generic radicals referred to above include those set out below.

A suitable value for any one of the 'Q' groups ($Q^2$ to $Q^{10}$) when it is aryl or for the aryl group within a 'Q' group is, for example, phenyl or naphthyl, preferably phenyl.

A suitable value for a (3-7C)cycloalkyl group within $Q^2$ or for $Q^3$, $Q^5$, $Q^9$ or $R^9$ when it is (3-7C)cycloalkyl is, for example, cyclopropyl, cyclobutyl, cyclopentyl, cyclohexyl, cycloheptyl or bicyclo[2.2.1]heptyl and a suitable values for $Q^3$, $Q^5$, $Q^9$ or $R^6$ when it is (3-7C)cycloalkenyl is, for example, cyclobutenyl, cyclopentenyl, cyclohexenyl or cycloheptenyl.

A suitable value for $Q^2$ when it is a 5- 6-membered monocyclic or a 9- or 10-membered bicyclic heteroaryl ring containing 1 or 2 nitrogen heteroatoms and optionally containing a further heteroatom selected from nitrogen, oxygen and sulphur is, for example, pyrrolyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, 1,3,5-triazenyl, indolyl, benzoxazolyl, benzimidazolyl, benzothiazolyl, indazolyl, benzofuranzinyl, quinolyl, isoquinolyl, quinazolinyl, quinoxalinyl, cinnolinyl or naphthyridinyl, preferably isoxazolyl, 1,2,3-triazolyl, pyridyl, benzothiazolyl, quinolyl or quinazolinyl.

A suitable value for any one of the 'Q' groups, $Q^3$ to $Q^{10}$, when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably thienyl, 1,2,3-triazolyl, pyridyl, quinolyl, quinazolinyl or quinoxalinyl.

A suitable value for any one of the 'Q' groups, $Q^3$ to $Q^{10}$, when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, pyrrolinyl, pyrrolidinyl, 1,4-dioxanyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, or a benzo derivative thereof such as 2,3-dihydrobenzofuranyl, 2,3-dihydrobenzothienyl, indolinyl, chromanyl, 1,4-benzodioxanyl and 1,2,3,4-tetrahydroquinolinyl. Preferably any one of the 'Q' groups, $Q^3$ to $Q^{10}$, when it is heterocyclyl or for the heterocyclyl group within a 'Q' group is, for example, pyrrolidin-1-yl, pyrrolidin-2-yl, 1,4-dioxan-2-yl, morpholino, 1,1-dioxotetrahydro-4H-1,4-thiazin-4-yl, piperidino, piperidin-3-yl, piperidin-4-yl, homopiperidin-1-yl, piperazin-1-yl or homopiperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for the heterocyclyl ring formed when $R^5$ and $R^6$ together with the N atom to which they are attached from a 4- to 7-membered heterocyclic ring optionally containing a further heteroatom selected from O, N and S is, for example, pyrrolin-1-yl, pyrrolidin-1-yl, morpholino, tetrahydro-4H-1,4-thiazin-4-yl, 1,1-dioxotetrahydro-4H-1,4-thiazin-4-yl, piperidino, homopiperidin-1-yl, piperazin-1-yl or homopiperazin-1-yl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C)alkyl, (3-7C)cycloalkyl-(1-6C)alkyl, (3-7C)cycloalkenyl-(1-6C)alkyl or heterocyclyl-(1-6C)alkyl group is present.

When, as defined hereinbefore, $Y^1$ together with the carbon atoms to which it is attached forms a 5- or 6-membered aromatic or partially unsaturated ring comprising 1 to 3 heteroatoms selected from O, N and S, ring Y¹ is suitably unsaturated or partially unsaturated wherein a —CH₂— group can optionally be replaced by a —CO— group and ring nitrogen atom may optionally bear a (1-6C)alkyl group. Diradicals of suitable fused Y¹ rings include thiendiyl, furandiyl, imidazolediyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyrazinediyl, pyridazinediyl and 1,3,4-triazinediyl, Examples of suitable bicyclic rings of formula Ic formed by the fusion of ring Y¹ to the adjacent pyrimidine ring include furopyrimidinyl, thienopyrimidinyl, purinyl, pyrrolopyrimidinyl, pyrrolinopyrimidinyl, oxopyrrolinopyrimidinyl, oxazolopyrimidinyl, oxazolinopyrimidinyl, oxooxazolinopyrimidinyl, osoxazolopyrimidinyl, thiazolopyrimidinyl, thiazolinopyrimidinyl, oxothiazolinopyrimidinyl, isothiazolopyrimidinyl, oxoimidazolinopyrimidinyl, pyrazolopyrimidinyl, pyrazolinopyrimidinyl, oxapyrazolinopyrimidinyl, pyridopyrimidinyl, pyrimidopyrimidinyl and pteridinyl. Preferably the bicyclic ring of formula Ic is furo[3,2-d]pyrimidinyl, furo[2,3-d]pyrimidinyl, thieno[3,2-d]pyrimidinyl, thieno[2,3-d]pyrimidinyl, purinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-pyrimidinyl, pyrido[2,3-d]pyrimidinyl, pyrido[3,4-d]pyrimidinyl, pyrido[4,3-d]pyrimidinyl, pyrido[3,2-d]pyrimidinyl, pyrimido[4,5-d]pyrimidinyl, pyrimido[5,6-d]pyrimidinyl or pteridinyl. More specifically the bicyclic ring of formula Ic is 6-oxopyrrolino[2,3-d]pyrimidin-4-yl, 6-oxopyrrolino[3,2-d]pyrimidin-4-yl, 2-oxooxazolino[5,4-d]pyrimidin-7-yl, 2-oxothiazolino[5,4-d]pyrimidin-7-yl, 2-oxooxazolino[4,5-d]pyrimidin-7-yl, 2-oxothiazolino[4,5-d]pyrimidin-7-yl, 2-oxoimidazolino[4,5d]pyrimidin-7-yl, 3-oxopyrazolino[3,4-d]pyrimidin-4-yl or 3-oxopyrazolino[4,3-d]pyrimidin-7-yl. Further preferred bicyclic rings of formula Ic include thieno[3,2-d]pyrimidinyl, thieno[2,3d]pyrimidinyl, thiazolo[5,4-d]pyrimidinyl, 6-purinyl, pyrido[2,3-d]pyrimidinyl, pyrido[3,4-d]pyrimidinyl, pyrido[4,3-d]pyrimidinyl, pyrido[3,2-d]pyrimidinyl and pteridinyl, more specifically thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl and pteridin-4-yl.

When, as defined hereinbefore, Y² together with the carbon atoms to which it is attached forms a 5- or 6-membered aromatic or partially unsaturated ring comprising 1 to 3 heteroatoms selected from O, N and S, ring Y² is suitably unsaturated or partially unsaturated wherein a —CH₂— group can optionally be replaced by a —CO— group and a ring nitrogen atom may optionally bear a (1-6C)alkyl group. Diradicals of suitable fused Y² rings include thiendiyl, furandiyl, imidazolediyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyrazinediyl, pyridazinediyl and 1,3,4-triazinediyl, Examples of suitable tricyclic rings of formula Id formed by the fusion of ring Y² to the adjacent quinazoline ring include imidazolquinazolinyl, oxazoloquinazolinyl, thiazoloquinazolinyl, [1,2,3]triazoloquinaolinyl, pyrazoloquinazolinyl, pyrroloquinazolinyl, oxoimidazolinoquinazolinyl, oxooxazolinoquinazolinyl, oxothiazolinoquinazolinyl and oxopyrazolinoquinazolinyl. Preferably the tricyclic ring of formula Id is 3H-imidazol[4,5-g]quinazolinyl, oxazolo[4,5-g]quinazolinyl, thiazolo[4,5-g]quinazolinyl, 3H-[1,2,3]triazolo[4,5-g]quinazolinyl, 1H-pyrazolo[3,4-g]quinazolinyl, 6H-pyrrolo[2,3-g]quinazolinyl, 2-oxo-1,2-dihydro-3-H-imidazol[4,5-g]quinazolinyl, 2-oxo-1,2-dihydrooxazolo[4,5-g]quinazolinyl, 2-oxo-1,2-dihydrothiazole[4,5g]quinazolinyl, 3-oxo-2,3-dihydro-1H-pyrazolo[3,4-g]quinazolinyl, pyrido[2,3-g]quinazolinyl, pyrimidino[4,5g]cinnolinyl, pyrimidino[4,5-g]quinaolzinyl, pyrazino[2,3-g]quinazolinyl, 7-oxo-6,7-dihydropyrido[2,3-g]quinaozlinyl, pyrazino[2,3g]quinazolinyl and 8-oxo-8,9-dihydropyrazino[2,3g]quinazolinyl, More specifically the tricylic ring of formula Id is 3H-imidazolo[4,5-g]quinazolin-8-yl, oxazolo[4,5-g]quinazolin-8-yl, thiazolo[4,5-g]quinazolin-8-yl, 3-H-[1,2,3]triazolo[4,5-g]quinazolin-8-yl, 1H-pyrazolo[3,4-g]quinazolin-8-yl, 6H-pyrrolo[2,3g]quinazolin-4-yl, 2-oxo-1,2-dihydro-3H-imidazol[4,5-g]quinazolin-8-yl, 2-oxo-1,2-dihydrooxazolo[4,5g]quinazolin-8-yl, 2-oxo-1,2-dihydrothiazolo[4,5-g]quinazolin-8-yl, 3-oxo-2,3-dihydro-1H-pyrazolo[3,4-g]quinazolin-8yl, pyrido[2,3-g]quinazolin-4-yl, pyrimidino[4,5-g]cinnolin-9-yl, pyrimidino[4,5-g]quinazolin-4-yl, pyrazino[2,3-g]quinazolin-4-yl, 7-oxo-6,7-dihydropyrido[2,3-g]quinazolin-4-yl, pyrazino[2,3-g]quinazolin-4-yl, 8-oxo-8,9-dihydropyrazino[2,3-g]quinazolin-4-yl. Further preferred tricyclic rings of formula Id include 3-methyl-3-H-imidazol[4,5-g]quinazolin-8-yl, 3-methyl-3H-[1,2,3]triazolo[4,5g]quinazolin-8-yl, 3-methyl-2-oxo-1,2-dihydro-3-H-imidazol[4,5-g]quinazolin-8-yl, pyrazino[2,3-g]quinazolin-4-yl and 9-methyl-8-oxo-8,9-dihydropyrazino[2,3-g]quinazolin-4-yl.

Suitable values for any of the 'R' groups ($R^1$ to $R^{24}$), or for various groups within an $R^1$ substituent, or within a substituent on $R^6$ or $Q^2$ include:

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]-carbamoyl: | N,N-dimethylcarbamoyl, N-methylcarbamoyl and N,N-diethylcarbamoyl; |
| for (2-6C)alkanoyl: | acetyl and propionyl; |
| for (2-6C)alkanoyloxy: | acetoxy and propionyloxy; |
| for (2-6C)alkanoylamino: | acetamido and propionamido; |
| for N-(1-6C)alkyl(2-6C)alkanoylamino: | N-methylacetamido and N-methylpropionamido; |
| for N-(1-6C)alkylsulphamoyl: | N-methylsulphamoyl and N-ethylsulphamoyl; |
| for N,N-di-[(1-6C)alkyl]-sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for (3-6C)alkenoylamino: | acrylamido, methacrylamido and crotonamido; |

-continued

| | |
|---|---|
| for N-(1-6C)alkyl-(3-6C)alkenoyl-amino: | N-methylacrylamido and N-methylcrotonamido; |
| for (3-6C)alkynoylamino: | propiolamido; |
| for N-(1-6C)alkyl-(3-6C)alkynoyl-amino: | N-methylpropiolamido; |
| for (1-6C)alkoxycarbonylamino: | methoxycarbonylamino, ethoxycarbonylamino and tert-butoxycarbonylamino; |
| for N-(1-6C)alkyl-(1-6C)alkoxycarbonylamino: | N-methylmethoxycarbonylamino, N-methylethoxycarbonylamino and N-methyl-tert-butoxycarbonylamino; |
| for N-[hydroxy-(2-6C)alkyl]-carbamoyl: | N-(2-hydroxyethyl)carbamoyl and N-(3-hydroxypropyl)carbamoyl; |
| for N-[(1-6C)alkoxy-(2-6C)alkyl]-carbamoyl: | N-(2-methoxyethyl)carbamoyl and N-(3-methoxypropyl)carbamoyl |
| for N-[amino-(2-6C)alkyl]-carbamoyl: | N-(2-aminoethyl)carbamoyl and N-(3-aminopropyl)carbamoyl; |
| for N-[(1-6C)alkylamino-(2-6C)-alkyl]carbamoyl: | N-(2-methylaminoethyl)carbamoyl and N-(3-methylaminopropyl)-carbamoyl; |
| for N-{di-[(1-6C)alkyl]-amino-(2-6C)alkyl}carbamoyl: | N-(2-dimethylaminoethyl)carbamoyl and N-(3-dimethylaminopropyl)-carbamoyl; |
| for N,N-di-[hydroxy-(2-6C)alkyl]-carbamoyl: | N,N-di-(2-hydroxyethyl)carbamoyl and N,N-di-(3-hydroxypropyl)-carbamoyl; |
| for N,N-di-[(1-6C)alkoxy-(2-6C)-alkyl]carbamoyl: | N,N-di-(2-methoxyethyl)carbamoyl and N,N-di-(3-methoxypropyl)-carbamoyl; |
| for N,N-di-[amino-(2-6C)alkyl]-carbamoyl: | N,N-di-(2-aminoethyl)carbamoyl and N,N-di-(3-aminopropyl)carbamoyl; |
| for N,N-di-[(1-6C)alkylamino-(2-6C)alkyl]carbamoyl: | N,N-di-(2-methylaminoethyl)-carbamoyl and N,N-di-(3-methylaminopropyl)carbamoyl; |
| for N,N-di-{di-[(1-6C)alkyl]-amino-(2-6C)alkyl}carbamoyl: | N,N-di-(2-dimethylaminoethyl)-carbamoyl and N,N-di-(3-dimethylaminopropyl)carbamoyl; |
| for amino-(1-6C)alkyl: | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)-alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydxoxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for (2-6C)alkanoylamino-(1-6C)-alkyl: | acetamidomethyl, propionamidomethyl and 2-acetamidoethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl; |
| for carbamoyl-(1-6C)alkyl: | carbamoylmethyl and 2-carbamoylethyl; |
| for N-(1-6C)alkylcarbamoyl-(1-6C)-alkyl: | N-methylcarbamoylmethyl, N-ethylcarbamoylmethyl and 2-(N-methylcarbamoyl)ethyl; |
| for N,N-di-[(1-6C)alkyl]-carbamoyl-(1-6C)alkyl: | N,N-dimethylcarbamoylmethyl, N-ethyl-N-methylcarbamoylmethyl, N,N-diethylcarbamoylmethyl and 2-(N,N-dimethylcarbamoyl)ethyl. |

A suitable value for $(R^1)_m$ or for a substituent on $Q^2$ when it is (1-3C)alkylenedioxy is, for example, methylenedioxy or ethylenedioxy and the oxygen atoms thereof occupy adjacent ring positions.

When, as defined hereinbefore, an $R^1$ group forms a group of the formula $Q^3$—$X^1$— and, for example, $X^1$ is a $OC(R^7)_2$ linking group, it is the carbon atom, not the oxygen atom, of the $OC(R^7)_2$ linking group which is attached to the quinazoline-like ring such as the ring of formula Ia and the oxygen atom is attached to the $Q^3$ group. Similarly, when, for example a $CH_3$ group with a $R^1$ substituent bears a group of the formula —$X^3$—$Q^5$ and, for example, $X^3$ is a $C(R^{10})_2O$ linking group, it is the carbon atom, not the oxygen atom, of the $C(R^{10})_2O$ linking group which is attached to the $CH_3$ group and the oxygen atom is linked to the $Q^5$ group. A similar convention applies to the attachment of the groups of the formulae $Q^4$—$X^2$—, —$X^7$—$Q^7$ and —$X^{10}$—$Q^9$.

As defined hereinbefore, adjacent carbon atoms in any (2-6C)alkylene chain within a $R^1$ substituent or a $R^6$ group may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido) ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$—$X^2$— wherein $X^2$ is, for example, NHCO and $Q^4$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethylnyl groups such as N-(2-pyrrolidin-1-ylethyl)carbamoylethynyl. Similar suitable values are applicable to any such substituted $CH_2$=CH— or HC≡C— group within a $R^6$ group.

When, as defined hereinbefore, any $CH_2$ or $CH_3$ group within a $R^1$ substituent or a $R^6$ group bears on each said $CH_2$ or $CH_3$ group one or more halogeno substituents, there are suitably 1 or 2 halogeno substituents present on each said $CH_2$ group and there are suitably 1, 2 or 3 halogeno substituents present on each said $CH_3$ group.

When, as defined hereinbefore, any $CH_2$ or $CH_3$ group within a $R^1$ substituent or a $R^6$ group bears on each said $CH_2$ or $CH_3$ group a substituent as defined hereinbefore, suitable $R^1$ substituents or $R^6$ groups so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted amino(2-6C)alkoxy groups such as 3-amino-2-hydroxypropoxy, hydroxy-substituted (1-6C)alkylamino-(2-6C) alkoxy group such as 2-hydroxy-3-methylaminopropoxy, hydroxy-substituted di-[(1-6C)alkyl]amino-(2-6C)alkoxy groups such as 3-dimethylamino-2-hydroxypropoxy, hydroxy-substituted heterocyclyl-(1-6C)alkylamino groups such as 2-hydroxy-3-piperidinopropylamino and 2-hydroxy-3-morpholinopropylamino, hydroxy-substituted amino-(2-6C)alkylamino groups such as 3-amino-2-hydroxypropylamino, hydroxy-substituted (1-6C)alkylamino-(2-6C)alkylamino groups such as 2-hydroxy-3-methylaminopropylamino, hydroxy-substituted di-[(1-6C)alkyl]amino-(2-6C)alkylamino groups such as 3-dimethylamino-2-hydroxypropylamino, hydroxy-substituted (1-6C)alkyl groups such as 2-hydroxyethyl and 2,3-dihydroxypropyl, hydroxy-substituted (1-6C)alkoxy groups such as 2-hydroxyethoxy and 2,3-dihydroxypropoxy, (1-6C)alkoxy-substituted (1-6C)alkyl groups such as 2-methoxyethyl and 3-ethoxypropyl, (1-6C)alkoxy-substituted (1-6C)alkoxy groups such as 2-methoxyethoxy and 3-ethoxypropoxy, di-[(1-6C)alkyl]amino-(2-6C) alkyl groups such as 2-dimethylaminoethyl and 3-dimethylaminopropyl, (1-6C)alkylsulphonyl-substituted (1-6C)alkyl groups such as 2-methylsulphonylethyl, (1-6C)alkylsulphonyl-substituted (1-6C)alkoxy groups such as 2-methylsulphonylethoxy, hydroxy-substituted (3-7C)cycloalkyl groups such as 4-hydroxycyclohexyl and heterocyclyl-substituted (1-6C)alkylamino-(1-6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, (i) quinazoline derivatives of the Formula II

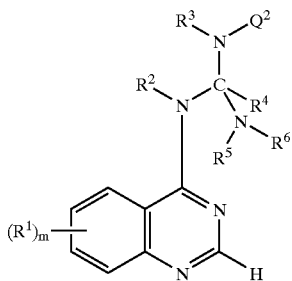

wherein each of m, $R^1$, $R^2$, $R^3$, $R^4$, $R^5$, $R^6$ and $Q^2$ has any of the meanings defined hereinbefore;

(ii) quinoline derivatives of the Formula III

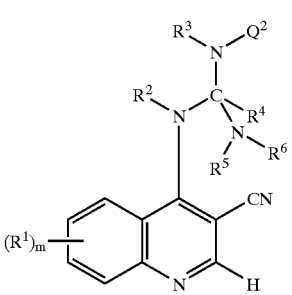

wherein each of m, $R^1$, $R^2$, $R^3$, $R^4$, $R^5$, $R^6$ and $Q^2$ has any of the meanings defined hereinbefore;

(iii) pyrimidine derivatives of the Formula IV

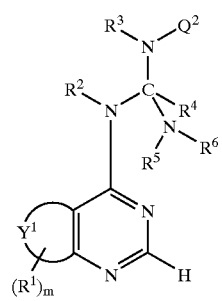

wherein each of m, $R^1$, $Y^1$, $R^2$, $R^3$, $R^4$, $R^5$, $R^6$ and $Q^2$ has any of the meanings defined hereinbefore; and (iv) quinazoline derivatives of the Formula V

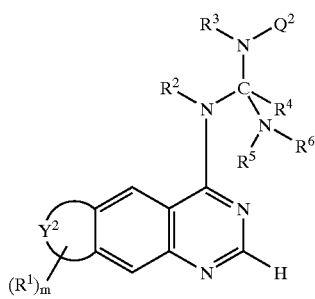

wherein each of m, $R^1$, $Y^2$, $R^2$, $R^3$, $R^4$, $R^5$, $R^6$ and $Q^2$ has any of the meanings defined hereinbefore.

Subject to the provisos described hereinbefore, further particular novel compounds of the invention include, for example, quinazoline derivatives of the Formula II, or pharmaceutically-acceptable salts thereof, wherein unless otherwise stated, each of m, $R^1$, $R^2$, $R^3$, $R^4$, $R^5$, $R^6$ and $Q^2$ has any of the meanings defined hereinbefore or in paragraphs (a) to (j) hereinafter:—

(a) m is 1, 2 or 3, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

$$Q^3—X^1—$$

wherein $X^1$ is a direct bond or is selected from O, N($R^7$), CON($R^7$), N($R^7$)CO and OC($R^7$)$_2$ wherein $R^7$ is hydrogen or (1-6C)alkyl, and $Q^3$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, N($R^8$), CON($R^8$), N($R^8$)CO, CH=CH and C≡C wherein $R^8$ is hydrogen or (1-6C)alkyl, and wherein any CH$_2$=CH— or HC≡C— group within a R$^1$ substituent optionally bears at the terminal CH$_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

Q$^4$—X$^2$— wherein X$^2$ is a direct bond or is CO or N(R$^9$)CO, wherein R$^9$ is hydrogen or (1-6C)alkyl, and Q$^4$ is heteroaryl, heteroaryl-(1-6C)alkyl, heterocyclyl or heterocyclyl-(1-6C)alkyl, and wherein any CH$_2$ or CH$_3$ group within a R$^1$ substituent optionally bears on each said CH$_2$ or CH$_3$ group a substituent selected from hydroxy, amino, (1-6C)alkoxy, (1-6C)alkylsulphonyl, (1-6C)alkylamino and di-[(1-6C)alkyl]amino, or from a group of the formula:

—X$^3$—Q$^5$ wherein X$^3$ is a direct bond or is selected from O, N(R$^{10}$), CON(R$^{10}$), N(R$^{10}$), N(R$^{10}$)CO and C(R$^{10}$)$_2$O, wherein R$^{10}$ is hydrogen or (1-6C)alkyl, and Q$^5$ is heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, carbamoyl, (1-6C)alkyl, (1-6C)alkoxy, N-(1-6C)alkylcarbamoyl, N,N-di-[(1-6C)alkyl]carbamoyl, amino-(1-6C)alkyl, (1-6C)alkylamino-(1-6C)alkyl, di-[(1-6C)alkyl]amino-(1-6C)alkyl, (2-6C) alkanoylamino-(1-6C)alkyl and (1-6C)alkoxycarbonylamino-(1-6C)alkyl, and wherein any heterocyclyl group within a substituent on R$^1$ optionally bears 1 or 2 oxo substituents;

(b) m is 1, 2 or 3, and each R$^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

Q$^3$—X$^1$— wherein X$^1$ is a direct bond or is selected from O, NH, CONH, NHCO and OCH$_2$ and OCH$_2$ and Q$^3$ is phenyl, benzyl, cyclopropylmethyl, thienyl, 1-imidazolyl, 1,2,3-triazolyl, pyridyl, 2-imidazol-1-ylethyl, 3-imidazol-1-ylpropyl, 2-(1,2,3-triazolyl)ethyl, 3-(1,2,3-triazolyl)propyl, pyridylmethyl, 2-pyridylethyl, 3-pyridylpropyl, pyrrolidin-1-yl, pyrrolidin-2-yl, morpholino, 1,1-dioxotetrahydro-4H-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl-2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2-6C)alkylene chain within a R$^1$ substituent are optionally separated by the insertion into the chain of a group selected from O, NH, CONH, NHCO, CH=CH and C≡C, and wherein any CH$_2$=CH— or HC≡C— group within a R$^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl and methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

Q$^4$—X$^2$— wherein X$^2$ is a direct bond or is CO, NHCO or N(Me)CO and Q$^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a R$^1$ substituent optionally bears on each said CH$_2$ or CH$_3$ group a substituent selected from hydroxy, amino, methoxy, methylsulphonyl, methylamino and dimethylamino, or from a group of the formula:

—X$^3$—Q$^5$ wherein X$^3$ is a direct bond or is selected from O, NH, CONH, NHCO and CH$_2$O and Q$^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperdin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on R$^1$ optionally bears 1, 2 or 3 substituents, which may be the same or different, selected from fluoro, chloro, trifluoromethyl, hydroxy, amino, carbamoyl, methyl, ethyl, methoxy, aminomethyl, methylaminomethyl, dimethylaminomethyl, acetamidomethyl, methoxycarbonylaminomethyl, ethoxycarbonylaminomethyl, and tert-butoxycarbonylaminomethyl, and wherein any heterocyclyl group within a substituent on R$^1$ optionally bears 1 and 2 oxo substituents;

(c) m is 1 or 2 and the R$^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4-H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, CH=CH and C≡C, and wherein $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^4$—$X^2$— wherein $X^2$ is a direct bond or is NHCO or N(Me)CO and $Q^4$ is imidazolylmethyl, 2-imidazolylethyl, 3-imidazolylpropyl, pyridylmethyl, 2-pyridylethyl, 3-pyridylpropyl pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, aminomethyl, acetamidomethyl and tert-butoxycarbonylaminomethyl, and wherein any heterocyclyl group within a substituent on $R^1$ optionally bears 1 or 2 oxo substituents:

(d) each of $R^2$, $R^3$ and $R^5$ is hydrogen or methyl except that one of the pairs of group $R^2$ and $R^4$ together, $R^3$ and $R^4$ together and $R^5$ and $R^4$ together forms a bond;

(e) each of $R^2$, $R^3$ and $R^5$ is hydrogen except that one of the pairs of groups $R^2$ and $R^4$ together, $R^3$ and $R^4$ together and $R^5$ and and $R^4$ together forms a bond;

(f) each of $R^2$ and $R^3$ is hydrogen and $R^5$ and $R^6$ together with the N atom to which they are attached form a 4- to 7-membered heterocyclic ring optionally containing a further heteroatom selected from O, N and S, provided that one of the pairs of groups $R^2$ and $R^4$ together and $R^3$ and $R^4$ together forms a bond;

(g) $Q^2$ is phenyl, benzyl, α-methylbenzyl, phenethyl, naphthyl, 1-(1-naphthyl)ethyl or 2-phenylcyclopropyl which is optionally substituted with 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, or from a group of the formula:

—$X^6$—$R^{14}$ wherein $X^6$ is a direct bond or is selected from O and N($R^{15}$), wherein $R^{15}$ is hydrogen or (1-6C)alkyl, and $R^{14}$ is hydroxy-(1-6C)alkyl, (1-6C)alkoxy-(1-6C)alkyl, amino-(1-6C)alkyl, (1-6C)alkylamino-(1-6C)alkyl or di-[(1-6C)alkyl]amino-(1-6C)alkyl, or from a group of the formula:

—$X^7$—$Q^7$ wherein $X^7$ is a direct bond or is selected from O, N($R^{16}$), CO, CON($R^{16}$), N($R^{16}$)CO and C($R^{16}$)$_2$O, wherein each $R^{16}$ is hydrogen or (1-6C)alkyl, and $Q^7$ is phenyl, benzyl, heteroaryl or heteroaryl-(1-6C)alkyl, and wherein any phenyl or heteroaryl group within a substituent on $Q^2$ optionally bears 1, 2 or 3 substituents, which may be the same or different, selected from halogeno, trifluoromethyl, hydroxy, amino, (1-6C)alkyl and (1-6C)alkoxy;

(h) $Q^2$ is phenyl, benzyl, α-methylbenzyl or phenethyl which is optionally substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy, or from a group of the formula:

—$X^7$—$Q^7$ wherein $X^7$ is a direct bond or is selected from O and CO, and $Q^7$ is phenyl, benzyl, pyridyl or pyridylmethyl, and wherein any phenyl or pyridyl group within a substituent on $Q^2$ optionally bears 1 or 2 substituents, which may be the same or different, selected from fluoro, chloro, trifluoromethyl, hydroxy, amino, methyl and methoxy;

(i) $Q^2$ is phenyl, benzyl or phenethyl which is substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that at least one substituent is located at an ortho position (for example the 2-position on a phenyl group);

(j) $Q^2$ is phenyl, benzyl or phenethyl which is substituted with 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that two substituents are located at ortho positions (for example the 2- and 6-positions on a phenyl group);

(k) $R^6$ is an optionally substituted group selected from (2-6C)alkenyl, (2-6C)alkynyl, (3-7C)-cycloalkyl and (3-7C) cycloalkenyl, or $R^6$ is substituted (1-6C)alkyl group, and wherein adjacent carbon atoms in any (2-6C)alkylene chain within a $R^6$ group are optionally separated by the insertion into the chain of a group selected from O, $N(R^{19})$, $CON(R^{19})$, $N(R^{19})CO$, CH=CH and C≡C wherein $R^{19}$ is hydrogen or (1-6C)alkyl, and wherein any $CH_2$=CH— or HC≡C— group within a $R^6$ group optionally bears at the terminal $CH_2$= or HC≡ position a substituent selected from carbamoyl, N-(1-6C) alkylcarbamoyl, N,N-di-[(1-6C)alkyl]carbamoyl, amino-(1-6C)alkyl, (1-6C)alkylamino-(1-6C)alkyl di-[(1-6C)alkyl] amino-(1-6C)alkyl or from a group of the formula:

$$Q^8-X^9-$$

wherein $X^9$ is a direct bond or is CO or $N(R^{20})CO$, wherein $R^{20}$ is hydrogen or (1-6C)alkyl, and $Q^8$ is heteroaryl, heteroaryl-(1-6C)alkyl, heterocyclyl or heterocyclyl-(1-6C) alkyl, and wherein any $CH_2$ or $CH_3$ group within a $R^6$ group optionally bears on each said $CH_2$ or $CH_3$ group one or more of the following substituents, provided that the $R^6$ group when it is (1-6C)alkyl must bear at least one such substituent, one or more halogeno substituents or a substituent selected from hydroxy, cyano, amidino, amino, carboxy, (1-6C)alkoxy, (1-6C)alkylthio, (1-6C)alkylsulphinyl, (1-6C) alkylsulphonyl, (1-6C)alkylamino, di-[(1-6C)alkyl]amino, (1-6C)alkoxycarbonyl, (2-6C)alkanoylamino, N-(1-6C) alkyl-(2-6C)alkanoylamino, (1-6C)alkanesulphonylamino, N-(1-6C)alkyl-(1-6C)alkanesulphonylamino, (1-6C)alkoxycarbonylamino and N-(1-6C)alkyl-(1-6C)alkoxycarbonylamino, or from a group of the formula: wherein $X^{10}$ is a direct bond or is selected from O, $N(R^{21})$, $CON(R^{21})$, $N(R^{21})CO$ and $C(R^{21})_2O$ wherein $R^{21}$ is hydrogen or (1-6C) alkyl, and $Q^9$ is phenyl, phenyl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C) alkyl, and wherein any aryl, heteroaryl or heterocyclyl group within a $R^6$ group optionally bears 1, 2 or 3 substituents, which may be the same or different, selected from halogeno, trifluoromethyl, hydroxy, amino, carbamoyl, (1-6C)alkyl, (1-6C)alkoxy, N-(1-6C)alkylcarbamoyl, N,N-di-[(1-6C) alkyl]carbamoyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl and (1-6C)alkoxycarbonylamino-(1-6C)alkyl, and wherein any heterocyclyl group within a $R^6$ group optionally bears 1 or 2 oxo substituents;

(l) $R^6$ is an optionally substituted group selected from allyl, 2-propynyl, cyclopropyl, cyclobutyl, cyclopentyl, cyclohexyl and cycloheptyl, or $R^6$ is a substituted methyl, ethyl, propyl or butyl group, and wherein adjacent carbon atoms in any (2-6C)alkylene chain within a $R^6$ group are optionally separated by the insertion into the chain of a group selected from O, NH, CONH, NHCO, CH=CH and C≡C, and wherein any $CH_2$=CH— or HC≡C— group within a $R^6$ group optionally bears at the terminal $CH_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$$Q^8-X^9-$$

wherein $X^9$ is a direct bond or is CO, NHCO or N(Me)CO and $Q^8$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^6$ group optionally bears on each said $CH_2$ or $CH_3$ group one or more of the following substituents, provided that the $R^6$ group when it is a methyl, ethyl, propyl or butyl group must bear at least one such substituent, one or more substituents selected from fluoro, chloro and bromo or a substituent selected from hydroxy, cyano, amidino, amino, carboxy, methoxy, ethoxy, methylthio, methylsulphinyl, methylsulphonyl, methylamino, dimethylamino, methoxycarbonyl, ethoxycarbonyl, propoxycarbonyl, tert-butoxycarbonyl, acetamido, propionamido N-methylacetamido, N-methylpropionamido, methoxycarbonylamino, ethoxycarbonylamino and tert-butoxycarbonylamino, or from a group of the formula:

$$-X^{10}-Q^{10}$$

wherein $X^{10}$ is a direct bond or is selected from O, NH, CONH, NHCO and $CH_2O$ and $Q^9$ is phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, imidazolyl, imidazolylmethyl 1,2,3-triazolyl, 1,2,3-triazolylmethyl, pyridylmethyl, tetrahydrofuran-2-yl, tetrahydrofuran-3-yl, pyrrolidin-1-yl, pyrrolidin-2-yl, 1,4-dioxan-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a $R^6$ group optionally bears 1, 2 or 3 substituents, which may be the same or different, selected from fluoro, chloro, trifluoromethyl, hydroxy, amino, carbamoyl, methyl, ethyl, methoxy, aminomethyl, methylaminomethyl, dimethylaminomethyl, acetamidomethyl, methoxycarbonylaminomethyl, ethoxycarbonylaminomethyl and tert-butoxycarbonylaminomethyl, and wherein any heterocyclyl group within a $R^6$ group optionally bears 1 or 2 oxo substituents; and (m) $R^6$ is an optionally substituted group selected from allyl, 2-propynyl, cyclopropyl, cyclobutyl, cyclopentyl and cyclohexyl, or $R^6$ is substituted methyl, ethyl, propyl or butyl group, and wherein adjacent carbon atoms in any (2-6C)alkylene chain within a $R^6$ group are optionally separated by the insertion in to the chain of a group selected from O, NH, CH=CH and C≡C, and wherein any $CH_2$ or $CH_3$ group within a $R^6$ group optionally bears on each said $CH_2$ or $CH_3$ group one or more of the following substituents, provided that the $R^6$ group when it is a methyl, ethyl, propyl or butyl group must bear at least one such substituent, one, two or three fluoro substituents or a substituent selected from hydroxy, cyano, amidino, amino, carboxy, methoxy, methylthio, methylsulphinyl, methylsulphonyl, methylamino, dimethylamino, methoxycarbonyl, ethoxycarbonyl, propoxycarbonyl, tert-butoxycarbonyl, acetamido, phenyl, cyclopropyl, cyclobutyl, cyclopentyl, cyclohexyl, 1-imidazolyl, 2-imidazolyl, 4-imidazolyl, 2-pyridyl, 3-pyridyl, 4-pyridyl, tetrahydrofuran-2-yl, pyrrolidin-1-yl, 1,4-dioxan-2-yl, morpholino, piperidino, piperazin-1-yl, homopiperidin-1-yl and homopiperazin-1-yl, and wherein any phenyl, imidazolyl, pyridyl or heterocyclyl group within a $R^6$ group optionally bears 1 or 2 substituents, which may be the same or different, selected from fluoro, chloro, trifluoromethyl, hydroxy, amino, carbamoyl, methyl, ethyl and methoxy, and wherein any heterocyclyl group within a $R^6$ group optionally bears 1 or 2 oxo substituents.

Further particular novel compounds of the invention include, for example, quinoline derivatives of the Formula III, pharmaceutically-acceptable salts thereof, wherein, unless otherwise stated, each of m, $R^1$, $R^2$, $R^3$, $R^4$, $R^5$, $R^6$ and $Q^2$ has any of the meanings defined hereinbefore or in any of the paragraphs (a) to (m) immediately hereinbefore.

Further particular novel compounds of the invention include, for example, pyrimidine derivatives of the Formula IV, or pharmaceutically-acceptable salts thereof, wherein, unless otherwise stated, each of m, $R^1$, $R^2$, $R^3$, $R^4$, $R^5$, $R^6$ and $Q^2$ has any of the meanings defined hereinbefore or in any of the paragraphs (a) to (m) immediately hereinbefore and $Y^1$ has any of the meanings defined hereinbefore or in paragraphs (a) to (c) hereinafter:—

(a) bicyclic rings formed by the fusion of ring $Y^1$ to the adjacent pyrimidine ring include thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl and pyrido[3,2-d]pyrimidin-4-yl;

(b) bicyclic rings formed by the fusion of ring $Y^1$ to the adjacent pyrimidine ring include thieno[3,2-d]pyrimidin-4-yl, pyrido[3,4-d]pyrimidin-4-yl, pyrido[4,3-d]pyrimidin-4-yl and pyrido[3,2-d]pyrimidin-4-yl; and (c) the bicyclic ring formed by the fusion of ring $Y^1$ to the adjacent pyrimidine ring is thieno[3,2d]pyrimidin-4-yl.

Further particular novel compounds of the invention include, for example, quinazoline derivatives of the Formula V, or pharmaceutically-acceptable salts thereof, wherein unless otherwise stated, each of m, $R^1$, $R^2$, $R^3$, $R^4$, $R^5$, $R^6$ and $Q^2$ has any of the meanings defined hereinbefore or in any of the paragraphs (a) to (m) immediately hereinbefore and $Y^2$ has any of the meanings defined hereinbefore or in paragraphs (a) and (b) hereinafter:—

(a) tricyclic rings formed by the fusion of ring $Y^2$ to the adjacent quinazoline ring include 3H-imidazol[4,5-g]quinazolin-8-yl and 2-oxo-1,2-dihydro-3-H-imidazo[4,5-g]quinazoline-8-yl; and (b) tricyclic rings formed by the fusion of ring $Y^2$ to the adjacent quinazoline ring include 3-methyl-3H-imidazo[4,5-g]quinazolin-8yl and 3-methyl-2-oxo-1,2-dihydro-3H-imidazol-[4,5-g]quinazolin-8-yl.

A preferred compound of the invention is a quinazoline derivative of the Formula II wherein:

m is 1 and the $R^1$ group is located at the 6- or 7-position and is selected from methoxy, benzyloxy, cyclopropylmethoxy, 2-dimethylaminoethoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-ylpropoxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 2-(2-oxoimidazolidin-1-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1-yl)propoxy, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 2-methylsulphonylethoxy, 3-methylsulphonylpropoxy, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(pyrrolidin-1-yl)-1-hexynyl, 6-(piperidino)-1-hexynyl, 6-(morpholino)-1-hexynyl, 6-(4-methylpiperazin-1-yl)-1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, or m is 2 and the $R^1$ groups are located at the 6- the 7-positions, one $R^1$ group is located at the 6- or 7-position and is selected from the group defined immediately hereinbefore and the other $R^1$ group is a methoxy group;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is an optionally substituted group selected from allyl, 2-propynyl, cyclopropyl, cyclobutyl, cyclopentyl and cyclohexyl, or $R^6$ is a substituted methyl, ethyl, propyl or butyl group, and wherein adjacent carbon atoms in any (2-6C)alkylene chain within a $R^6$ group are optionally separated by the insertion into the chain of a group selected from O, NH, CH=CH and C≡C, and wherein any $CH_2$ or $CH_3$ group within a $R^6$ group optionally bears on each said $CH_2$ or $CH_3$ group one or more of the following substituents, provided that the $R^6$ group when it is a methyl, ethyl, propyl or butyl group must bear at least one such substituent, one, two or three fluoro substituents or a substituent selected from hydroxy, cyano, amidino, amino, carboxy, methoxy, methylthio, methylsulphinyl, methylsulphonyl, methylamino, dimethylamino, methoxycarbonyl, ethoxycarbonyl, propoxycarbonyl, tert-butoxycarbonyl, acetamido, phenyl, cyclopropyl, cyclobutyl, cyclopentyl, cyclohexyl, 1-imidazolyl, 2-imidazolyl, 4-imidazolyl, 2-pyridyl, 3-pyridyl, 4-pyridyl, tetrahydrofuran-2-yl, pyrrolidin-1-yl, 1,4-dioxan-2-yl, morpholino, piperidino, piperazin-1-yl, homopiperidin-1-yl and homopiperazin-1-yl, and wherein any phenyl, imidazolyl, pyridyl or heterocyclyl group within a $R^6$ group optionally bears 1 or 2 substituents, which may be the same or different, selected from fluoro, chloro, trifluoromethyl, hydroxy, amino, carbamoyl, methyl, ethyl and methoxy, and wherein any heterocyclyl group within a $R^6$ group optionally bears 1 or 2 oxo substituents; ps or a pharmaceutically-acceptable acid-addition salt thereof.

A further preferred compound of the invention is a quinazoline derivative of the Formula II wherein:

m is 1 and the $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclopropylmethoxy, 3-methylsulphonylpropoxy and 2-[N-(2-methoxyethyl)-N-methylamino]ethoxy;

or m is 2 and one $R^1$ group is located at the 7-position and is selected from the groups defined immediately hereinbefore and the other $R^1$ group is a 6-methoxy group;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl which bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is allyl, 2-propynyl, cyclopropyl, cyclopropylmethyl, cyclobutyl, cyclopentyl or 4-hydroxycyclohexyl, or $R^6$ is a substituted methyl, ethyl, propyl or butyl group, and wherein adjacent carbon atoms in any propyl or butyl group are optionally separated by the insertion into the chain of an O group, and wherein any $CH_2$ or $CH_3$ group within a $R^6$ group when it is a methyl, ethyl, propyl or butyl group bears one, two or three fluoro substituents or a substituent selected from hydroxy, cyano, amidino, amino, carboxy, methoxy, methylthio, methylsulphinyl, methylsulphonyl, methylamino, dimethylamino, methoxycarbonyl, ethoxycarbonyl, propoxycarbonyl, tert-butoxycarbonyl, acetamido, phenyl, cyclopropyl, 4-imidazolyl, 2-pyridyl, tetrahydrofuran-2-yl, pyrrolidin-1-yl, 2-oxo-pyrrolidin-1-yl, 1,4-dioxan-2-yl, morpholino, piperidino and piperazin-1-yl, and wherein any phenyl, imidazolyl, pyridyl or heterocyclyl group within a $R^6$ group optionally bears 1 or 2 substituents, which may be the same or different, selected from fluoro, chloro, trifluoromethyl, hydroxy, methyl, ethyl and methoxy;

or a pharmaceutically-acceptable acid-addition salt thereof.

A further preferred compound of the invention is a quinazoline derivative of the Formula II wherein:

m is 2 and one $R^1$ group is a 6-methoxy group and the other $R^1$ group is located at the 7-position and is selected from 2-pyrrolidin-1-ylethoxy, 3-pyrrolidin-1-ylpropoxy, 2-morpholinoethoxy, 3-morpholinopropoxy, 2-piperidinoethoxy, 3-piperidinopropoxy, N-methylpiperidin-4-ylmethoxy, 2-(4-methylpiperazin-1-yl)ethoxy and 3-(4-methylpiperazin-1-yl)propoxy;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl which bears 1, 2 or 3 substituents, which may be the same or different, selected from fluoro, chloro, bromo and trifluoromethyl provided that at least one substituent is located at an ortho position; and $R^6$ is allyl, 2-propynyl, cyclopropyl, cyclopropylmethyl, cyclobutyl, 4-hydroxycyclohexyl, 2,2,2-trifluoromethyl, 2,3-dihydroxypropyl, 2-aminoethyl, 3-aminopropyl, 2-dimethylaminoethyl, 3-dimethylaminopropyl, 2-hydroxyethyl, 3-hydroxypropyl, 2-methoxyethyl, 3-methoxypropyl, 2-methylthioethyl, 3-methyliopropyl, 2-methylsulphonylethyl, 3-methylsulphonylpropyl, 2-(2-hydroxyethoxy)ethyl, 2-cyanoethyl, 2-amidinoethyl, carboxymethyl, 2-carboxyethyl, methoxycarbonylmethyl, 2-methoxycarbonylethyl, tert-butoxycarbonylmethyl, 2-(tert-butoxycarbonyl)ethyl, benzyl, 2,6-difluorobenzyl, phenethyl, 2-imidazol-4-ylethyl 2-pyrid-2-ylethyl, tetrahydrofuran-2-ylmethyl, 1,4-dioxan-2-ylmethyl, 2-pyrrolidin-1-ylethyl, 2-(2-oxopyrrolidin-1-yl)ethyl, 3-pyrrolidin1-ylpropyl, 3-(2-oxopyrrolidin-1-yl)propyl, 2-morpholinoethyl, 3-morpholinopropyl, 2-piperidinoethyl, 3-piperidinopropyl, 2-(4-methylpiperazin-1-yl)ethyl, 3-(4-methylpiperazin-1-yl)propyl, N-methylpiperidin-3-ylmethyl or N-methylpiperidin-4-ylmethyl; or a pharmaceutically-acceptable acid-addition salt thereof.

A preferred compound of the invention is a quinazoline derivative of the Formula II wherein:

m is 1 and the $R^1$ group is located at the 6- or 7-position and is selected from hydroxy, methoxy, benzyloxy, cyclopropylmethoxy, 2-dimethylaminoethoxy, 2-diethylaminoethoxy, 3-dimethylaminopropoxy, 3-diethylaminopropoxy, 2-(2-methoxyethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 2-(2-oxoimidazolidin-1-yl)ethoxy, 2-morpholinylmethoxy, 3-morpholinylmethoxy, 2-morpholinoethoxy, 3-morpholinopropoxy, 2-(1,1-dioxotetrahydro-4H-1,4-thiazin-4-yl)ethoxy, 3-(1,1- dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, N-(2-methoxyethyl)piperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1-yl)propoxy, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 2-methylsulphonylethoxy, 3-methylsulphonylpropoxy, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(pyrrolidin-1-yl)-1-hexynyl, 6-(piperidino)-1-hexynyl, 6-(morpholino)-1-hexynyl, 6-(4-methylpiperazin-1-yl)-1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, or m is 2 and the $R^1$ groups are located at the 6- the 7-positions, one $R^1$ group is located at the 6- or 7-position and is selected from the groups defined immediately hereinbefore and the other $R^1$ is a methoxy group;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is an optionally substituted group selected from allyl, 2-propynyl, cyclopropyl, cyclobutyl, cyclopentyl and cyclohexyl, or $R^6$ is a substituted methyl, ethyl, propyl or butyl group, and wherein adjacent carbon atoms in any (2-6C)alkylene chain within a $R^6$ group are optionally separated by the insertion into the chain of a group selected from O, NH, CH=CH and C≡C, and wherein any $CH_2$ or $CH_3$ group within a $R^6$ group optionally bears on each said $CH_2$ or $CH_3$ group one or more of the following substituents, provided that the $R^6$ group when it is a methyl, ethyl, propyl or butyl group must bear at least one such substituent, one, two or three fluoro substituents or a substituent selected from hydroxy, cyano, amidino, amino, carboxy, methoxy, ethoxy, methylthio, methylsulphinyl, methylsulphonyl, methylamino, ethylamino, isopropylamino, dimethylamino, methoxycarbonyl, ethoxycarbonyl, propoxycarbonyl, tert-butoxycarbonyl, N-methylcarbamoyl, N-ethylcarbamoyl, N-isopropylcarbamoyl, N-tert-butylcarbamoyl, acetamido, phenyl, cyclopropyl, cyclobutyl, cyclopentyl, cyclohexyl, cyclohexenyl, 2-furyl, 2-thienyl, 1-imidazolyl, 2-imidazolyl, 4-imidazolyl, 2-pyridyl, 3-pyridyl, 4-pyridyl, tetrahydrofuran-2-yl, pyrrolidin-1-yl, pyrrolidin-2-yl, 1,4-dioxan-2-yl, morpholino, piperidino, piperidin-2-yl, piperazin-1-yl, homopiperidin-1-yl and homopiperazin-1-yl, and wherein any phenyl, heteroaryl or heterocyclyl group within a $R^6$ group optionally bears 1 or 2 substituents, which may be the same or different, selected from fluoro, chloro, trifluoromethyl, hydroxy, amino, carbamoyl, methyl, ethyl and methoxy, and wherein any heterocyclyl group within a $R^6$ group optionally bears 1 or 2 oxo substituents;

or a pharmaceutically-acceptable acid-addition salt thereof.

A further preferred compound of the invention is a quinazoline derivative of the Formula II wherein:

m is 1 and the $R^1$ group is located at the 6- or 7-position and is selected from 2-(2-methoxyethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, N-methylpyrrolidin-3-yloxy, 2-pyrrolidin-1-ylethoxy, 3-pyrrolidin-1-ylpropoxy, 3-morpholinylmethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, N-(2-methoxyethyl)piperidin-4-ylmethoxy, (2-(4-methylpiperazin-1-yl)ethoxy, 3-(4-methylpiperazin-1-yl)propoxy, benzyloxy, cyclopropylmethoxy, 3-methylsulphonylpropoxy and 2-[N-(2-methoxyethyl)-N-methylamino]ethoxy;

or m is 1 and one $R^1$ group is located at the 7-position and is selected from the groups defined immediately hereinbefore and the other $R^1$ group is a 6-methoxy group;

or m is 2 and one $R^1$ group is located at the 6-position and is selected from the groups defined immediately hereinbefore and the other $R^1$ group is a 7-methoxy group;

each of $R^2$, $R^3$ and $R^5$ is hydrogen except that one of the pairs of groups $R^2$ and $R^4$ together, $R^3$ and $R^4$ together and $R^5$ and $R^6$ together forms a bond;

$Q^2$ is phenyl which bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is allyl, 2-propynyl, cyclopropyl, cyclopropylmethyl, cyclobutyl, cyclopentyl or 4-hydroxycyclohexyl, or $R^6$ is a substituted methyl, ethyl, propyl or butyl group, and wherein adjacent carbon atoms in any propyl or butyl group are optionally separated by the insertion into the chain of an O group, and wherein any $CH_2$ or $CH_3$ group within a $R^6$ group when it is a methyl, ethyl, propyl or butyl group bears one, two or three fluoro substituents or a substituent selected from hydroxy, cyano, amidino, amino, carboxy, methoxy, ethoxy, methylthio, methylsulphinyl, methylsulphonyl, methylamino, ethylamino, isopropylamino, dimethylamino, methoxycarbonyl, ethoxycarbonyl, propoxycarbonyl, tert-butoxycarbonyl, N-methylcarbamoyl, N-ethylcarbamoyl, N-isopropylcarbamoyl, N-tert-butylcarbamoyl, acetamido, phenyl, cyclopropyl, 2-furyl, 2-thienyl, 4-imidazolyl, 2-pyridyl, 3-pyridyl, 4-pyridyl, tetrahydrofuran-2-yl, pyrrolidin-1-yl, pyrrolidin-2-yl, 2-oxopyrrolidin-1-yl, 1,4-dioxan-2-yl, morpholino, piperidin-2-yl and piperazin-1-yl, and wherein any phenyl, heteroaryl or heterocyclyl group within a $R^6$ group optionally bears 1 or 2 substituents, which may be the same or different, selected from fluoro, chloro, trifluoromethyl, hydroxy, methyl, ethyl and methoxy;

or a pharmaceutically-acceptable acid-addition salt thereof.

A further preferred compound of the invention is a quinazoline derivative of the Formula II wherein:

m is 2 and one $R^1$ group is a 6-methoxy group and the other $R^1$ group is located at the 7-position and is selected from 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-piperidinoethoxy, 3-piperidinopropoxy, N-methylpiperidin-4-ylmethoxy, N-(2-methoxyethyl)piperidin-4-ylmethoxy, 2-(4-methylpiperazin-1-yl)ethoxy and 3-(4-methylpiperazin-1-yl)propoxy;

each of $R^2$, $R^3$ and $R^5$ is hydrogen except that one of the pairs of groups $R^3$ and $R^4$ together, $R^3$ and $R^4$ together and $R^5$ and $R^4$ together forms a bond;

$Q^2$ is phenyl which bears 1, 2 or 3 substituents, which may be the same or different, selected from fluoro, chloro, bromo and methyl provided that at least one substituent is located at an ortho position; and $R^6$ is allyl, 2-propynyl, cyclopropyl, cyclopropylmethyl, cyclobutyl, 4-hydroxycyclohexyl, 2,2,2-trifluoroethyl, 2,3-dihydroxypropyl, 2-aminoethyl, 3-aminopropyl, 2-methylaminoethyl, 3-methylaminopropyl, 2-dimethylaminoethyl, 3-dimethylaminopropyl, 2-hydroxyethyl, 3-hydroxypropyl, 2-methoxyethyl, 3-methoxypropyl, 2-methylthioethyl, 3-methylthiopropyl, 2-methylsulphonylethyl, 3-methylsulphonylpropyl, 2-(2-hydroxyethoxy)ethyl, 2-cyanoethyl, 5-cyanopentyl, 2-amidinoethyl, carboxymethyl, 2-carboxyethyl, methoxycarbonylmethyl, 2-methoxycarbonylethyl, tert-butoxycarbonylmethyl, 2-(tert-butoxycarbonyl)ethyl, N-methylcarbamoylmethyl, N-isopropylcarbamoylmethyl, N-tert-butylcarbamoylmethyl, benzyl, 2-fluorobenzyl, 3-fluorobenzyl, 2,6-difluorobenzyl, phenethyl, 2-furylmethyl, 2-thienylmethyl, 2-imidazol-4-ylethyl, 2-pyridylmethyl, 3-pyridylmethyl, 4-pyridylmethyl, 2-pyrid-2-ylethyl, tetrahydrofuran-2-ylmethyl, 1,4-dioxan-2-ylmethyl, 2-pyrrolidin-1-ylethyl, 2-(2-oxopyrrolidin-1-yl)ethyl, 2-(N-methylpyrrolidin-2-yl)ethyl, 3-pyrrolidin-1-ylpropyl, 3-(2-oxopyrrolidin-1-yl)propyl, 2-morpholinoethyl, 3-morpholinopropyl, 2-piperidinoethyl, 3-piperidinopropyl, 2-(4-methylpiperazin-1-yl)ethyl, 3-(4-methylpiperazin-1-yl)propyl, N-methylpiperidin-3-ylmethyl or N-methylpiperidin-4-ylmethyl;

or a pharmaceutically-acceptable acid-addition salt thereof.

A particular preferred compound of the invention is, for example, a quinazoline derivative of the Formula II selected from:—

N-(2-chloro-6-methylphenyl)-N'-(2-hydroxyethyl)-N"-[6-methoxy-7-(N-methylpiperidin-4-ylmethoxy)quinazolin-4-yl]guanidine, N-allyl-N'-(2-chloro-6-methylphenyl)-N"-[6-methoxy-7-(3-pyrrolidin-1-ylpropoxy)quinazolin-4-yl] guanidine, N-allyl-N'-(2,6-dimethylphenyl)-N"-[6-methoxy-7-(N-methylpiperidin-4-ylmethoxy)quinazolin-4-yl]guanidine, and N-(2-chloro-6-methylphenyl)-N'-[6-methoxy-7-(N-methylpiperidin-4-ylmethoxy)quinazolin-4-yl]-N"-(2-propynyl)guanidine;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, $Q^1$, $R^2$, $R^3$, $R^4$, $R^5$, $R^6$ and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

A quinazoline derivative of the Formula I, or a pharmaceutically-acceptable salt thereof, may be prepared by:—

(a) the reaction, conveniently in the presence of a suitable metallic salt catalyst, of a thiourea of the Formula VI

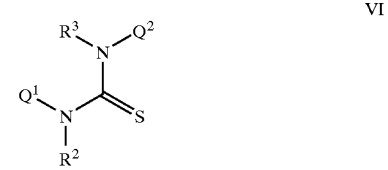

wherein $Q^1$, $R^2$, $Q^2$ and $R^3$ have any of the meaning defined hereinbefore except that any functional group is protected if necessary, with an amine of the Formula VII

wherein $R^5$ and $R^6$ have any of the meanings defined hereinbefore except that any functional group is protected if necessary, whereafter any protecting group that is present is removed by conventional means.

A suitable metallic salt catalyst is, for example, a mercuric salt such as mercuric(II) oxide and the reaction is conveniently carried out in the presence of a suitable inert solvent or diluent, for example a halogenated solvent such as methylene chloride, chloroform or carbon tetrachloride, an ether such as tetrahydrofuran or 1,4-dioxan, or a dipolar aprotic solvent such as acetonitrile, N,N-dimethylformamide, N,N-dimethylacetamide, N-methylpyrrolidin-2-one or dimethylsulphoxide. The reaction is conveniently carried out at a temperature in the range, for example, 10 to 150° C., preferably at or near ambient temperature.

As stated hereinbefore, the compounds of Formula I defined above may exhibit the phenomenon of tautomerism. In particular, tautomerism may affect the guanidino group formed when one of the pairs of groups $R^2$ and $R^4$ together, $R^3$ and $R^4$ together and $R^5$ and $R^4$ together forms a bond. The generic structure of Formula I produced by process variant (a) may therefore give rise to the three structures.

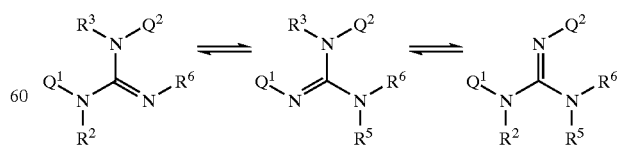

Protecting groups may in general be chosen from any of the groups described in the literature or known to the skilled chemist as appropriate for the protection of the group in question and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1-12C) alkyl groups (for example isopropyl and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6)alkenyl groups (for example allyl). Methods particularly appropriate for the removal of carboxyl protecting groups include for example, acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxyenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such a benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

A thiourea of the Formula VI, wherein $R^3$ is hydrogen, may be prepared by the reaction, conveniently in the presence of a suitable base, of an amine of the Formula VIII

$$Q^1\text{—}NHR^2 \qquad\qquad VIII$$

wherein $Q^1$ and $R^2$ have any of the meanings defined hereinbefore except that any functional group is protected if necessary, with an isothiocyanate of the Formula IX, or a conventional chemical equivalent thereof or a conventional chemical precursor thereof,

$$S\text{=}C\text{=}N\text{—}Q^2 \qquad\qquad IX$$

wherein $Q^2$ has any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate, alkoxide or hydroxide, for example sodium carbonate, potassium carbonate, calcium carbonate, sodium ethoxide, potassium tert-butoxide, sodium hydroxide or potassium hydroxide, or, for example, an alkali metal hydride, for example sodium hydride or potassium hydride, or an organometallic base such as an alkyl-lithium, for example, n-butyl-lithium or a dialkylamino-lithium, for example lithium di-isopropylamide.

A suitable conventional chemical equivalent of an isothiocyanate of the Formula IX is, for example, a compound of the Formula X

$$L\text{—}CS\text{—}NH\text{—}Q^2 \qquad\qquad X$$

wherein $Q^2$ has any of the meanings defined hereinbefore except that any functional group is protected if necessary, and L is a suitable displaceable group. On treatment with a suitable base as defined hereinbefore, the compound of the Formula X reacts to form the desired isothiocyanate of the Formula IX.

A suitable displaceable or leaving group L is, for example, a halogeno, alkoxy, aryloxy or sulphonyloxy group, for example a chloro, bromo, methoxy, phenoxy, methanesulphonyloxy or toluene-4-sulphonyloxy group.

A suitable conventional chemical precursor of an isothiocyanate of the Formula IX is, for example, an acyl azide of the Formula IX

$$N_3\text{—}CS\text{—}Q^2 \qquad\qquad XI$$

wherein $Q^2$ has any of the meanings defined hereinbefore except that any functional group is protected if necessary. On thermal or photolytic treatment the thioacyl azide of the Formula XI decomposes and rearranges to form the desired isothiocyanate of the Formula IX.

When L is, for example, a chloro group, the compound of the Formula X may be prepared by, for example, the reaction, conveniently in the presence of a suitable base as defined hereinbefore, of thiophosgene with an amino of the Formula XII.

$H_2N-Q^2$  XII

The compound of the Formula XI may be prepared by, for example, the reaction of a metal azide such as sodium azide with a compound of the Formula XIII.

$L-C-Q^2$  XIII

A thiourea of the Formula VI, wherein $R^2$ is hydrogen, may be prepared by the reaction, conveniently in the presence of a suitable base as defined hereinbefore, of an amine of the Formula XIV

$R^3NH-Q^2$  XIV wherein $Q^2$ and $R^3$ have any of the meanings defined hereinbefore except that any functional group is protected if necessary, with an isothiocyanate of the Formula XV, or a conventional chemical equivalent thereof or a conventional chemical precursor thereof, $Q^1-N=C=S$  XV wherein $Q^1$ has any of the meanings defined hereinbefore except that any functional group is protected if necessary, whereafter any protecting group that is present is removed by conventional means.

A suitable conventional chemical equivalent of an isothiocyanate of the Formula XV is, for example, a compound of the Formula XVI

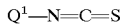
$Q^1-NH-CS-L$  XVI wherein $Q^1$ has any of the meanings defined hereinbefore except that any functional group is protected if necessary, and L is a suitable displaceable group as defined hereinbefore. On treatment with a suitable base as defined hereinbefore, the compound of the Formula XVI reacts to form the desired isothiocyanate of the Formula XV.

A suitable conventional chemical precursor of an isothiocyanate of the Formula XV is, for example, an acyl azide of the Formula XVII

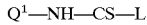
$Q^1-CS-N_3$  XVII wherein $Q^1$ has any of the meanings defined hereinbefore except that any functional group is protected if necessary. On thermal or photolytic treatment the thioacyl azide of the Formula XVII decomposes and rearranges to form the desired isothiocyanate of the Formula XV.

When L is, for example, a chloro group, the compound of the Formula XVII may be prepared by, for example, the reaction, conveniently in the presence of a suitable base as defined hereinbefore, of thiophosgene with an amine of the Formula XVIII.

$Q^1-NH_2$  XVIII

The compound of the Formula XVII may be prepared by, for example, the reaction of a metal azide such as sodium azide with a compound of the Formula XIX.

$Q^1-CS-L$  XIX (b) For the production of those compounds of the Formula I wherein $Q^1$, $R^6$ or $Q^2$ contains a carboxy group, the cleavage of the corresponding compound of Formula I wherein $Q^1$, $R^6$ or $Q^2$ contains a protected carboxy group.

Suitable protecting groups for a carboxy are, for example, any such protecting group disclosed hereinbefore. Suitable methods for the cleavage of such carboxy protecting groups are also disclosed hereinbefore. In particular, a suitable protecting group is a lower alkoxy ester such as a tert-butoxy ester which may be cleaved under conventional reaction conditions such as under acid-catalysed hydrolysis, for example in the presence of trifluoroacetic acid.

(c) For those compounds of the Formula I wherein $R^6$ or a substituent on $Q^1$ or $Q^2$ contains an alkylcarbamoyl group or a substituted alkylcarbamoyl group, the reaction of the corresponding compound of Formula I wherein $R^6$ or a substituent on $Q^1$ or $Q^2$ is carboxy group, or a reactive derivative thereof, with an amine or substituted amine as appropriate.

A suitable reactive derivative of a compound of Formula I wherein $R^6$ or a substituent on $Q^1$ or $Q^2$ contains a carboxy group is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester formed by the reaction of the acid and an ester such as pentafluorophenyl trifluoroacetate or an ester formed by the reaction of the acid and an alcohol such as N-hydroxybenzotriazole; and acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide or 1-(3-dimethylaminopropyl)-3-ethylcarbodiimide.

The reaction is conveniently carried out in the presence of a suitable base as define hereinbefore and in the presence of a suitable inert solvent or diluent as defined hereinbefore.

Typically is carbodiimide coupling reagent is used in the presence of an organic solvent (preferably an anhydrous polar aprotic organic solvent) at a non-extreme temperature, for example in the region −10 to 40° C., typically at ambient temperature of about 20° C.

A compound of Formula I wherein $R^6$ or a substituent on $Q^1$ or $Q^2$ contains a carboxy group may conveniently be prepared by the cleavage of the corresponding ester such as a (1-12C)alkyl ester, for example by acid-, base- metal- or enzymatically-catalysed cleavage.

(d) For those compounds of the Formula I wherein a substituent on $Q^1$ of $Q^2$ contains an amino-(1-6C)alkyl group or $R^6$ is an amino-(1-6C)alkyl group, the cleavage of the corresponding compound of Formula I wherein a substituent on $Q^1$ or $Q^2$ is a protected amino-(1-6C)alkyl group or $R^6$ is a protected amino-(1-6C)alkyl group as appropriate.

Suitable protecting groups for an amino-(1-6C)alkyl group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis.

(e) For those compounds of the Formula I wherein a substituent on $Q^1$ or $Q^2$ contains an amino group, the reduction of a corresponding compound of Formula I wherein a substituent on $Q^1$ or $Q^2$ contains a nitro group.

Typical reaction conditions include the use of ammonium formate or hydrogen gas in the presence of a catalyst, for example a metallic catalyst such as palladium-onto-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

(f) For the production of those compounds of the Formula I wherein $Q^1$ contains a $R^1$ group in a quinazoline-like ring of the formula Ia, Ib, Ic, or Id that is linked via an oxygen atom, the alkylation of the corresponding compound of Formula I wherein the $R^1$ group in $Q^1$ is a hydroxy group.

The alkylation reaction may, for example, comprise the coupling of a hydroxy-substituted quinazoline-like ring of the formula Ia, Ib, Ic or Id with an alcohol. The reaction may conveniently be carried out in the presence of a suitable dehydrating agent.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate or 1,1'-(azodicarbonyl)dipiperdine and a phosphine such as triphenylphosphine or tributylphosphine. The reaction is conveniently carried out in the presence of a suitable insert solvent or diluent, for example tetrahydrofuran or a halogenated solvent such as methylene chloride, chloroform, or carbon tetrachloride and at a temperature in the range, for example, 10 to 150° C., preferably at or near ambient temperature.

Alternatively, the alkylation reaction may comprise the reaction of a hydroxy-substituted quinazoline-like ring of the formula Ia, Ib, Ic or Id or Id with a suitable alkylating agent. The reaction may conveniently be carried out in the presence of a suitable base as defined hereinbefore.

A suitable alkylating agent is, for example, a compound which contains a suitable displaceable group, for example, a halogeno, alkoxy, aryloxy or sulphonyloxy group, for example a chloro, bromo, methoxy, phenoxy, pentafluorophenoxy, methansulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, and ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 40 to 80° C.

When a pharmaceutically-acceptable salt of a quinazoline derivative of the Formula I is required, for example an acid-addition salt, it may be obtained by, for example, reaction of said quinzoline derivative with a suitable acid using a conventional procedure.

Biological Assays

The following assays can be used to measure the effects of the compounds of the present invention as $p56^{lck}$ inhibitors, as inhibitors of T cell activation, as inhibitors of cytokine production in mice and as inhibitors of transplant rejection.

(a) In vitro enzyme assay

The ability of test compounds to inhibit phosphorylation by the enzyme $p56^{lck}$ of a tyrosine-containing polypeptide substrate was assessed using a conventional Elisa assay.

The following conventional procedure was used to obtain $p6^{lck}$ enzyme. An EcoR1/Not1 fragment containing the entire coding sequence of $p56^{lck}$ was generated by the technique of polymerase chain reaction (PCR) from INcyte clone No. 2829606. A 6-His tag was added to the sequence of the N-terminus during the PCR stage. Conventional sequence analysis identified a number of changes compared to the published sequence and these were found also to have been present in the original Incyte template. To achieve expression of the enzyme, the PCR fragment was inserted downstream of the polyhedrin promoter of pFASTBAC1 (Life Technologies Limited, Paisley, UK, Catalogue No. 10360-104). A recombinant Baculovirus was constructed using the Bac-to-Bac (Life Technologies Limited). High Five insect cells (Invitrogen BV, PO Box 2312, 9704 CH Groningen, The Netherlands, Catalogue No. B855-02) were infected with the recombinant Baculovirus at a multiplicity of infection of 1 and incubated for 48 hours. The cells were harvested. Groups of $1.6 \times 10^9$ cells were lysed by incubation in 20 mM Hepes pH7.5 buffer containing 10% glycerol, 1% Triton-X-100, magnesium chloride (1.5 mM), ethylene glycol bis(2-aminoethyl ether N,N,N',N'-tetraacetic acid) (EGTA, 1 mM), sodium vanadate (1 mM), sodium fluoride (10 mM), imidazole (5 mM), sodium chloride (150 mM), phenylmethanesulphonyl fluoride (0.1 mM), pepstatin (1 mg/ml) and leupeptin (1 mg/ml). A soluble fraction was obtained by centrifugation and 6-His-$p56^{lck}$ was purified by column chromatography on a 1 ml Ni-NTA agarose column (Qiagen Limited, Crawley, West Sussex, UK). The protein was eluted using the above-mentioned buffer except that imidazole (100 mM) was also present. The $p56^{lck}$ enzyme are obtained was stored at $-80°$ C.

Substrate solution [100 $\mu$l of a 2 $\mu$g/ml solution of the polyamino acid Poly(Glu, Ala, Tyr) 6:3:1 (Sigma Catalogue No. P3899) in phosphate buffered saline (PBS)] was added to each well of a Nunc 96-well immunoplate (Catalogue No. 439454) and the plate was sealed and stored at 4° C. for 16 hours. The excess of substrate solution was discarded, the substrate-coated wells were washed with Hepes pH7.4 buffer (50 mM, 300 $\mu$l) and blotted dry. Each test compound was dissolved in DMSO and diluted to give a series of dilutions (from 100 $\mu$M to 0.001 $\mu$M) of the compound in a 10:1 mixture of water and DMSO. Portions (25 $\mu$l) of each dilution of test compound were transferred to the 96-well assay plate. Aliquots (25 $\mu$l) of a 10:1 mixture of water and DMSO were added followed by aliquots (25 $\mu$l) of a mixture of adenosine triphosphate (ATP; 24 $\mu$l of a 1 mM aqueous solution) and manganese chloride (3 ml of a 40 mM aqueous solution).

$P56^{lck}$ enzyme (0.3 $\mu$l of a 0.5 mg/ml stock solution) was diluted in a mixture of Hepes pH 7.4 buffer (200 mM, 3 ml), sodium orthovanadate (2 mM, 0.6 ml), 2% Triton X-100 (0.6 ml), dithiothreitol (25 mM, 48 $\mu$l) and distilled water (1.8 ml). Aliquots (50 $\mu$l) of the resultant solution were transferred to each well in the assay plate and the plate was incubated at ambient temperature for 8 minutes. The wells were washed sequentially with two aliquots (300 $\mu$l) of phosphate-buffered saline (PBS) containing 0.1% Tween 20 (hereinafter PBS/T).

Aliquots (100 $\mu$l) were added to each well of a mixture of antiphosphotyrosine-4G10 monoclonal IgG2bk antibody (UBI Catalogue No. 05-321; 30 $\mu$l of a 50 $\mu$g/ml solution of the antibody in PBS/T). PBS/T (11 ml) and bovine serum albumin (BSA; Sigma Catalogue No. A6793; 55 mg) and the plate was incubated at ambient temperature for 1 hour. The wells were washed sequentially with two aliquots (300 μl) of PBS/T and blotted dry. Aliquots (100 μl) were added to each well of a mixture of sheep anti-mouse IgG-peroxidase antibody (Amersham Catalogue No. NXA931; 20 μl), PBS/T (11 ml) and BSA (55 mg) and the plate was incubated at ambient temperature for 1 hours. The wells were washed sequentially with two aliquots (300 μl) of PBST/T and blotted dry.

Aliquots (100 μl) were added to each well of an ABTS solution [prepared by adding an 2,2'-azinobis(3-ethylbenzothiazolinesulphonic acid) (ABTS) tablet (50 mg; Boehringer Catalogue No. 1204521) to a mixture (50 mM) of phosphate-citrate pH5.0 buffer and 0.03% sodium perborate (obtained by adding a PCSB capsule (Sigma Catalogue No. P-4922) to distilled water (100 ml))]. The plate was incubated at ambient temperature for 1.5 hours and the absorbance at 405 nm was determined.

The extent of inhibition of the phosphorylation reaction at a range of concentration of each test compound was determined and an $IC_{50}$ value was calculated.

(b) In vitro T cell proliferation assays

The ability of test compounds to inhibit T cell proliferation was assessed by using human peripheral blood mononuclear cells and stimulation of the T cells by way of the T cell receptor or other than by way of the T cell receptor.

Peripheral blood mononuclear cells (PBMC) were isolated from heparinised (10 units/ml heparin) human blood by density centrifugation (Lymphoprep™; Nycomed) spinning initially at 2000 rpm at ambient temperature for 20 minutes. Cells at the interphase were transferred to clean tubes, diluted 1:1 with RPMI 1640 medium (Gibco) and spun at 2000 rpm at ambient temperature for 10 minutes. The cell pellet was resuspended in RPMI 1640 medium and spun at 1400 rpm at ambient temperature for 10 minutes. The cell pellet was resuspended in RPMI 1640 medium and spun at 900 rpm at ambient temperature for 10 minutes to remove platelets. The prepared mononuclear cells were resuspended in an assay medium comprising RPMI 1640 culture medium supplemented with 50 units/ml penicillin, 50 μg/ml streptomycin, 1 mM glutamine and 10% heat-inactivated human AB serum.

Test compounds were solubilised in DMSO at a concentration of 10 mM and diluted 1:83.3 in assay medium. Aliquots (75 μl) were added to each well of a 96 well flat-bottomed tissue culture plate and subsequently serial 1 to 3 dilutions were made into assay medium giving final test concentrations in the range 0.1 to 30 μM. Control wells contained assay medium (50 μl) containing 1.2% DMSO. PBMCs (100 μl of a suspension of $2\times10^6$ cells/ml in assay medium) were added to each well and incubated for 1 hour at 37° C. in a humidified (5% $CO_2$/95% air) incubator.

The extent of inhibition of T cell proliferation at a range of concentrations of each test compound was determined and an $IC_{50}$ value was calculated.

(b)(i) T cell receptor stimulation

Aliquots (50 μl) of the T cell receptor stimulatory anti-CD3 antibody (Pharmingen Catalogue No. 30100D; 40 ng/ml in assay medium) were added to each well and the cells were incubated for 24 hours at 37° C. in a humidified (5%$CO_2$/95% air) incubator. Tritiated thymidine (1 μCi per well) was added and the cells were incubated for up to a further 24 hours at 37° C. The cells were harvested onto a filter mat and radioactivity was counted using a Wallac 1450 Microbeta Plus liquid scintillation counter.

(b)(ii) Non T cell receptor stimulation

Aliquots (50 μl) of a mixture of the cell stimulants PMA (phorbol-12-myristate-13-acetate, Sigma Catalogue No. P8139; 40 ng/ml) and Ionomycin (Sigma Catalogue No. I0684; 1.2 μM) were added to each well and the cells were incubated and analysed as described in paragraph (b)(i).

(c) In vivo skin graft rejection test

The ability of test compounds to inhibit rodent skin allograft rejection was assessed using analogous procedures to those disclosed by J. Magae et al., *Cellular Immunology*, 1996, 173, 276–281 and R. Tsuji et al., *J. Antibiot.*, 1992, 45, 1295 to assess the effect of cyclosporin A on T cell properties in vivo.

(d) Test as anti-arthritic agent

Activity of a test compound as an anti-arthritic agent was assessed as follows. Acid soluble native type II collagen has been shown to be arthritogenic in rats causing polyarthritis when administered in Freunds incomplete adjuvant by (D. E. Trentham et al. *J. Exp. Med.*, 1977, 146, 857). This is now known as collagen-induced arthritis (CIA) and similar conditions can be induced in mice and primates. CIA in DBA/1 mice as described by R. O. Williams et al., *Proc Natl. Acad Sci.*, 1992, 89, 9784 and *Immunology*, 1995, 84, 433 is a tertiary model which can be used to demonstrate the anti-arthritic activity of a test compound.

Although the pharmacological properties of the compounds of the Formula I vary with structural change as expected, in general activity possessed by compounds of the Formula I, including those compounds excluded by way of one of the provisos in the definition hereinbefore, may be demonstrated at the following concentrations or doses in one or more of the above tests (a), (b), (c) and (d):—

| | |
|---|---|
| Test (a):- | $IC_{50}$ in the range, for example, 0.0001–5 μM; |
| Test (b)(i):- | $IC_{50}$ in the range, for example, 0.001–10 μM; |
| Test (b)(ii):- | $IC_{50}$ in the range, for example, 0.5–>30 μM; |
| Test (c):- | activity in the range, for example, 0.1–100 mg/kg; |
| Test (d):- | activity in the range, for example, 1–100 mg/kg;. |

No physiologically-unacceptable toxicity was observed at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

We have found that the compounds of the present invention are of use in the prevention or treatment of autoimmune diseases or medical conditions, for example T cell mediated disease such as transplant rejection, rheumatoid arthritis or multiple sclerosis. We have further found that these effects are believed to arise by virtue of inhibition of one or more of the multiple tyrosine-specific protein kinases which are involved in the early signal transduction steps which lead to full T cell activation, for example by way of inhibition of the enzyme $p56^{lck}$. Accordingly the compounds of the present invention are expected to be useful in the prevention of treatment of T cell mediated diseases or medical conditions. In particular the compounds of the present invention are expected to be useful in the prevention or treatment of those pathological conditions which are sensitive to inhibition of one or more of the multiple tyrosine-specific protein kinases which are involved in the early signal transduction steps which lead to T cell activation, for example by way of inhibition of $p56^{lck}$ tyrosine kinase. Further, the compounds of the present invention are expected to be useful in the prevention or treatment of those diseases or medical conditions which are mediated alone or in part by inhibition of the enzyme $p56^{lck}$, i.e. the compounds may be used to produce a $p56^{lck}$ enzyme inhibitory effect in a warm-blooded animal in need of such treatment. Specifically, the compounds of the present invention are expected to be useful in the prevention or treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the present invention are expected to be useful in the prevention or treatment of the acute rejection of transplanted tissue or organs.

Thus according to this aspect of the invention there is provided the use of a quinazoline derivative of the Formula I, or a pharmaceutically-acceptable salt thereof, as defined hereinbefore in the manufacture of a medicament for use in the prevention or treatment of T cell mediated diseases or medical conditions in a warm-blooded animal such as man.

According to a further feature of this aspect of the invention there is provided a method for the prevention or treatment of T cell mediated diseases or medical conditions in a warm-blooded animal, such as man, in need of such treatment which comprises administering to said animal an effective amount of a quinazoline derivative of the Formula I, or a pharmaceutically-acceptable salt thereof, as defined hereinbefore.

According to a further feature of the invention there is provided the use of a quinazoline derivative of the Formula I, or a pharmaceutically-acceptable salt thereof, as defined immediately hereinbefore in the manufacture of a medicament for use in the prevention or treatment of those pathological conditions which are sensitive to inhibition of one or more of the multiple tyrosine-specific protein kinases which are involved in the early signal transduction steps which lead to T cell activation.

According to a further of the invention there is provided a method for the prevention or treatment of those pathological conditions which are sensitive to inhibition of one or more of the multiple tyrosine-specific protein kinases which are involved in the early signal transduction steps which lead to T cell activation which comprises administering to said animal an effective amount of a quinazoline derivative of the Formula I, or a pharmaceutically-acceptable salt thereof, as defined immediately hereinbefore.

As stated above the size of the dose required for the therapeutic or prophylactic treatment of T cell mediated disease will necessarily be varied depending on the host treated, the route of administration and the severity of the illness being treated. A unit dose in the range, for example, 0.1 mg/kg to 75 mg/kg body weight, conveniently 0.1 mg/kg to 30 mg/kg body weight, is envisaged, given if required in divided doses.

The compounds of this invention may be used in combinations with other drugs and therapies used in the treatment of T cell mediated disease. For example, the compounds of the Formula I could be used in combination with drugs and therapies used in the treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the Formula I could be used in combination with drugs and therapies such as cyclosporin. A used in the prevention or treatment of the acute rejection of transplanted organs.

For example, the compounds of the Formula I are of value in the treatment of certain inflammatory and non-inflammatory diseases which are currently treated with a cylooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase. The compounds of the invention may also be used with anti-inflammatory agents such as an inhibitor of the enzyme COX-2 such as celecoxib or rofecoxib.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of the T cell activation. Thus, they are useful as pharmacological standards for use in the development of new biological tests and in the search for new pharmacological agents.

The invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art, 9385) or Merck Lichroprep RP-18 (Art. 9303) reversed-phase silica obtained from E. Merck, Darmstadt, Germany of high pressure liquid chromatography (HPLC) was performed on C18 reverse phase silica, for example on a Dynamax C-18 60Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, a Varian Gemini 2000 spectrometer operating at a field strength of 300 MHz or a Bruker AM300 spectrometer operating at a field strength of 300 MHz]; the following abbreviations have been used; s, singlet, d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:—

| DMF | N,N-dimethylformamide |
| DMSO | dimethylsulphoxide |
| THF | tetrahydrofuran |
| NMP | N-methylpyrrolidin-2-one |

EXAMPLE 1

N-(2-chloro-6-methylphenyl)-N'-(2-hydroxyethyl)-N''-[6-methoxy-7-(N-methylpiperidin-4-ylmethoxy)quinazolin-4-yl]guanidine Mercuric(II) oxide (0.107 g) was added to a mixture of 1-(2-chloro-6-methylphenyl)-3-[6-methoxy-7-(N-methylpiperidin-4-ylmethoxy)quinazolin-4-yl]thiourea (0.118 g), 2-aminoethanol (0.03 ml), chloroform (5 ml) and methanol (5 ml) and the resultant mixture was stirred at ambient temperature for 2 hours. The reaction mixture was filtered and the filtrate was evaporated. The residue was purified by column chromatography on silica using increasingly polar mixtures of methylene chloride and a 2M solution of ammonia gas in methanol as eluent. There was thus obtained the title compound (0.128 g); NMR Spectrum: (DMSOd$_6$+CD$_3$CO$_2$D) 1.47–1.62 (m, 2H), 1.85–2.11 (m, 5H), 2.29 (s, 3H), 2.67 (s, 3H), 2.87 (t, 2H), 3.33 (d, 2H), 3.59 (t, 4H), 3.79 (s, 3H), 4.0 (d, 2H), 7.08 (s, 1H), 7.19–7.32 (m, 3H), 7.4 (d, 1H), 8.43 (s, 1H), 10.5 (br s, 1H); Mass Spectrum: M+H$^+$ 513 and 515.

The 1-(2-chloro-6-methylphenyl)-3-[6-methoxy-7-(N-methylpiperidin-4-ylmethoxy)quinazolin-4-yl]thiourea used as a starting material was prepared as follows:—

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxycarbonylpiperidine-4-carboxylate (48 g); NMR Spectrum: (CDCl$_3$) 1.25 (t, 3H), 1.45 (s, 9H), 1.55–1.7 (m, 2H), 1.8–2.0 (d, 2H), 2.35–2.5 (m, 1H), 2.7–2.95 (t, 2H), 3.9–4.1 (br s, 2H), 4.15 (q, 2H).

A solution of the material so obtained in THF (180 ml) was cooled at 0° C. and lithium aluminum hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: ($CDCl_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H).

1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C. The resultant mixture was allowed to warm to ambient temperature and was stirred for 1 hour. Petroleum ether (b.p. 60–80° C., 1L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous solution bicarbonate solution and brine, dried over magnesium sulphate and evaporated. There was the obtained N-tert-butoxycarbonyl-4-(4-toluenesulphonyloxymethyl)piperidine (76.7 g), NMR Spectrum: ($CDCl_3$) 1.0–1.2 (m, 2H), 1.45 (s, 9H), 1.65 (d, 2H), 1.75–1.9 (m, 2H), 2.45 (s, 3H), 2.55–2.75 (m, 2H), 3.85 (d, 1H), 4.0–4.2 (br s, 2H), 7.35 (d, 2H), 7.8 (d, 2H).

A portion (40 g) of the material so obtained was added to a suspension of ethyl 4-hydroxy-3-methoxybenzoate (19.6 g) and potassium carbonate (28 g) in DMF (200 ml) and the resultant mixture was stirred and heated at 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallized from petroleum ether (b.p. 60–80° C.) and the suspension was stored overnight at 5° C. The resultant solid was collected by filtration, washed with petroleum ether and dried under vacuum. There was thus obtained ethyl 4-(N-tert-butoxycarbonylpiperidin-5-ylmethoxy)-3-methoxybenzoate (35 g), m.p. 81–83° C.; NMR Spectrum: ($CDCl_3$) 1.2–1.35 (m, 2H), 1.4 (t, 3H), 1.48 (s, 9H), 1.8–1.9 (d, 2H), 2.0–2.15 (m, 2H), 2.75 (t, 2H), 3.9 (d, 2H), 3.95 (s, 3H), 4.05–4.25 (br s, 2H), 4.35 (q, 2H), 6.85 (d, 1H), 7.55 (s, 1H), 7.65 (d, 1H).

The material so obtained was dissolved in formic acid (35 ml), formaldehyde (12M, 37% in water 35 ml) was added and the mixture was stirred and heated to 95° C. for 3 hours. The resultant mixture was evaporated. The residue was dissolved in methylene chloride and hydrogen chloride (3M solution in diethyl ether; 40 ml) was added. The mixture was diluted with diethyl ether and the mixture was triturated until a solid was formed. The solid was collected, washed with diethyl ether and dried under vacuum overnight at 50° C. There was thus obtained ethyl 3-methoxy-4-(N-methylpiperidin-4-ylmethoxy)benzoate (30.6 g), NMR Spectrum: ($DMSOd_6$) 1.29 (t, 3H), 1.5–1.7 (m, 2H), 1.95 (d, 2H), 2.0–2.15 (br s, 1H), 2.72 (s, 3H), 2.9–3.1 (m, 2H), 3.35–3.5 (br s, 2H), 3.85 (s, 3H), 3.9–4.05 (br s, 2H), 4.3 (q, 2H), 7.1 (d, 1H), 7.48 (s, 1H), 7.6 (d, 1H).

The material so obtained was dissolved in methylene chloride (75 ml) and the solution was cooled in an ice-bath to 0–5° C. Trifluoroacetic acid (37.5 ml) was added followed by the dropwise addition over 15 minutes of a solution of foaming nitric acid (24M; 7.42 ml) in methylene chloride (15 ml). The resultant solution was allowed to warm to ambient temperature and was stirred for 2 hours. Volatile materials were evaporated. The residue was dissolved in methylene chloride (50 ml) and the solution was cooled in an ice-bath to 0–5° C. Diethyl ether was added and the resultant precipitate was collected and dried under vacuum at 50° C. The solid was dissolved in methylene chloride (500 ml) and hydrogen chloride (3M solution in diethyl ether; 30 ml) was added followed by diethyl ether (500 ml). The resultant solid was collected and dried under vacuum at 50° C. There was thus obtained ethyl 5-methoxy-4-(N-methylpiperidin-4-ylmethoxy)-2-nitrobenzoate (28.4 g), NMR Spectrum: ($DMSOd_6$) 1.3 (t, 3H), 1.45–1.65 (m, 2H), 1.75–2.1 (m, 3H), 2.75 (s, 3H), 2.9–3.05 (m, 2H), 3.4–3.5 (d, 2H), 3.95 (s, 3H), 4.05 (d, 2H), 4.3 (q, 2H), 7.32 (s, 1H), 7.66 (s, 1H).

A mixture of a portion (3.89 g) of the material so obtained, 10% platinum-on-activated carbon (50% wet, 0.389 g) and methanol (80 ml) was stirred under 1.8 atmospheres pressure of hydrogen until uptake of hydrogen ceased. The mixture was filtered and the filtrate was evaporated. The residue was dissolved in water (30 ml) and basified to pH10 by the addition of a saturated aqueous sodium bicarbonate solution. The mixture was diluted with a 1:1 mixture of ethyl acetate and diethyl ether and the organic layer was separated. The aqueous layer was further extracted with a 1:1 mixture of ethyl acetate and diethyl ether and the organic extracts were combined, washed in turn with water and brine, dried over magnesium sulphate and evaporated. The residue was triturated under a mixture of petroleum ether (b.p. 60–80° C.) and diethyl ether. The solid so obtained was isolated, washed with petroleum ether and dried under vacuum at 60° C. There was thus obtained ethyl 2-amino-5-methoxy-4-(N-methylpiperidin-4-ylmethoxy)benzoate (2.58 g), m.p. 111–112° C.; NMR Spectrum: ($CDCl_3$) 1.35 (t, 3H), 1.4–1.5 (m, 2H), 1.85 (m, 3H), 1.95 (t, 2H), 2.29 (s, 3H), 2.9 (d, 2H), 3.8 (s, 3H), 3.85 (d, 2H), 4.3 (q, 2H), 5.55 (br s, 2H), 6.13 (s, 1H), 7.33 (s, 1H).

A mixture of ethyl 2-amino-5-methoxy-4-(N-methylpiperidin-4-ylmethoxy)benzoate (16.1 g, formamidine acetic acid salt (5.2 g) and 2-methoxyethyl (160 ml) was stirred and heated at 115° C. for 2 hours. Further formamidine acetic acid salt (10.4 g) was added in portions every 30 minutes during 4 hours and heating was continued for 30 minutes after the last addition. The resultant mixture was evaporated. The solid residue was stirred under a mixture of methylene chloride (50 ml) and ethanol (100 ml). The precipitate was removed by filtration and the filtrate was concentrated to a final volume of 100 ml. The resultant suspension was cooled to 5° C. The solid so obtained was collected, washed with cold ethanol and with diethyl ether and dried under vacuum at 60° C. There was thus obtained 6-methoxy-7-(N-methylpiperidin-4-ylmethoxy)-3,4-dihydroquinazolin-4-one (12.7 g); NMR Spectrum: ($DMSOd_6$) 1.25–1.4 (m, 2H), 1.75 (d, 2H), 1.9 (t, 1H), 1.9 (s, 3H), 2.16 (s, 2H), 2.8 (d, 2H), 3.9 (s, 3H), 4.0 (d, 2H), 7.11 (s, 1H), 7.44 (s, 1H), 7.97 (s, 1H).

A mixture of a portion (2.8 g) of the material so obtained, thionyl chloride (28 ml) and DMF (0.28 ml) was heated to reflux for 1 hour. The mixture was evaporated and the precipitate was triturated under diethyl ether. The resultant solid was isolated and washed with diethyl ether. The solid was then dissolved in methylene chloride and the solution was washed with a saturated aqueous sodium bicarbonate solution. The organic layer was washed in turn with water and brine, dried over magnesium sulphate and evaporated. There was thus obtained 4-chloro-6-methoxy-7-(N-methylpiperidin-4-ylmethoxy)quinazoline (2.9 g), NMR Spectrum: (DMSOd$_6$) 1.3–1.5 (m, 2H), 1.75–1.9 (m, 4H), 2.0 (t, 1H), 2.25 (s, 3H), 2.85 (d, 2H), 4.02 (s, 3H), 4.12 (d, 2H), 7.41 (s, 1H), 8.9 (s, 1H).

A mixture of 4-chloro-6-methoxy-7-(N-methylpiperidin-4-ylmethoxy)quinazoline (11.17 g), 4-bromo-2-fluorophenol (4.57 ml), potassium carbonate (7.19 g) and DMF (110 ml) was stirred and heated at 100° C. for 2.5 hours. The mixture was allowed to cool to ambient temperature and was poured into a mixture (1L) of ice and water. The precipitate was collected, washed with water and dried. The solid was purified by column chromatography on silica using increasingly polar mixtures of methylene chloride, methanol and a 1% aqueous ammonium hydroxide solution (20:1:0 to 10:1:0 to 10:1:1) as eluent. There was thus obtained 4-(4-bromo-2-fluorophenoxy)-6-methoxy-7-(N-methylpiperidin-4-ylmethoxy)quinazoline (13.1 g), NMR Spectrum: (DMSOd$_6$) 1.3–1.4 (m, 2H), 1.7–1.8 (m, 4H), 1.9 (t, 1H), 2.15 (s, 3H), 2.5 (br s, 2H), 4.0 (s, 3H), 4.1 (d, 2H), 7.4 (s, 1H), 7.45–7.6 (m, 3H), 7.8 (d, 1H), 8.5 (s, 1H); Mass Spectrum: M+H$^+$ 476 and 478.

A portion (9.4 g) of the material so obtained was dissolved in a 2M solution of ammonia in isopropanol (150 ml). Liquid ammonia (10 ml) was added and the reaction mixture was sealed in a Carius tube. The reaction mixture was heated to 130° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl-tert-butyl ether. There was thus obtained 4-amino-6-methoxy-7-(N-methylpiperidin-4-ylmethoxy)quinazoline (5.55 g); NMR Spectrum: (DMSOd$_6$) 1.2–1.4 (m, 2H), 1.7–1.8 (m, 4H), 1.85 (t, 1H), 2.1 (s, 3H), 2.8 (d, 2H), 3.8 (s, 3H), 3.9 (d, 2H), 7.0 (s, 1H), 7.3 (br s, 2H), 7.5 (s, 1H), 8.2 (s, 1H); Mass Spectrum: M+H$^+$ 303.

A solution of 4-amino-6-methoxy-7-(N-methylpiperidin-4-ylmethoxy)quinazoline (0.15 g) in DMF (4.5 ml) was added to sodium hydride (60% dispersion in mineral oil, 0.03 g) and the reaction mixture was stirred at ambient temperature for 20 minutes. 2-Chloro-6-methylphenyl isothiocyanate (0.2 g) was added and the mixture was stirred at ambient temperature for 20 hours. The reaction mixture was evaporated and the residual solid was purified by column chromatography on silica using increasingly polar mixtures of methylene chloride and a 2M solution of ammonia in methanol as eluent. There was thus obtained 1-(2-chloro-6-methylphenyl)-3-[6-methoxy-7-(N-methylpiperidin-4-ylmethoxy)quinazolin-4-yl]thiourea (0.12 g); NMR Spectrum: (CDCl$_3$) 1.45–1.61 (m, 2H), 1.87–2.11 (m, 5H), 2.31 (s, 3H), 2.42 (s, 2H), 3.97 (d, 2H), 4.02 (m, 5H), 7.07 (s, 1H), 7.2–7.3 (m, 3H), 7.38 (t, 1H), 8.7 (s, 1H), 8.9 (s, 1H), 13.51 (s, 1H); Mass Spectrum: M+H$^+$ 486 and 488.

EXAMPLE 2

Using an analogous procedure to that described in Example 1, the appropriate 1-aryl-3-quinazolin-4-ylthiourea was reacted with the appropriate amine to give the compounds described in Table I.

TABLE I

| No. & Note | R$^6$ | R$^1$ | (R$^2$)$_n$ |
|---|---|---|---|
| [1] | allyl | N-methylpiperidin-4-ylmethoxy | 2-chloro-6-methyl |
| [2] | 2-propynyl | N-methylpiperidin-4-ylmethoxy | 2-chloro-6-methyl |
| [3] | cyclopropyl | N-methylpiperidin-4-ylmethoxy | 2-chloro-6-methyl |
| [4] | cyclopropylmethyl | N-methylpiperidin-4-ylmethoxy | 2-chloro-6-methyl |
| [5] | 2-methoxyethyl | N-methylpiperidin-4-ylmethoxy | 2-chloro-6-methyl |
| [6] | 2-dimethylaminoethyl | N-methylpiperidin-4-ylmethoxy | 2-chloro-6-methyl |
| [7] | 3-dimethylaminopropyl | N-methylpiperidin-4-ylmethoxy | 2-chloro-6-methyl |
| [8] | 2-methylthioethyl | N-methylpiperidin-4-ylmethoxy | 2-chloro-6-methyl |
| [9] | 3-methylthiopropyl | N-methylpiperidin-4-ylmethoxy | 2-chloro-6-methyl |
| [10] | 2-(2-hydroxyethoxy)ethyl | N-methylpiperidin-4-ylmethoxy | 2-chloro-6-methyl |
| [11] | allyl | 3-pyrrolidin-1-ylpropoxy | 2-chloro-6-methyl |
| [12] | 2,2,2-trifluoroethyl | 3-pyrrolidin-1-ylpropoxy | 2-chloro-6-methyl |
| [13] | 2,3-dihydroxypropyl | 3-pyrrolidin-1-ylpropoxy | 2-chloro-6-methyl |
| [14] | 2-dimethylaminoethyl | 3-pyrrolidin-1-ylpropoxy | 2-chloro-6-methyl |
| [15] | cyclobutyl | 2-morpholinoethoxy | 2-chloro-6-methyl |
| [16] | 2-hydroxyethyl | 2-morpholinoethoxy | 2-chloro-6-methyl |
| [17] | 2,3-dihydroxypropyl | 2-morpholinoethoxy | 2-chloro-6-methyl |
| [18] | 2-methoxyethyl | 2-morpholinoethoxy | 2-chloro-6-methyl |
| [19] | 2-dimethylaminoethyl | 2-morpholinoethoxy | 2-chloro-6-methyl |
| [20] | 2,2,2-trifluoroethyl | N-methylpiperidin-4-ylmethoxy | 2,6-difluoro |
| [21] | 2-methoxyethyl | N-methylpiperidin-4-ylmethoxy | 2,6-difluoro |

TABLE I-continued

| No. & Note | R⁶ | R¹ | (R²)ₙ |
|---|---|---|---|
| [22] | 2-dimethylaminoethyl | N-methylpiperidin-4-ylmethoxy | 2,6-difluoro |
| [23] | 2-acetamidoethyl | N-methylpiperidin-4-ylmethoxy | 2,6-difluoro |
| [24] | 2,2,2-trifluoroethyl | N-methylpiperidin-4-ylmethoxy | 2-chloro-6-methyl |
| [25] | 2-methoxyethyl | 3-pyrrolidin-1-ylpropoxy | 2,6-difluoro |
| [26] | 2-dimethylaminoethyl | 3-pyrrolidin-1-ylpropoxy | 2,6-difluoro |
| [27] | 2-dimethylaminoethyl | N-methylpiperidin-4-ylmethoxy | 2,6-dichloro |
| [28] | allyl | N-methylpiperidin-4-ylmethoxy | 2,6-dimethyl |
| [29] | 2-methylthioethyl | N-methylpiperidin-4-ylmethoxy | 2,6-dimethyl |
| [30] | 2-methoxyethyl | N-methylpiperidin-4-ylmethoxy | 2,6-dimethyl |
| [31] | 2-dimethylaminoethyl | N-methylpiperidin-4-ylmethoxy | 2,6-dimethyl |
| [32] | 3-dimethylaminopropyl | N-methylpiperidin-4-ylmethoxy | 2,6-dimethyl |
| [33] | 4-hydroxycyclohexyl | N-methylpiperidin-4-ylmethoxy | 2,6-dimethyl |
| [34] | allyl | 2-morpholinoethoxy | 2,6-dimethyl |
| [35] | 2-methoxyethyl | 2-morpholinoethoxy | 2,6-dimethyl |
| [36] | 2-dimethylaminoethyl | 2-morpholinoethoxy | 2,6-dimethyl |
| [37] | 2-(2-hydroxyethoxy)ethyl | 2-morpholinoethoxy | 2,6-dimethyl |
| [38] | 2-ethoxyethyl | 3-morpholinopropoxy | 2,6-dimethyl |
| [39] | 2-dimethylaminoethyl | 3-morpholinopropoxy | 2,6-dimethyl |
| [40] | 2-cyanoethyl | 3-morpholinopropoxy | 2,6-dimethyl |
| [41] | allyl | cyclopropylmethoxy | 2,6-dimethyl |
| [42] | 2-methoxyethyl | cyclopropylmethoxy | 2,6-dimethyl |
| [43] | 2-dimethylaminoethyl | cyclopropylmethoxy | 2,6-dimethyl |
| [44] | 2-ethoxyethyl | 2-pyrrolidin-1-ylethoxy | 2,6-dimethyl |
| [45] | allyl | N-methylpiperidin-4-ylmethoxy | 2-methyl |
| [46] | 2-methylsulphonylethyl | N-methylpiperidin-4-ylmethoxy | 2-chloro-6-methyl |
| [47] | t-butoxycarbonylmethyl | N-methylpiperidin-4-ylmethoxy | 2,6-dimethyl |
| [48] | 2,3-dihydroxypropyl | N-methylpiperidin-4-ylmethoxy | 2,6-dimethyl |
| [49] | 2-methoxycarbonylmethyl | 3-morpholinopropoxy | 2,6-dimethyl |
| [50] | t-butoxycarbonylmethyl | 2-pyrrolidin-1-ylethoxy | 2,6-dimethyl |
| [51] | 2-imidazol-4-ylethyl | N-methylpiperidin-4-ylmethoxy | 2-chloro-6-methyl |
| [52] | 2-(2-pyridyl)ethyl | N-methylpiperidin-4-ylmethoxy | 2-chloro-6-methyl |
| [53] | 2-phenethyl | N-methylpiperidin-4-ylmethoxy | 2-chloro-6-methyl |
| [54] | 2,6-difluorobenzyl | 3-morpholinopropoxy | 2,6-dimethyl |
| [55] | tetrahydrofuran-2-ylmethyl | N-methylpiperidin-4-ylmethoxy | 2,6-dimethyl |
| [56] | tetrahydrofuran-2-ylmethyl | 2-pyrrolidin-1-ylethoxy | 2,6-dimethyl |
| [57] | 1,4-dioxan-2-ylmethyl | 3-pyrrolidin-1-ylpropoxy | 2,6-difluoro |
| [58] | 2-piperidinoethyl | N-methylpiperidin-4-ylmethoxy | 2-chloro-6-methyl |
| [59] | 3-morpholinopropyl | N-methylpiperidin-4-ylmethoxy | 2-chloro-6-methyl |
| [60] | 2-piperidinoethyl | cyclopropylmethoxy | 2,6-dimethyl |
| [61] | 2-morpholinoethyl | cyclopropylmethoxy | 2,6-dimethyl |
| [62] | 3-morpholinopropyl | cyclopropylmethoxy | 2,6-dimethyl |
| [63] | 3-(2-oxopyrrolidin-1-yl)propyl | 2-morpholinoethoxy | 2,6-dimethyl |
| [64] | 1,4-dioxan-2-ylmethyl | N-methylpiperidin-4-ylmethoxy | 2-chloro-6-methyl |
| [65] | 2-methylsulphonylethyl | N-methylpiperidin-4-ylmethoxy | 2,6-dimethyl |
| [66] | (2R)-tetrahydrofuran-2-ylmethyl | N-methylpiperidin-4-ylmethoxy | 2,6-dimethyl |
| [67] | (2S)-tetrahydrofuran-2-ylmethyl | N-methylpiperidin-4-ylmethoxy | 2,6-dimethyl |
| [68] | 2-(tert-butoxycarbonyl-amino)ethyl | N-methylpiperidin-4-ylmethoxy | 2,6-dimethyl |
| [69] | 5-cyanopentyl | N-methylpiperidin-4-ylmethoxy | 2-chloro-6-methyl |
| [70] | 2,2-dimethyl-3-hydroxypropyl | N-methylpiperidin-4-ylmethoxy | 2-chloro-6-methyl |
| [71] | 2-cyclohexen-1-ylethyl | N-methylpiperidin-4-ylmethoxy | 2-chloro-6-methyl |
| [72] | 3-(N-t-butoxycarbonyl-N-methylamino)propyl | 3-pyrrolidin-1-ylpropoxy | 2-chloro-6-methyl |
| [73] | 3-(N-t-butoxycarbonyl-N-methylamino)propyl | 2-morpholinoethoxy | 2-methyl |
| [74] | 3-dimethylaminopropyl | 2-morpholinoethoxy | 2-methyl |
| [75] | 3-dimethylaminopropyl | 2-morpholinoethoxy | 2-chloro-6-methyl |

TABLE I-continued

| No. & Note | R⁶ | R¹ | (R²)ₙ |
|---|---|---|---|
| [76] | 3-(N-t-butoxycarbonyl-N-methylamino)propyl | 2-morpholinoethoxy | 2-chloro-6-methyl |
| [77] | 3-dimethylaminopropyl | 2-morpholinoethoxy | 2-chloro |
| [78] | 2-dimethylaminoethyl | 2-morpholinoethoxy | 2,6-dichloro |
| [79] | 3-dimethylaminopropyl | 2-morpholinoethoxy | 2,6-dichloro |
| [80] | 3-(N-t-butoxycarbonyl-N-methylamino)propyl | 2-morpholinoethoxy | 2,6-dichloro |
| [81] | 2-dimethylaminopropyl | 2-morpholinoethoxy | 2,6-dimethyl |
| [82] | 3-dimethylaminopropyl | benzyloxy | 2,6-dimethyl |
| [83] | 2-dimethylaminoethyl | benzyloxy | 2,6-dimethyl |
| [84] | 3-isopropylaminopropyl | 3-morpholinopropoxy | 2,6-dimethyl |
| [85] | 5-cyanopentyl | 2-morpholinoethoxy | 2,6-dimethyl |
| [86] | 3-hydroxy-2,2-dimethylpropyl | 2-morpholinoethoxy | 2,6-dimethyl |
| [87] | 2-dimethylaminoethyl | 2-morpholinoethoxy | 2-methyl |
| [88] | 2-cyclohexen-1-ylethyl | 2-morpholinoethoxy | 2,6-dimethyl |
| [89] | 3-dimethylaminopropyl | 2-pyridylmethoxy | 2,6-dimethyl |
| [90] | 2-dimethylaminoethyl | 2-pyridylmethoxy | 2,6-dimethyl |
| [91] | 2-(N-methylpyrrolidin-2-yl)ethyl | 2-pyridylmethoxy | 2,6-dimethyl |
| [92] | (S)-tetrahydrofuran-2-ylmethyl | 2-pyridylmethoxy | 2,6-dimethyl |
| [93] | (R)-tetrahydrofuran-2-ylmethyl | 2-pyridylmethoxy | 2,6-dimethyl |
| [94] | 2-pyridylmethyl | 2-pyridylmethoxy | 2,6-dimethyl |
| [95] | 2-methoxyethyl | 2-pyridylmethoxy | 2,6-dimethyl |
| [96] | 5-cyanopentyl | 2-pyridylmethoxy | 2,6-dimethyl |
| [97] | N-(tert-butyl)carbamoyl-methyl | N-methylpiperidin-4-ylmethoxy | 2,6-dimethyl |
| [98] | N-isopropylcarbamoyl-methyl | N-methylpiperidin-4-ylmethoxy | 2,6-dimethyl |
| [99] | N-(2-dimethylamino-ethyl)carbamoylmethyl | N-methylpiperidin-4-ylmethoxy | 2,6-dimethyl |
| [100] | (S)-1-t-butoxycarbonyl-ethyl | N-methylpiperidin-4-ylmethoxy | 2,6-dimethyl |
| [101] | (R)-1-t-butoxycarbonyl-ethyl | N-methylpiperidin-4-ylmethoxy | 2,6-dimethyl |
| [102] | (S)-1-t-butoxycarbonyl-ethyl | 2-pyrrolidin-1-ylethoxy | 2,6-dimethyl |
| [103] | (R)-1-t-butoxycarbonyl-ethyl | 2-pyrrolidin-1-ylethoxy | 2,6-dimethyl |
| [104] | t-butoxycarbonylmethyl | 2-morpholinoethoxy | 2,6-dimethyl |
| [105] | N-isopropylcarbamoyl-methyl | 2-morpholinoethoxy | 2,6-dimethyl |
| [106] | t-butoxycarbonylmethyl | N-methylpiperidin-4-ylmethoxy | 2-chloro-6-methyl |
| [107] | N-methylcarbamoyl-methyl | N-methylpiperidin-4-ylmethoxy | 2-chloro-6-methyl |
| [108] | N-isopropylcarbamoyl-methyl | N-methylpiperidin-4-ylmethoxy | 2-chloro-6-methyl |
| [109] | (S)-1-t-butoxycarbonyl-ethyl | 2-pyridylmethoxy | 2,6-dimethyl |
| [110] | 2-(2-pyridyl)ethyl | 3-morpholinopropoxy | 2,6-dimethyl |
| [111] | 2-pyridylmethyl | 2-(2-methoxyethoxy)ethoxy | 2,6-dimethyl |
| [112] | 3-pyridylmethyl | 2-(2-methoxyethoxy)ethoxy | 2,6-dimethyl |
| [113] | 4-pyridylmethyl | 2-(2-methoxyethoxy)ethoxy | 2,6-dimethyl |
| [114] | 2-(2-pyridyl)ethyl | 2-(2-methoxyethoxy)ethoxy | 2,6-dimethyl |
| [115] | 3-fluorobenzyl | N-methylpiperidin-4-ylmethoxy | 2-chloro-6-methyl |
| [116] | 2-(2-pyridyl)ethyl | 2-morpholinoethoxy | 2,6-dimethyl |
| [117] | 2-pyridylmethyl | 2-morpholinoethoxy | 2,6-dimethyl |
| [118] | (5-methyl-2-furyl)methyl | 2-morpholinoethoxy | 2,6-dimethyl |
| [119] | 2-(2-thienyl)ethyl | 2-morpholinoethoxy | 2,6-dimethyl |
| [120] | 2-thienylmethyl | N-methylpiperidin-4-ylmethoxy | 2-chloro-6-methyl |
| [121] | 2-(2-thienyl)ethyl | N-methylpiperidin-4-ylmethoxy | 2-chloro-6-methyl |

TABLE I-continued

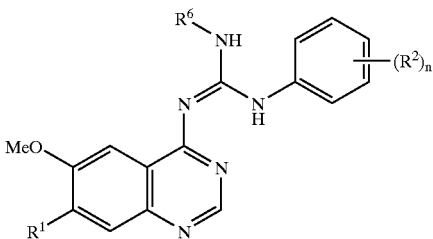

| No. & Note | R⁶ | R¹ | (R²)ₙ |
|---|---|---|---|
| [122] | (S)-tetrahydrofuran-2-ylmethyl | 2-morpholinoethoxy | 2,6-dimethyl |
| [123] | (R)-tetrahydrofuran-2-ylmethyl | 2-morpholinoethoxy | 2,6-dimethyl |
| [124] | 2-(N-methylpyrrolidin-2-yl)ethyl | 2-morpholinoethoxy | 2-chloro-6-methyl |
| [125] | 2-(N-methylpyrrolidin-2-yl)ethyl | 2-morpholinoethoxy | 2-chloro |
| [126] | 2-(N-methylpyrrolidin-2-yl)ethyl | 2-morpholinoethoxy | 2-methyl |
| [127] | 2-(N-methylpyrrolidin-2-yl)ethyl | 2-morpholinoethoxy | 2,6-dichloro |
| [128] | 2-N-methylpyrrolidin-2-yl)ethyl | 2-morpholinoethoxy | 2,6-dimethyl |
| [129] | 2-thienylmethyl | 2-morpholinoethoxy | 2,6-dimethyl |
| [130] | 2-(N-methylpyrrolidin-2-yl)ethyl | 2-(2-methoxyethoxy)ethoxy | 2,6-dimethyl |
| [131] | 2-(N-methylpyrrolidin-2-yl)ethyl | N-methylpiperidin-4-ylmethoxy | 2,5-dimethyl |
| [132] | 2-(N-t-butoxycarbonyl-piperidin-2-yl)ethyl | N-methylpiperidin-4-ylmethoxy | 2,6-dimethyl |
| [133] | 2-pyrrolidin-1-ylethyl | 3-morpholinopropoxy | 2,6-dimethyl |
| [134] | 3-pyrrolidin-1-ylpropyl | 3-morpholinopropoxy | 2,6-dimethyl |
| [135] | 2-piperazin-1-ylethyl | 3-morpholinopropoxy | 2,6-dimethyl |
| [136] | 3-(4-methylpiperazin-1-yl)propyl | 3-morpholinopropoxy | 2,6-dimethyl |
| [137] | 2-dimethylaminoethyl | N-(2-methoxyethyl)piperidin-4-ylmethoxy | 2,6-dimethyl |
| [138] | t-butoxycarbonylmethyl | N-(2-methoxyethyl)piperidin-4-ylmethoxy | 2,6-dimethyl |
| [139] | (S)-tetrahydrofuran-2-ylmethyl | N-(2-methoxyethyl)piperidin-4-ylmethoxy | 2,6-dimethyl |
| [140] | 2-dimethylaminoethyl | N-benzylmorpholin-3-ylmethoxy | 2,6-dimethyl |
| [141] | 2-dimethylaminoethyl | N-benzylmorpholin-2-ylmethoxy | 2,6-dimethyl |
| [142] | N-(2-hydroxyethyl)-carbamoylmethyl | N-methylpiperidin-4-ylmethoxy | 2,6-dimethyl |
| [143] | N-(2-hydroxyethyl)-carbamoylmethyl | N-methylpiperidin-4-ylmethoxy | 2-chloro-6-methyl |
| [144] | allyl | N-methylpiperidin-4-ylmethoxy | 2-methoxy |
| [145] | 2-cyanoethyl | N-methylpiperidin-4-ylmethoxy | 2-methoxy |
| [146] | 2-cyanoethyl | N-methylpiperidin-4-ylmethoxy | 2-chloro-6-methyl |
| [147] | 2-fluorobenzyl | N-methylpiperidin-4-ylmethoxy | 2-chloro-6-methyl |
| [148] | 4-dimethylaminobutyl | N-methylpiperidin-4-ylmethoxy | 2-chloro-6-methyl |
| [149] | cyclohexylmethyl | 2-morpholinoethoxy | 2,6-dimethyl |
| [150] | 4-dimethylaminobutyl | 2-morpholinoethoxy | 2,6-dimethyl |
| [151] | 2,3-dihydroxypropyl | 2-morpholinoethoxy | 2-methyl |
| [152] | 4-dimethylaminobutyl | 2-morpholinoethoxy | 2-chloro-6-methyl |
| [153] | 4-dimethylaminobutyl | 2-pyridylmethoxy | 2,6-dimethyl |
| [154] | 4-dimethylaminobutyl | 3-pyrrolidin-1-ylpropoxy | 2-chloro-6-methyl |
| [155] | 2-dimethylaminoethyl | N-methylpiperidin-4-ylmethoxy | 2-methyl |
| [156] | 2-dimethylaminoethyl | N-methylpiperidin-4-ylmethoxy | 2-ethyl |
| [157] | 2-(N-methylpyrrolidin-2-yl)ethyl | N-methylpiperidin-4-ylmethoxy | 2,5-dimethyl |
| [158] | 2-dimethylaminoethyl | N-methylpiperidin-4-ylmethoxy | 2,5-dimethyl |
| [159] | 2-(N-methylpyrrolidin-2-yl)ethyl | N-methylpiperidin-4-ylmethoxy | 2-chloro-6-methyl |
| [160] | 2-(N-methylpyrrolidin-2-yl)ethyl | N-methylpiperidin-4-ylmethoxy | 2,6-dichloro |
| [161] | 4-dimethylaminobutyl | N-methylpiperidin-4-ylmethoxy | 2-bromo |
| [162] | 3-dimethylaminopropyl | N-methylpiperidin-3-ylmethoxy | 2,6-dimethyl |
| [163] | 2-cyanoethyl | 3-dipropylamino-1-propynyl | 2,6-dimethyl |

Notes

[1] The product gave the following data: NMR Spectrum: (DMSOd$_6$, 100° C.) 1.4 (q, 2H), 1.8 (d, 3H), 1.98 (t, 2H), 2.2 (s, 3H), 2.31 (s, 3H), 2.8 (d, 2H), 3.72 (s, 3H), 4.0 (m, 2H) 4.18 (t, 2H), 5.2 (d, 1H), 5.36 (d, 1H), 6.06 (m, 1H), 7.1 (s, 1H), 7.3 (m, 2H), 7.46 (m, 2H), 8.4 (br s, 1H), 8.48 (s, 1H), 10.31 (br s, 1H); Mass Spectrum: M+H$^+$ 509 and 511.

[2] The product gave the following data: NMR Spectrum: (DMSOd$_6$, 100° C.) 1.44 (m, 2H), 1.79 (d, 3H), 1.96 (t, 2H), 2.2 (s, 3H), 2.34 (s, 3H), 2.81 (d, 2H), 3.32 (s, 3H), 4.03 (m, 3H), 4.3 (d, 2H), 7.11 (s, 1H), 7.3 (m, 2H), 7.41 (s, 1H), 7.7 (s, 1H), 7.85 (br s, 1H), 8.5 (s, 1H), 10.93 (br s, 1H); Mass Spectrum: M+H$^+$ 507 and 509.

[3] The product gave the following data: NMR Spectrum: (DMSOd$_6$) 0.78 (m, 2H), 0.96 (m, 2H), 1.4 (m, 2H), 1.76 (d, 3H), 1.97 (t, 2H), 2.22 (s, 3H), 2.34 (s, 3H), 2.8 (m, 3H), 3.63 (s, 3H), 3.97 (d, 2H), 7.04 (s, 1H), 7.2–7.35 (m, 3H), 7.4 (d, 1H), 8.42 (s, 1H), 8.93 (s, 1H), 9.8 (s, 1H); Mass Spectrum: M+H$^+$ 509 and 511.

[4] The product gave the following data: NMR Spectrum: (DMSOd$_6$) 0.34 (m, 2H), 0.51 (m, 2H), 1.23 (m, 1H), 1.4 (m, 2H), 1.76 (d, 3H), 1.93 (t, 2H), 2.19 (s, 3H), 2.32 (s, 3H), 2.79 (d, 2H), 3.42 (t, 2H), 3.7 (s, 3H), 3.97 (d, 2H), 7.07 (s, 1H), 7.28 (m, 2H), 7.41 (m, 2H), 8.42 (s, 1H); Mass Spectrum: M+H$^+$ 523 and 525.

[5] The product gave the following data: NMR Spectrum: (DMSOd$_6$, 100° C.) 1.32 (m, 2H), 1.72 (d, 5H), 1.86 (t, 2H), 2.14 (s, 3H), 2.28 (s, 3H), 2.77 (m, 2H), 3.31 (m, 8H), 3.94 (d, 2H), 7.01 (s, 1H), 7.28 (m, 3H), 7.41 (d, 1H), 8.42 (s, 1H), 8.5 (br s, 1H), 10.5 (br s, 1H); Mass Spectrum: M+H$^+$ 527 and 529.

[6] The product gave the following data: NMR Spectrum: (DMSOd$_6$, 100° C.) 1.39 (m, 2H), 1.77 (m, 3H), 1.95 (t, 2H), 2.19 (s, 3H), 2.28 (s, 6H), 2.3 (s, 3H), 2.78 (m, 2H), 3.58 (t, 2H), 3.58 (t, 2H), 3.7 (s, 3H), 3.98 (d, 2H), 7.06 (s, 1H), 7.23 (t, 1H), 7.3 (d, 1H), 7.4 (m, 2H), 8.39 (br s, 1H), 8.41 (s, 1H), 10.52 (br s, 1H), Mass Spectrum: M+H$^+$ 540 and 542.

[7] The product gave the following data: NMR Spectrum: (DMSOd$_6$, 100° C.) 1.4 (m, 2H), 1.75 (m, 5H), 1.93 (t, 2H), 2.09 (s, 6H), 2.19 (s, 3H), 2.31 (s, 3H), 2.37 (q, 2H), 2.79 (m, 2H), 3.57 (t, 2H), 3.74 (s, 3H), 3.99 (d, 2H), 7.07 (s, 1H), 7.26 (t, 1H), 7.31 (d, 1H), 7.41 (d, 1H), 7.53 (s, 1H), 8.3 (br s, 1H), 8.42 (s, 1H), 10.6 (br s, 1H);; Mass Spectrum: M+H$^+$ 554 and 556.

[8] The product gave the following data: NMR Spectrum: (DMSOd$_6$, 100° C.) 1.4 (m, 2H), 1.78 (m, 3H), 1.95 (t 2H), 2.14 (s, 3H), 2.19 (s, 3H), 2.31 (s, 3H), 2.72–2.84 (m, 4H), 3.7 (q, 2H), 3.77 (s, 3H), 3.99 (d, 2H), 7.09 (s, 1H), 7.21–7.32 (m, 2H), 7.4 (d, 2H), 7.44 (s, 1H), 7.9 (br s, 1H), 8.43 (s, 3H), 10.8 (br s, 1H), Mass Spectrum: M+H$^+$ 543 and 545.

[9] The product gave the following data: NMR Spectrum: (DMSOd$_6$, 100° C.) 1.4 (m, 2H), 1.76 (m, 3H), 1.9–2.0 (m, 3H), 2.08 (s, 3H), 2.19 (s, 3H), 2.6 (t, 2H), 2.78 (d, 2H), 3.59 (q, 2H), 3.75 (s, 3H), 3.98 (d, 2H), 7.08 (s, 1H), 7.21–7.32 (m, 2H), 7.4 (d, 1H), 7.52 (s, 1H), 8.10 (br, s, 1H), 8.43 (s, 1H), 10.55 (br s, 1H); Mass Spectrum: M+H$^+$ 557 and 559.

8 10] The product gave the following data: NMR Spectrum: (DMSOd$_6$, 100° C.) 1.39 (m, 2H), 1.76 (m, 3H), 1.92 (t, 2H), 2.08 (s, 3H), 2.31 (s, 3H), 2.69 (t, 2H), 2.77 (m, 2H), 3.33 (t, 2H), 3.36 (m, 2H), 3.7 (m, 5H), 3.98 (d, 2H), 4.14 (s, 1H), 7.06 (s, 1H), 7.23 (t, 1H), 7.3 (d, 1H), 7.4 (d, 2H), 8.42 (s, 1H), 8.48 (br s, 1H), 10.01 (br s, 1H); Mass Spectrum: M+H$^+$ 557 and 559.

[11] The product gave the following data: NMR Spectrum (DMSOd$_6$, 100° C.) 1.7 (m, 4H), 1.94 (m, 2H), 2.31 (s, 3H), 2.55 (m, 4H), 2.6 (t, 2H), 3.71 (s, 3H), 4.23 (m, 4H), 5.17 (d, 1H), 5.32 (d, 1H), 6.01 (m, 1H), 7.07 (s, 1H), 7.2–7.3 (m, 2H), 7.39 (d, 1H), 7.44 (s, 1H), 8.32 (br s, 1H), 8.43 (s, 1H), 10.29 (br s, 1H); Mass Spectrum: M+H$^+$ 509 and 511.

The 1-(2-chloro-6-methylphenyl)-3-[6-methoxy-7-(3-pyrrolidin-1-ylpropoxy)quinazolin-4-yl]thiourea used as a starting material was prepared as follows:—

A mixture of 7-benzyloxy-6-methoxy-3,4-dihydroquinazolin-4-one (International Patent Application WO 97/22596, Example 1 thereof; 25.1 g) thionyl chloride (450 ml) and DMF (1 ml) was stirred and heated to reflux for 2 hours. The mixture was evaporated and the residue was dissolved in toluene and the solution was evaporated. The resultant solid was suspended in methylene chloride (500 ml), solid potassium carbonate (39 g) was added and the mixture was stirred for 10 minutes. Water (500 ml) was added and the mixture stirred for another 10 minutes. The methylene chloride layer was separated, dried over magnesium sulphate and evaporated. The residue was purified by column chromatography on silica using increasingly polar mixtures of methylene chloride and ethyl acetate as eluent. There was thus obtained 7-benzyloxy-4-chloro-6-methoxyquinazoline (21.54 g); NMR Spectrum (DMSOd$_6$) 4.0 (s, 3H), 5.36 (s, 2H), 7.31–7.46 (m, 4H), 7.51 (d, 2H), 7.58 (s, 1H), 8.88 (s, 1H).

A portion (3 g) of the material so obtained was dissolved in a 1M solution of ammonia in isopropanol (50 ml). Liquid ammonia (5 ml) was added and the reaction mixture was sealed in a Carius tube. The reaction mixture was heated to 120° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was obtained 4-amino- 7-benzyloxy-6-methoxyquinazoline (2.65 g); NMR Spectrum (DMSOd$_6$) 3.88 (s, 3H), 3.9 (s, 3H), 7.2 (s, 1H), 7.63 (s, 2H), 7.69 (s, 1H), 8.38 (s, 1H); Mass Spectrum: M+H+ 230.

A mixture of 4-amino-7-benzyloxy-6-methyoxyquinazoline (4.15 g) and trifluoroacetic acid (35 ml) was stirred and heated to reflux for 1 hour. The solvent was evaporated, the residue was redissolved in a mixture of methylene chloride and toluene and the solvent was evaporated. The solid so obtained was suspended in water and basified to pH1.1 by the addition of 2N aqueous sodium hydroxide solution. The mixture was then neutralised to pH7 by the addition of 1N aqueous hydrochloric acid solution. The resultant solid was collected, washed in turn with water and acetonitrile and dried under vacuum over phosphorus pentoxide. There was thus obtained 4-amino-7-hydroxy-6-methoxyquinazoline (2.55 g); NMR Spectrum: (DMSOd$_6$) 3.9 (s, 3H), 7.05 (s, 1H), 7.65 (s, 1H), 8.0 (br s, 2H), 8.35 (s, 1H), 10.0–11.0 (br s, 1H).

A portion (0.15 g) of the material so obtained and triphenylphosphine (0.31 g) were dissolved in DMF (3 ml). THF (3 ml) was added causing partial precipitation of the starting material. A solution of N-(3-hydroxypropyl)pyrrolidine (0.11 g) in THF (1 ml) was added followed by diethyl azodicarboxylate (0.186 ml) and the reaction mixture was stirred at ambient temperature for 30 minutes. Further portions of triphenylphosphine (0.105 g), N-(3-hydroxypropyl) pyrrolidine (0.02 g) and diethyl azodicarboxylate (0.062 ml) were added and reaction mixture was stirred at ambient temperature for a further 30 minutes. The mixture was evaporated and the residue was purified by column chromatography on silica using increasingly polar mixtures of methylene chloride and methanol as eluent. There was thus obtained 4-amino-6-methoxy-7-(3-pyrrolidin-1-ylpropoxy)

quinazoline (0.16 g); NMR Spectrum: (DMSOd$_6$ and CF$_3$COOD) 1.9 (m, 2H), 2.05 (m, 2H), 2.25 (m, 2H), 3.05 (m, 2H), 3.35 (m, 2H), 3.65 (m, 2H), 3.95 (s, 3H), 4.3 (t, 2H), 7.25 (s, 1H), 7.85 (s, 1H), 8.75 (s, 1H), 9.4 (br s, 1H); Mass Spectrum: M+H$^+$ 303.

The material so obtained was reacted with 2-chloro-6-methylphenyl isothiocyanate using an analogous procedure to that described in the last paragraph of the portion of Example 1 which is concerned with the preparation of starting materials. There was thus obtained the required starting material 1-(2-chloro-6-methylphenyl)-3-[6-methoxy-7-(3-pyrrolidin-1-ylpropoxy)quinazolin-4-yl]thiourea; NMR Spectrum: (CDCl$_3$) 1.8 (m, 4H), 2.18 (m, 2H), 2.4 (s, 3H), 2.55 (m, 4H), 2.68 (t, 2H), 4.02 (s, 3H), 4.3 (t, 2H), 7.07 (s, 1H), 7.26 (m, 2H), 7.31 (s, 1H), 7.37 (m, 1H), 8.7 (s, 1H), 8.94 (br s, 1H), 13.51 (s, 1H); Mass Spectrum: M+H$^+$ 486 and 488.

The N-(3-hydroxypropyl)pyrrolidine used as a starting material was prepared as follows:—

A mixture of 3-chloropropanol (66 g), pyrrolidine (50 g), potassium carbonate (145 g) and acetonitrile (1 L) was stirred and heated to reflux for 20 hours. The mixture was cooled to ambient temperature and filtered. The filtrate was evaporated and the residue was purified by distillation to give the required starting material as an oil (62 g); NMR Spectrum: (CDCl$_3$) 1.6–1.8 (m, 6H), 2.55 (br s, 4H), 2.75 (t, 2H), 5.5 (br s, 1H).

[12] The product gave the following data: NMR Spectrum: (DMSOd$_6$, 100° C.) 1.73 (m, 4H), 1.95 (m, 2H), 2.3 (s, 3H), 2.67 (m, 2H), 3.8 (s, 3H), 3.88–3.97 (d, 1H), 4.1–4.25 (m, 3H), 4.35 (m, 2H), 7.1 (s, 1H), 7.2–7.3 (m, 2H), 7.4 (d, 1H), 7.64 (br s, 2H), 8.5 (s, 1H), 11.43 (s, 1H); Mass Spectrum: M+H$^+$ 551 and 553.

[13] The product gave the following data: NMR Spectrum: (DMSOd$_6$, 100° C.) 1.7 (m, 4H), 1.95 (m, 2H), 2.32 (s, 3H), 2.63 (m, 2H), 3.53 (m, 4H), 3.73 (m, 5H), 3.8 (br s, 1H), 4.18 (t, 2H), 4.33 (m, 1H), 4.75 (br s, 1H), 7.07 (s, 1H), 7.2–7.3 (m, 2H), 7.42 (m, 1H), 8.47 (br s, 2H), 10.15 (br s, 1H): Mass Spectrum: M+H$^+$ 543 and 545.

[14] The product gave the following data: NMR Spectrum: (DMSOd$_6$, 100° C.) 1.71 (m, 4H), 1.95 (m, 2H), 2.26 (s, 6H), 2.31 (s, 3H),2.55 (m, 4H), 2.6 (t, 4H), 3.58 (q, 2H), 3.7 (s, 3H), 4.16 (t, 2H), 7.06 (s, 1H), 7.2–7.3 (m, 2H), 7.39 (d, 1H), 8.4 (br s, 1H), 8.41 (s, 1H), 10.56 (br s, 1H); Mass Spectrum: M+H$^+$ 540 and 542.

[15] The product gave the following data: NMR Spectrum: (DMSOd$_6$, 100° C.) 1.71–1.9 (m, 2H), 2.1 (m, 2H), 2.3 (s, 3H), 2.5 (m, 6H), 2.78 (t, 2H), 3.59 (t, 4H), 3.68 (s, 3H), 4.21 (t, 2H), 4.48 (q, 1H), 7.08 (s, 1H), 7.2–7.4 (m, 4H), 8.43 (s, 1H), 8.98 (br s, 1H), 9.53 (br s, 1H); Mass Spectrum: M+H$^+$ 525 and 527.

The 1-(2-chloro-6-methylphenyl)-3-[6-methoxy-7-(2-morpholinoethoxy)quinazolin-4-yl]thiourea used as a starting material was prepared as follows:—

A mixture of 7-acetoxy-6-methoxyquinazolin-4-one (International Patent Application WO 96/15118, Example 17 thereof; 15 g), thionyl chloride (225 ml) and DMF (5 ml) was stirred and heated to 90° C. for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 7-acetoxy-4-chloro-6-methoxyquinazoline (13.2 g) which was used without further purification.

A mixture of the material so obtained was reacted with 2-bromo-4-fluorophenol using an analogous procedure to that described in the third last paragraph of the portion of Example 1 above which is concerned with the preparation of starting materials. There was thus obtained 7-acetoxy-4-(2-bromo-4-fluorophenoxy)-6-methoxyquinazoline (14.7 g).

A mixture of a portion (3 g) of the material so obtained, concentrated ammonium hydroxide solution (0.88 g/ml, approximately 14M; 60 ml) and methanol (120 ml) was stirred at ambient temperature for 16 hours. The mixture was evaporated and the residue was triturated under diethyl ester. There was thus obtained 4-(2-bromo-4-fluorophenoxy)-7-hydroxy-6-methoxyquinazoline (2.2 g); NMR Spectrum: (DMSOd$_6$) 3.99 (s, 3H), 7.25 (s, 1H), 7.39 (m, 1H), 7.54 (m, 2H), 7.78 (m, 1H), 8.47 (s, 1H), 10.82 (s, 1H); Mass Spectrum: M–H$^-$ 363 & 365.

A mixture of 4-(2-bromo-4-fluorophenyl)-7-hydroxy-6-methoxyquinazoline (0.94 g), 2-morpholinoethyl chloride (0.4 g), potassium carbonate (1.42 g) and DMF (20 ml) was stirred and heated to 65° C. for 16 hours. The mixture was filtered and evaporated. The resulting oil was purified by column chromatography on silica using increasingly polar mixtures of methylene chloride and a 2M methanolic ammonia solution as eluent. There was thus obtained 4-(2-bromo-4-fluorophenoxy)-6-methoxy-7-(2-morpholinoethoxy)quinazoline (0.72 g); NMR Spectrum: (CDCl$_3$) 2.63 (t, 4H), 2.98 (t, 2H), 3.76 (t, 4H), 4.06 (s, 3H), 4.34 (t, 2H), 7.22 (t, 1H), 7.32 (s, 1H), 7.41 (t, 2H), 7.52 (s, 1H), 8.6 (s, 1H); Mass Spectrum: M+H$^+$ 478 and 480.

The material so obtained was reacted with ammonia using an analogous procedure to that described in the second last paragraph of the portion of Example 1 is which is concerned with the preparation of starting materials. There was thus obtained 4-amino-6-methoxy-7-(2-morpholinoethoxy)quinazoline; NMR Spectrum: (DMSOd$_6$) 2.5 (m, 4H), 2.75 (t, 2H), 3.58 (t, 4H), 3.87 (s, 3H), 4.2 (t, 2H), 7.09 (s, 1H), 7.39 (s, 2H), 7.58 (s, 1H), 8.24 (s, 1H); Mass Spectrum: M+H$^+$ 305.

The material so obtained was reacted with 2-chloro-6-methylphenyl isothiocyanate using an analogous procedure to that described in the last paragraph of the portion of Example 1 which is concerned with the preparation of starting materials. There was thus obtained the required starting material 1-(2-chloro-6-methylphenyl)-3-[6-methoxy-7-(2-morpholinoethoxy)quinazolin-4-yl]thiourea; NMR Spectrum: (CDCl$_3$) 2.43 (s, 3H), 2.66 (t, 4H), 2.97 (t, 2H), 3.78 (t, 4H), 4.07 (s, 3H), 4.36 (t, 2H), 7.11 (s, 1H), 7.26 (s, 1H), 7.32 (s, 1H), 7.39 (m, 1H); 8.73 (s, 1H) 8.94 (s, 1H), 13.55 (s, 1H); Mass Spectrum: M+H$^+$ 488 and 490.

[16] The product gave the following data: NMR Spectrum: (DMSOd$_6$, 100° C.) 2.3 (s, 3H), 2.5 (m, 4H), 2.78 (t, 2H), 3.6 (m, 6H), 3.7 (m, 5H), 4.22 (t, 2H), 4.64 (s, 1H), 7.1 (s, 1H), 7.22 (t, 1H), 7.3 (d, 1H), 7.4 (d, 1H), 8.42 (s, 1H), 8.5 (br s, 1H), 10.02 (br s, 1H); Mass Spectrum: M+H$^+$ 515 and 517.

[17] The product gave the following data: NMR Spectrum: (DMSOd$_6$, 100° C.) 2.3 (s, 3H), 2.5 (m, 4H), 2.78 (t, 2H), 3.49 (m, 3H), 3.59 (t, 4H), 3.69 (m, 4H), 3.8 (s, 1H), 4.22 (t, 2H), 4.29 (s, 1H), 4.74 (s, 1H), 7.1 (s, 1H), 7.28 (m, 2H), 7.4 (m, 2H), 8.4 (br s, 1H), 8.45 (s, 1H), 10.2 (br s, 1H); Mass Spectrum: M+H$^+$ 545 and 547.

[18] The product gave the following data: NMR Spectrum: (DMSOd$_6$, 100° C.) 2.3 (s, 3H), 2.52 (m, 4H), 2.79 (t, 2H), 3.35 (s, 3H), 3.57 (t, 4H), 3.64 (m, 4H), 3.7 (s, 3H), 4.21 (t, 2H), 7.1 (s, 1H), 7.26 (m, 2H), 7.4 (t, 2H), 8.33 (br s, 1H), 8.44 (s, 1H), 10.25 (br s, 1H); Mass Spectrum: M+H$^+$ 529 and 531.

[19] The product gave the following data: NMR Spectrum: (DMSOd$_6$, 100° C.) 2.25 (s,6H), 2.3 (s, 3H), 2.5 (m, 4H), 2.59 (t, 2H), 2.76 (t, 2H), 3.59 (t, 6H), 3.7 (s, 3H), 4.22 (t, 2H), 7.1 (s, 1H), 7.21 (t, 1H), 7.29 (d, 1H), 7.41, (t, 2H), 8.35 (br s, 1H), 8.43 (s, 1H), 10.55 (br s, 1H), Mass spectrum: M+H⁺ 542 and 544.

[20] The product gave the following data: Mass Spectrum: M+H⁺ 539.

The 1-(2,6-difluorophenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy) quinazoline was reacted with 2,6-difluorophenyl isothiocyanate using an analogous procedure to that described in the last paragraph of the portion of Example 1 which is concerned with the preparation of starting materials. There was thus obtained the required starting material: NMRS Spectrum: (CDCl₃) 1.43–1.6 (m, 2H),1.83–2.09 (m, 5H), 2.33 (s, 3H), 2.94 (d, 2H), 4.04 (m, 5H), 7.0–7.14 (m, 4H), 7.27 (m, 1H), 7.35 (m, 1H), 8.7 (s, 1H), 13.49 (s, 1H); Mass Spectrum: M+H+ 474.

[21] The product gave the following data: NMR Spectrum: (DMSOd₆, 100° C.) 1.41 (m, 2H), 1.77 (m, 3H), 1.94 (t, 2H), 2.2 (s, 3H), 2.8 (d, 2H), 3.39 (s, 3H), 3.68 (m, 4H), 3.71 (s, 3H), 3.99 (d, 2H), 7.09 (s, 1H), 7.2 (t, 2H), 7.39 (s, 2H), 8.46 (s, 1H), 9.34 (br s, 1H), 9.69 (br s, 1H); Mass Spectrum: M+H⁺ 515.

[22] The product gave the following data: NMR Spectrum: (DMSOd₆, 100° C.) 1.41 (m, 2H), 1.78 (m, 3H), 1.97 (t, 2H), 2.2 (s, 3H), 2.31 (s, 6H), 2.63 (t, 2H), 2.8 (d, 2H), 3.6 (t, 2H), 3.71 (s, 3H), 3.99 (d, 2H), 7.09 (s, 1H), 7.19 (t, 2H), 7.39 (m, 2H), 8.47 (s, 1H), 9.4 (br s, 1H), 10.2 (br s, 1H); Mass Spectrum: M+H⁺ 528.

[23] The product gave the following data: NMR Spectrum: (DMSOd₆, 100° C.) 1.67 (m, 2H), 1.98–2.10 (m, 6H), 2.19 (t, 2H), 2.44 (s, 3H), 3.04 (m, 2H), 3.63 (q, 2H), 3.87 (q, 2H), 4.01 (s, 3H), 4.24 (d, 2H), 7.32 (s, 1H), 7.42 (t, 2H), 7.61 (m, 1H), 7.7 (s, 1H), 7.94 (s, 1H), 8.7 (s, 1H), 9.11 (br s, 1H), 10.26 (br s, 1H); Mass Spectrum: M+H⁺ 542.

[24] The product gave the following data: NMR Spectrum: (DMSOd₆, 100° C.) 1.52 (m, 2H), 1.9 (m, 3H), 2.3 (s, 3H), 2.4 (m, 5H), 3.0 (d, 2H), 3.8 (s, 3H), 4.05 (d, 2H), 4.31 (m, 2H), 7.17 (s, 1H), 7.3 (m, 2H), 7.41 (d, 1H), 7.63 (s, 1H), 7.72 (br s, 1H), 8.5 (s, 1H), (s, 1H), 10.41 (br s, 1H); Mass Spectrum: M+H⁺ 551 and 553.

[25] The product gave the following data: NMR Spectrum: (DMSOd₆, 100° C.) 1.71 (m, 4H), 1.97 (m, 2H), 2.54 (m, 4H), 2.64 (t, 2H), 3.4 (s, 3H), 3.69 (m, 7H), 4.19 (t, 2H), 7.11 (s, 1H), 7.18 (m, 2H), 7.39 (s, 2H), 8.48 (s, 1H), 9.32 (br s, 1H), 9.6 (br s, 1H); Mass Spectrum: M+H⁺ 515.

The 1-(2,6-difluorophenyl)-3-[6-methoxy-7-(3-pyrrolidin-1-ylpropoxy)quinazolin-4-yl]thiourea used as a starting material was prepared by the reaction of 4-amino-6-methoxy-7-(3-pyrrolidin-1-ylpropoxy)quinazoline with 2,6-difluorophenyl isothiocyanate using an analogous procedure to that described in the last paragraph of the portion of Example 1 which is concerned with the preparation of starting materials. The required starting material gave the following data: NMR Spectrum: (CDCl₃) 1.83 (s, 4H), 2.2 (m, 2H), 2.61 (s, 4H), 2.74 (t, 2H), 4.04 (s, 3H), 4.48 (t, 2H), 6.98–7.11 (m, 3H), 7.27–7.41 (m, 3H), 8.71 (s, 1H), 13.48 (s, 1H); Mass Spectrum: M+H⁺ 474.

[26] The product gave the following data: NMR Spectrum: (DMSOd₆, 100° C.) 1.87 (m, 4H), 2.0 (m, 2H), 2.32 (s, 6H), 2.53–2.7 (m, 8H), 3.6 (t, 2H), 3.7 (s, 3H), 4.2 (t, 2H), 7.09 (s, 1H), 7.18 (m, 2H), 7.31 (m, 2H), 8.48 (s, 1H), 9.43 (br s, 1H); Mass Spectrum: M+H⁺ 528.

[27] The product gave the following data: NMR Spectrum: (DMSOd₆, 100° C.) 1.41 (m, 2H), 1.88 (m, 3H), 2.0 (t, 2H), 2.21 (s, 3H), 2.29 (s, 6H), 2.62 (t, 2H), 2.8 (d, 2H), 3.58 (t, 2H), 3.68 (s, 3H), 3.96 (d, 2H), 7.07 (s, 1H), 7.3 (m, 2H), 7.53 (d, 2H), 8.43 (s, 1H), 9.1 (br s, 1H); Mass Spectrum: M+H⁺ 560, 562 and 564.

The 1-(2,6-dichlorophenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy) quinazoline was reacted with 2,6-dichlorophenyl isothiocyanate using an analogous procedure to that described in the last paragraph of the portion of Example 1 which is concerned with the preparation of starting materials. There was thus obtained the required starting material: Mass Spectrum: M+H⁺ 506 and 508.

[28] The product gave the following data: NMR Spectrum: (DMSOd₆, 100° C.) 1.4 (m, 2H), 1.76 (m, 3H), 1.96 (m, 2H), 2.2 (s,3H), 2.24 (s, 6H), 2.8 (m, 2H), 3.77 (s, 3H), 3.99 (m, 2H), 4.12 (t, 2H), 5.14 (d, 1H), 5.29 (d, 1H), 6.01 (m, 1H), 7.06 (s, 1H), 7.17 (s, 3H), 7.54 (s, 1H), 8.41 (s, 1H), 8.6 (br s, 1H), 10.5 (br s, 1H); Mass Spectrum: M+H⁺ 489.

The 1-(2,6-dimethylphenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy) quinazoline was reacted with 2,6-dimethylphenyl isothiocyanate using an analogous procedure to that described in the last paragraph of the portion of Example 1 which is concerned with the preparation of starting materials. There was thus obtained the required starting material: NMR Spectrum: (CDCl₃) 1.44–1.61 (m, 2H), 1.87–2.08 (m, 5H), 2.32 (s, 3H), 2.36 (s, 6H), 2.94 (d, 2H), 4.04 (m, 5H), 7.1 (s, 1H), 7.19 (m, 3H), 7.29 (s, 1H), 8.69 (s, 1H), 13.37 (s, 1H); Mass Spectrum: M+H⁺ 466.

[29] The product gave the following data: NMR Spectrum: (DMSOd₆, 100° C.) 1.4 (m, 2H), 1.77 (m, 3H), 1.93 (t, 2H), 2.1 (s, 3H), 2.09 (s, 3H), 2.27 (s, 6H), 2.78 (m, 4H), 3.68 (q, 2H), 3.81 (s, 3H), 4.0 (d, 2H), 7.09 (s, 1H), 7.18 (s, 3H), 7.69 (s, 1H), 8.44 (s, 1H), 11.1 (s, 1H); Mass Spectrum: M+H⁺ 523.

[30] The product gave the following data: NMR Spectrum: (DMSOd₆, 100° C.) 1.4 (m, 2H), 1.78 (d, 3H), 1.97 (t, 2H), 2.2 (s, 3H), 2.27 (s, 6H), 2.79 (d, 2H), 3.32 (s, 3H), 3.6 (m, 2H), 3.66 (m, 2H), 3.76 (s, 3H), 3.99 (d, 2H), 7.08 (s, 1H), 7.18 (s, 3H), 7.58 (s, 1H), 8.43 (s, 1H), 10.54 (br s, 1H); Mass Spectrum: M+H⁺ 507.

[31] The product gave the following data: NMR Spectrum: (DMSOd₆, 100° ) 1.39 (m, 2H), 1.75 (m, 3H), 1.92 (t, 2H), 2.19 (s, 3H), 2.22 (s, 6H), 2.25 (s, 6H), 2.54 (t, 2H), 2.77 (m, 2H), 3.58 (q, 2H), 3.76 (s, 3H), 3.98 (d, 2H), 7.05 (s, 1H), 7.16 (s, 3H), 7.59 (s, 1H), 8.41 (s, 1H), 10.80 (br s, 1H); Mass Spectrum: M+H⁺ 520.

[32] The product gave the following data: NMR Spectrum: (DMSOd₆, 100° C.) 1.4 (m, 2H), 1.75 (m, 5H), 1.94 (t, 2H), 2.02 (s, 6H), 2.19 (s, 3H), 2.24 (s, 6H), 2.33 (t, 2H), 2.8 (d, 2H), 3.57 (t, 2H), 3.8 (s, 3H), 4.0 (d, 2H), 7.06 (s, 1H), 7.18 (s, 3H), 7.63 (s, 1H), 8.42 (s, 1H), 10.9 (br s, 1H); Mass Spectrum: M+H⁺ 534.

[33] trans-4-Hydroxycyclohexylamine was used as the appropriate amine and the reaction mixture also contained diisopropylethylamine (1 equivalent). The product gave the following data: NMR Spectrum: (DMSOd₆, 100° C.) 1.3–1.5 (m, 6H), 1.7–2.1 (m, 9H), 2.18 (s, 3H), 2.25 (s, 6H), 2.77 (d, 2H), 2.97 (br s, 2H), 3.5 (s, 3H), 3.9–4.0 (m, 3H), 4.1 (d, 1H), 7.01 (s, 1H), 7.13 (s, 1H), 7.41 (br s, 1H), 8.4 (s, 1H); Mass Spectrum: M+H⁺ 547.

[34] The product gave the following data: NMR Spectrum: (DMSOd₆, 100° C.) 2.29 (s, 6H), 2.55 (m, 4H), 2.8 (t, 2H), 3.61 (t, 4H), 3.87 (s, 3H), 4.2 (t, 2H), 4.37 (t, 2H), 5.18 (d, 1H), 5.3 (d, 1H), 6.03 (m, 1H), 7.11 (s, 1H), 7.2 (s, 3H), 7.59 (s, 1H), 7.6 (br s, 1H), 8.45 (s, 1H), 10.52 (br s, 1H); Mass Spectrum: M+H$^+$ 491.

The 1-(2,6-dimethylphenyl)-3-[6-methoxy-7-(2-morpholinoethoxy)quinazolin-4-yl]thiourea used as a starting material was prepared as follows:—

4-Amino-6-methoxy-7-(2-morpholinoethoxy)quinazoline was reacted with 2,6-dimethylphenyl isothiocyanate using an analogous procedure to that described in the last paragraph of the portion of Example 1 which is concerned with the preparation of starting materials. There was thus obtained the required starting material: NMR Spectrum: (CDCl$_3$) 2.36 (s, 6H), 2.61 (t, 4H), 2.95 (t, 2H), 3.77 (t, 4H), 4.04 (s, 3H), 4.34 (t, 2H), 7.11 (s, 1H), 7.2 (m, 3H), 7.31 (s, 1H), 8.69 (s, 1H), 8.9 (s, 1H), 13.36 (s, 1H); Mass Spectrum: M+H$^+$ 468.

[35] The product gave the following data: NMR-Spectrum: (DMSOd$_6$, 100° C.) 2.28 (s, 6H), 2.52 (m, 4H), 2.8 (t, 2H), 3.33 (s, 3H), 3.6 (m, 6H), 3.68 (t, 2H), 3.78 (s, 3H), 4.26 (t, 2H), 7.11 (s, 1H), 7.2 (s, 3H), 7.6 (s, 1H), 8.44 (s, 1H), 10.55 (br s, 1H); Mass Spectrum: M+H$^+$ 509.

[36] The product gave the following data: NMR Spectrum: (DMSOd$_6$, 100° C.) 2.24 (s, 6H), 2.28 (s, 6H), 2.57 (m, 6H), 2.8 (t, 2H), 3.59 (m, 6H), 3.77 (s, 3H), 4.26 (t, 2H), 7.11 (s, 1H), 7.19 (s, 3H), 7.6 (s, 1H), 8.42 (s, 1H), 10.8 (br s, 1H), Mass Spectrum: M+H$^+$ 522.

[37] The product gave the following data: NMR Spectrum: (DMSOd$_6$, 100° C.) 2.29 (s, 6H), 2.54 (m, 4H), 2.8 (t, 2H), 3.54 (m, 4H), 3.61 (t, 4H), 3.69 (m, 4H), 3.78 (s, 3H), 4.12 (s, 1H), 4.25 (t, 2H), 7.11 (s, 1H), 7.18 (s, 3H), 7.5 (br s, 1H), 7.59 (s, 1H), 8.45 (s, 1H), 10.5 (br s, 1H); Mass Spectrum: M+H$^+$ 539.

[38] The product gave the following data: NMR Spectrum: (CDCl$_3$) 1.12 (t, 3H), 2.13 (m, 2H), 2.33 (s, 6H), 2.5 (m, 4H), 2.58 (t, 2H), 3.45 (d, 2H), 3.61 (d, 2H), 3.73 (m, 6H), 3.98 (s, 3H), 4.26 (t, 2H), 4.7 (s, 1H), 7.18 (s, 4H), 7.86 (s, 1H), 8.56 (s, 1H), 12.53 (s, 1H), Mass Spectrum: M+H$^+$ 537.

The 1-(2,6-dimethylphenyl)-3-[6-methoxy-7-(3-morpholinopropoxy)quinazolin-4-yl]thiourea used as a starting material was prepared as follows:—

4-Amino-7-hydroxy-6-methoxyquinazoline was reacted with N-(3-hydroxypropyl)morpholine (*Bull, Soc. Chim. Fr.* 1992, 1117) using an analogous procedure to that described in the second last paragraph of the portion of Note [11] hereinbefore that is concerned with the preparation of starting materials. There was thus obtained 4-amino-6-methoxy-7-(3-morpholinopropoxy)quinazoline; NMR Spectrum: (DMSOd$_6$ and CF$_3$COOD) 2.25 (m, 2H), 3.15 (m, 2H), 3.35 (m, 2H), 3.55 (m, 2H), 3.7 (t, 2H), 3.95 (s, 3H), 4.05 (m, 2H), 4.3 (t, 2H), 7.35 (s, 1H), 7.85 (s, 1H), 8.75 (s, 1H), 9.4 (br s, 1H); Mass Spectrum: M+H$^+$ 319.

4-Amino-6-methoxy-7-(3-morpholinopropoxy)quinazoline was reacted with 2,6-dimethylphenyl isothicyante using an analogous procedure to that described in the last paragraph of the portion of Example 1 which is concerned with the preparation of starting materials. There was thus obtained the required starting material: NMR Spectrum: (DMSOd$_6$) 2.0 (m, 2H), 2.4 (s, 4H), 2.45 (t, 2H), 3.58 (t, 4H), 4.03 (s, 3H), 4.21 (t, 2H), 7.18 (m, 3H), 7.33 (s, 1H), 8.19 (s, 1H), 8.71 (s, 1H), 11.09 (s, 1H), 13.7 (s, 1H); Mass Spectrum: M+H$^+$ 482.

[39] The product gave the following data: NMR Spectrum: (CDCl$_3$) 2.2–2.31 (m, 8H), 2.33 (s, 6H), 2.5 (s, 6H), 2.59 (t, 2H), 3.65 (d, 2H), 3.73 (t, 4H), 4.02 (s, 3H), 4.26 (t, 2H), 4.85 (s, 1H), 7.17 (m, 4H), 7.9 (s, 1H), 8.55 (s, 1H), 12.59 (s, 1H); Mass Spectrum: M+H$^+$ 536.

[40] The product gave the following data: NMR Spectrum: (CDCl$_3$) 2.13 (m, 2H), 2.36 (s, 6H), 2.49 (m, 4H), 2.6 (t, 2H), 2.97 (t, 2H), 3.73 (t, 4H), 3.8 (q, 2H), 4.02 (s, 3H), 4.27 (t, 2H), 4.65 (t, 1H), 7.21 (d, 4H), 7.8 (s, 1H), 8.6 (s, 1H), 12.6 (s, 1H); Mass Spectrum: M+H$^+$ 518.

[41] The product gave the following data: NMR Spectrum: (CDCl$_3$) 0.42 (m, 2H), 0.71 (m, 2H), 1.28 (m, 1H), 2.35 (s, 6H), 3.98 (m, 5H), 4.21 (m, 2H), 4.35 (br s, 1H), 5.1–5.25 (m, 2H), 5.97 (m, 1H), 7.15 (s, 1H), 7.18 (s, 3H), 7.91 (br s, 1H), 7.91 (br s, 1H), 8.55 (s, 1H), 12.58 (br s, 1H); Mass Spectrum: M+H$^+$ 432.

The 1-(2,6-dimethylphenyl)-3-(7-cyclopropylmethoxy-6-methoxyquinazolin-4-yl)thiourea used as a starting material was prepared as follows:—

A mixture of 4-(4-bromo-2-fluorophenoxy)-7-hydroxy-6-methoxyquinazoline (6.99 g), cyclopropylmethyl chloride (2.16 g), potassium iodide (0.043 g), potassium carbonate (12 g) and DMF (200 ml) was stirred and heated to 45° C. for 16 hours. The mixture was cooled to ambient temperature and filtered. The filtrate was evaporated and the residue was purified by column chromatography on silica using increasingly polar mixtures of methylene chloride and methanol as eluent. There was thus obtained 4-(4-bromo-2-fluorophenoxy)-7-cyclopropylmethoxy-6-methoxyquinazoline (7.6 g); NMR Spectrum: (DMSOd$_6$) 0.43 (m, 2H), 0.68 (m, 2H), 1.37 (m, 1H), 4.0 (s, 3H), 4.1 (d, 2H), 7.4 (s, 1H), 7.45 (m, 1H), 7.57 (m, 2H), 7.82 (m, 1H), 8.58 (s, 1H); Mass Spectrum: M+H$^+$ 421 and 423.

Using an analogous procedure to that described in the second last paragraph of the portion of Example 1 that is concerned with the preparation of starting materials, 4-(4-bromo-2-fluorophenoxy)-7-cyclopropylmethoxy-6-methoxyquinazoline (1.75 g) was reacted with ammonia in isopropanol. There was thus obtained 4-amino-7-cyclopropylmethoxy-6-methoxyquinazoline (1.75 g); NMR Spectrum: (DMSOd$_6$) 0.36 (m, 2H), 0.58 (m, 2H), 1.3 (m, 1H), 3.88 (s, 3H), 3.94 (d, 2H), 6.97 (s, 1H), 7.39 (br s, 2H), 7.55 (s, 1H), 8.25 (s, 1H); Mass Spectrum: M+H$^+$ 246.

4-Amino-7-cyclopropylmethoxy-6-methoxyquinazoline was reacted with 2,6-dimethylphenyl isothiocyanate using an analogous procedure to that described in the last paragraph of the portion of Example 1 which is concerned with the preparation of starting materials. There was thus obtained the required starting material: NMR Spectrum: (DMSOd$_6$) 0.39 (m, 2H), 0.61 (m, 2H), 1.32 (m, 1H), 2.25 (s, 6H), 4.0 (m, 5H), 7.17 (s, 3H), 7.25 (s, 1H), 8.17 (s, 1H), 8.72 (s, 1H), 11.08 (br s, 1H), 13.67 (s, 1H); Mass Spectrum: M+H$^+$ 409.

[42] The product gave the following data: NMR Spectrum: (CDCl$_3$) 0.42 (m, 2H), 0.69 (m, 2H), 1.44 (m, 1H), 2.3 (s, 6H), 3.32 (s, 3H), 3.62 (br s, 2H), 3.77 (m, 2H), 4.02 (d, 5H), 4.65 (br, 1H), 7.15 (s, 1H), 7.17 (s, 3H), 7.88 (br s, 1H), 8.57 (s, 1H), 12.52 (br s, 1H); Mass Spectrum: M+H$^+$ 450.

[43] The product gave the following data: NMR Spectrum: (DMSOd$_6$) 0.36 (m, 2H), 0.58 (m, 2H), 1.23–1.31 (m, 1H), 2.22 (s, 6H) 2.24 (s, 6H), 2.32–2.66 (m, 2H), 3.55 (m, 2H), 3.75 (br s, 3H), 3.96 (d, 2H), 7.04 (s, 1H), 7.16 (s, 3H), 7.55 (br s, 1H), 8.38 (s, 1H); Mass Spectrum: M+H$^+$ 463.

[44] The product gave the following data: NMR Spectrum: (DMSOd$_6$, 100° C.) 1.1 (t, 3H), 1.72 (m, 4H), 2.27 (s, 6H), 2.64 (m, 4H), 2.9 (m, 2H), 3.52 (q, 2H), 3.65 (s, 4H), 3.75 (s, 3H), 4.23 (m, 2H), 7.07 (s, 1H), 7.17 (s, 3H), 7.56 (s, 1H), 8.42 (s, 1H), 10.3–10.8 (br s, 1H); Mass Spectrum: M+H$^+$ 507.

The 1-(2,6-dimethylphenyl)-3-[6-methoxy-7-(2-pyrrolidin-1-ylethoxy)quinazolin-4-yl]thiourea used as a starting material was prepared as follows:—

4-(4-Bromo-2-fluorophenoxy)-7-hydroxy-6-methoxyquinazoline was reacted with 2-pyrrolidin-1-ylethyl chloride using an analogous procedure to that described in the third last paragraph of Note [15] above to give 4-(2-bromo-4-fluorophenoxy)-6-methoxy-7-(2-pyrrolidin-1-ylethoxy)quinazoline; NMR Spectrum: (CDCl$_3$) 1.83 (m, 4H), 2.69 (m, 4H), 3.06 (t, 2H), 4.04 (s, 3H), 4.34 (t, 2H), 7.21 (t, 1H), 7.31 (s, 1H), 7.4 (t, 2H), 7.53 (s, 1H), 8.6 (s, 1H); Mass Spectrum: M+H$^+$ 462 & 464.

Using an analogous procedure to that described in the second last paragraph of the portion of Example 1 that is concerned with the preparation of starting materials, 4-(2-bromo-4-fluorophenoxy)-6-methoxy-7-92-pyrrolidin-1-ylethoxy)quinazoline was reacted with ammonia to give 4-amino-6-methoxy-7-(2-pyrrolidin-1-ylethoxy)quinazoline; NMR Spectrum: (CDCl$_3$) 1.7 (s, 4H), 2.5 (m, 4H), 2.83 (t, 2H), 3.87 (s, 3H), 4.19 (t, 2H), 7.07 (s, 1H), 7.39 (s, 2H), 7.56 (s, 1H), 8.23 (s, 1H), Mass Spectrum: M+H$^+$ 289.

4-Amino-6-methoxy-7-(2-pyrrolidin-1-ylethoxy)quinazoline was reacted with 2,6-dimethylphenyl isothiocyanate using an analogous procedure to that described in the last paragraph of the portion of Example 1 which is concerned with the preparation of starting materials. There was thus obtained the required starting material: NMR Spectrum: (CDCl$_3$) 1.78 (m, 4H), 1.95 (br s, 2H), 2.28 (s, 6H), 2.64 (br t, 4H), 2.99 (t, 2H), 3.98 (s, 3H), 4.27 (t, 2H), 7.05 (s, 1H), 7.08–7.17 (m, 3H), 7.26 (s, 1H), 7.97 (s, 1H), 8.64 (s, 1H), 13.34 (s, 1H); Mass Spectrum: M+H$^+$ 452.

[45] The product gave the following data: NMR Spectrum: (DMSOd$_6$, 100° C.) 1.44 (m, 2H), 1.78 (m, 3H), 1.96 (m, 2H), 2.2 (s, 3H), 2.3 (s, 3H), 2.78 (m, 2H), 3.8 (s, 3H), 4.0 (d, 2H), 4.18 (m, 2H), 5.14 (m, 1H), 5.3 (m, 1H), 6.0–6.1 (m, 1H), 7.12 (s, 1H), 7.2–7.32 (m, 4H), 7.64 (s, 1H), 7.96 (m, 1H), 8.44 (s, 1H), 10.7 (s, 1H); Mass Spectrum: M+H$^+$ 475.

The 1-(2-methylphenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy)quinazoline was reacted with 2-methylphenyl isothiocyanate using an analogous procedure to that described in the last paragraph of the portion of Example 1 which is concerned with the preparation of starting materials. There was thus obtained the required starting material: Mass Spectrum: M+H$^+$ 452.

[46] The product gave the following data: NMR Spectrum: (DMSOd$_6$, 100° C.) 1.42 (m, 2H), 1.8 (m, 3H), 1.96 (t, 2H), 2.19 (s, 3H), 2.31 (s, 3H), 2.79 (m, 2H), 3.0 (s, 3H), 3.49 (t, 2H), 3.85 (s, 3H), 3.95 (m, 2H), 4.01 (d, 01), 7.11 (s, 1H), 7.2 (br s, 1H), 7.3 (m, 2H), 7.4 (d, 1H), 7.71 (s, 1H), 8.48 (s, 1H), 11.67 (br s, 1H); Mass Spectrum: M+H$^+$ 575 and 577.

[47] The product gave the following data: NMR Spectrum: (DMSOd$_6$, 100° C.) 1.22–1.43 (m, 11H), 1.67–1.95 (m, 5H), 2.13 (s, 3H), 2.27 (s, 6H), 2.77 (d, 2H), 3.8–4.0 (m, 7H), 6.52 (br s, 1H), 7.04 (s, 1H), 7.18 (s, 3H), 7.8 (s, 1H), 8.42 (s, 1H), 12.26 (s, 1H); Mass Spectrum: M+H$^+$ 563.

[48] The product gave the following data: NMR Spectrum: (DMSOd$_6$, 100° C.) 1.3–1.5 (m, 2H), 1.7–1.82 (m, 3H), 1.82–1.95 (m, 2H), (s, 3H), 2.24 (s, 6H), 2.75 (d, 2H), 3.35–3.5 (m, 3H), 3.62–3.8 (m, 5H), 3.95 (m, 2H), 4.35 (br s, 1H), 7.03 (br s, 1H), 7.14 (br s, 3H), 7.52 (s, 1H), 8.41 (br s, 1H); Mass Spectrum: M+H$^+$ 523.

[49] The product gave the following data: NMR Spectrum: (CDCl$_3$) 2.13 (m, 2H), 2.29 (s, 6H), 2.48 (m, 4H), 2.57 (t, 2H), 3.63 (s, 3H), 3.73 (m, 2H), 4.0 (s, 3H), 4.26 (t, 2H), 4.7 (s, 1H), 7.19 (m, 4H), 7.88 (s, 1H), 8.57 (s, 1H), 12.5 (s, 1H); Mass Spectrum: M+H$^+$ 551.

[50] The product gave the following data: NMR Spectrum: (DMSOd$_6$, 100° C.) 1.4 (s, 9H), 1.72 (m, 4H), 2.31 (s, 6H), 2.6 (m, 4H), 2.9 (t, 2H), 3.88 (s, 3H), 4.06 (d, 2H), 4.25 (t, 2H), 6.75 (br s, 1H), 7.07 (s, 1H), 7.17 (s, 3H), 7.75 (s, 1H), 8.47 (s, 1H), 11.4–11.8 (br s, 1H); Mass Spectrum: M+H$^+$ 549.

[51] The product gave the following data: NMR Spectrum: (DMSOd$_6$, 100° C.) 1.41 (m, 2H), 1.79 (m, 3H), 1.93 (t, 2H), 2.21 (s, 3H), 2.3 (s 3H), 2.77 (m, 4H), 3.71 (s, 3H), 3.78 (q, 2H), 3.99 (d, 2H), 6.73 (s, 1H), 6.84 (s, 1H), 7.08 (s, 1H), 7.22–7.31 (m, 2H), 7.39–7.53 (m, 4H), 8.3 (br s, 1H), 8.41 (s, 1H); Mass Spectrum: M+H$^+$ 563 and 565.

[52] The product gave the following data: NMR Spectrum: (DMSOd$_6$, 100° C) 1.41 (m, 2H), 1.79 (m, 3H), 1.98 (t, 2H), 2.2 (s, 3H), 2.3 (s, 3H), 2.79 (d, 2H), 3.2 (t, 2H), 3.75 (s, 3H), 3.91 (q, 2H), 4.0 (d, 2H), 7.1 (s, 1H), 7.15–7.33 (m, 4H), 7.41 (d, 1H), 7.58 (s, 1H), 7.7 (m, 1H), 8.11 (br s, 1H), 8.4 (s, 1H), 8.46 (d, 1H), 10.67 (br s, 1H): Mass Spectrum: M+H$^+$ 574 and 576.

[53] The product gave the following data: NMR Spectrum: (DMSOd$_6$, 100° C.) 1.41 (m, 2H), 1.77 (d, 3H), 1.94 (t, 2H), 2.2 (s, 3H), 2.3 (s, 3H), 2.78 (d, 2H), 3.01 (m, 2H), 3.7 (s, 3H), 3.78 (q, 2H), 4.0 (d, 2H), 7.08 (s, 1H), 7.18–7.36 (m, 7H), 7.41 (d, 1H), 7.49 (s, 1H), 8.3 (br s, 1H), 8.4 (s, 1H), 10.4 (br s, 1H); Mass Spectrum: M+H$^+$ 573 and 575.

[54] The product gave the following data: NMR Spectrum: (CDCl$_3$) 2.14 (m, 2H), 2.25 (s, 6H), 2.49 (m, 4H), 2.58 (t, 2H), 3.73 (t, 4H), 4.1 (s, 3H), 4.27 (t, 2H), 4.82 (d, 1H), 4.9 (d, 2H), 6.87 (t, 3H), 7.06 (s, 1H), 7.18 (m, 3H), 8.1 (s, 1H), 8.55 (s, 1H), 12.71 (s, 1H); Mass Spectrum: M+H$^+$ 591.

[55] The product gave the following data: NMR Spectrum: (DMSOd$_6$, 100° C.) 1.3–1.5 (m, 2H), 1.64–2.04 (m, 10H), 2.15 (s, 3H), 2.25 (s, 6H), 2.74 (d, 2H), 3.5–3.9 (m, 8H), 3.95 (d, 2H), 4.14 (m, 1H), 7.02 (s, 1H), 7.14 (s, 3H), 7.44 (s, 1H), 8.41 (s, 1H); Mass Spectrum: M+H$^+$ 533.

[56] The product gave the following data: NMR Spectrum: (DMSOd$_6$, 100° C.) 1.5 (m, 1H), 1.67 (m, 4H), 1.83 (m, 4H), 1.96 (m, 1H), 2.26 (s, 6H), 2.6 (m, 4H), 2.9 (t, 2H), 3.5–3.8 (m, 4H), 3.75 (s, 3H), 4.18 (m, 1H), 4.21 (t, 2H), 7.06 (s, 1H), 7.17 (s, 3H), 7.52 (s, 1H), 8.47 (s, 1H), 10.0 . 10.8 (br s, 1H); Mass Spectrum: M+H$^+$ 519.

[57] The 2-aminomethyl-1,4dioxane, used as a starting material was obtained using the procedure described in *Chemical Abstracts,* volume 132, abstract 293722. The product gave the following data: NMR Spectrum: (DMSOd$_6$, 100° C.) 1.72 (m, 4H), 1.99 (m, 2H), 2.56 (m, 4H), 2.62 (t, 2H), 3.41 (m, 1H), 3.5–3.62 (m, 4H), 3.66–3.78 (m, 4H), 3.83–3.92 (m, 3H), 4.2 (t, 2H), 7.11 (s, 1H), 7.2 (m, 2H), 7.34–7.44 (m, 2H), 8.49 (s, 1H), 9.09 (br s, 1H), 9.83 (br s, 1H); Mass Spectrum: M+H$^+$ 557.

[58] The product gave the following data: NMR Spectrum: (DMSOd$_6$, 100° C.) 1.34–1.54 (m, 8H), 1.78 (m, 3H), 1.95 (t, 2H), 2.2 (s, 3H), 2.34 (s, 3H), 2.5 (m, 4H), 2.62 (t, 2H), 2.79 (d, 2H), 3.61 (q, 2H), 3.73 (s, 3H), 3.99 (d, 2H), 7.11 (s, 1H), 7.24 (m, 1H), 7.31 (m, 1H), 7.42 (m, 2H), 8.46 (s, 1H), (s, 1H), 10.63 (s, 1H); Mass Spectrum: M+H$^+$ 580 and 582.

[59] The product gave the following data: NMR Spectrum: (DMSOd$_6$, 100° C.) 1.4 (m, 2H), 1.78 (m, 3H), 1.88 (m, 2H), 1.97 (t, 2H), 2.2 (s, 3H), 2.32 (s, 3H), 2.39 (t, 4H), 2.44 (t, 2H), 3.58 (m, 6H), 3.8 (d, 2H), 3.74 (s, 3H), 3.99 (d, 2H), 7.08 (s, 1H), 7.21–7.33 (m, 2H), 7.41 (m, 2H), 8.4 (br s, 1H), 8.42 (s, 1H), 10.28 (br s, 1H); Mass Spectrum: M+H$^+$ 596 and 598.

[60] The product gave the following data: NMR Spectrum: (DMSOd$_6$, 100° C.) 0.41 (m, 2H), 0.62 (m, 2H), 1.3(m, 1H), 1.33–1.47 (m, 6H), 2.27 (s, 6H), 2.43 (m, 4H), 2.55 (m, 2H), 3.57 (m, 2H), 3.75 (s, 3H), 3.97 (d, 2H), 7.04 (s, 1H), 7.16 (s, 3H), 7.59 (s, 1H), 8.43 (s, 1H); Mass Spectrum: M+H$^+$ 503.

[61] The product gave the following data: NMR Spectrum: (DMSOd$_6$, 100° C.) 0.38 (m, 2H), 0.59 (m, 2H), 1.28 (m, 1H), 2.28 (s, 6H), 2.46 (m, 4H), 2.62 (m, 2H), 3.53 (m, 4H), 3.64 (br m, 2H), 3.79 (s, 3H), 3.98 (d, 2H), 7.05 (s, 1H) 7.17 (s, 3H), 7.6 (s, 1H), 8.42 (s, 1H); Mass Spectrum: M+H$^+$ 505.

[62] The product gave the following data: NMR Spectrum: (DMSOd$_6$, 100° C.) 0.38 (m, 2H), 0.59 (m, 2H), 1.27 (m, 1H), 1.84 (m, 2H), 2.27 (s, 6H), 2.37 (m, 4H), 3.48–3.58 (m, 6H), 3.77 (s, 3H), 3.98 (d, 2H), 7.05 (s, 1H), 7.15 (s, 3H), 7.57 (s, 1H), 8.4 (s, 1H); 8.4 (s, 1H); Mass Spectrum: M+H$^+$ 519.

[63] The product gave the following data: NMR Spectrum: (DMSOd$_6$, 100° C.) 1.89 (m, 4H), 2.09 (t, 2H), 2.29 (s, 6H), 2.54 (t, 4H), 3.3 (t, 2H), 3.37 (t, 2H), 3.49 (q, 2H), 3.6 (t, 4H), 3.8 (s, 3H), 4.6 (t, 2H), 7.11 (s, 1H), 7.19 (s, 3H), 7.30 (br s, 1H), 7.61 (s, 1H), 8.43 (s, 1H), 10.8 (br s, 1H); Mass Spectrum: M+H$^+$ 576.

[64] The product gave the following data: NMR Spectrum: (DMSOd$_6$, 100° C.) 1.39 (m, 2H), 1.77 (m, 3H), 1.93 (t, 2H), 2.17 (s, 3H), 2.31 (s, 3H), 2.57 (m, 2H), 2.77 (m, 2H), 3.22 (m, 1H), 3.36–3.9 (m, 9H), 3.96 (d, 2H), 7.09 (s, 1H), 7.23 (t, 1H), 7.3 (d, 1H), 7.39 (d, 1H), 7.47 (s, 1H), 8.18 (br s, 1H), 8.42 (s, 1H), 10.4 (br s, 1H); Mass Spectrum: M+H$^+$ 569 and 571.

[65] The product gave the following data: NMR Spectrum: (DMSOd$_6$, 100° C.) 1.41 (m, 2H), 1.78 (d, 3H), 1.96 (t, 2H), 2.19 (s, 3H), 2.27 (s, 6H), 2.79 (m, 2H), 3.0 (s, 3H), 3.49 (t, 2H), 3.89 (s, 3H), 3.95 (m, 2H), 4.01 (d, 2H), 6.56 (br s, 1H), 7.1 (s, 1H), 7.2 (m, 3H), 7.8 (s, 1H), 8.47 (s, 1H), 11.72 (br s, 1H); Mass Spectrum: M+H$^+$ 555.

[66] The product gave the following data: NMR Spectrum: (DMSOd$_6$, 100° C.) 1.3–1.5 (m, 2H), 1.64–2.04 (m, 10H), 2.15 (s, 3H), 2.25 (s, 6H), 2.74 (d, 2H), 3.5–3.9 (m, 8H), 3.95 (d, 2H), 4.14 (m, 1H), 7.02 (s, 1H), 7.14 (s, 3H), 7.44 (s, 1H), 8.41 (s, 1H); Mass Spectrum: M+H$^+$ 533.

[67] The product gave the following data: Mass Spectrum: M+H$^+$ 533.

[68] The product gave the following data: Mass Spectrum: M+H$^+$ 592.

[69] The product gave the following data: NMR Spectrum: (DMSOd$_6$, 100° C.) 1.4 (m, 2H), 1.58 (m, 3H), 1.65–1.8 (m, 8H), 1.98 (t, 2H), 2.2 (s, 3H), 2.33 (s, 3H), 2.8 (d, 2H), 3.52 (q, 2H), 3.73 (s, 3H), 4.0 (d, 2H), 7.1 (s, 1H), 7.28 (m, 2H), 7.41 (m, 2H), 8.3 (br s, 1H), 8.45 (s, 1H), 10.25 (br s, 1H); Mass Spectrum: M+H$^+$ 564 and 566.

[70] The product gave the following data: NMR Spectrum: (DMSOd$_6$, 100° C.) 1.18 (s, 6H), 1.6 (m, 2H), 1.97 (d, 3H), 2.25 (t, 2H), 2.4 (s, 3H), 2.51 (s, 3H), 2.99 (d, 2H), 3.51 (s, 2H), 3.62 (d, 2H), 3.9 (s, 3H), 4.26 (d, 2H), 4.71 (s, 1H), 7.21 (s, 1H), 7.4–7.61 (m, 4H), 8.63 (s, 1H); Mass Spectrum: M+H$^+$ 555 and 557.

[71] The product gave the following data: NMR Spectrum: (DMSOd$_6$, 100° C.) 1.41 (m, 2H), 1.52 (m, 2H), 1.6 (m, 2H), 1.79 (d, 3H), 1.92–2.07 (m, 4H), 2.2 (s, 3H), 2.31 (m, 5H), 2.79 (d, 2H), 3.61 (q, 2H), 3.72 (s, 3H), 4.0 (d, 2H), 5.53 (s, 1H), 7.09 (s, 1H), 7.23–7.33 (m, 2H), 7.4 (d, 1H), 7.45 (s, 1H), 8.43 (s, 1H); Mass Spectrum: M+H$^+$ 577 and 579.

[72] The product gave the following data: NMR Spectrum: (DMSOd$_6$, 100° C.) 1.38 (s, 9H), 1.72 (m, 4H), 1.92 (m, 2H), 1.97 (m, 2H), 2.61 (t, 2H), 2.8 (s, 3H), 2.83 (s, 3H), 3.34 (t, 2H), 3.52 (q, 2H), 3.78 (s, 3H), 4.19 (t, 2H), 7.07 (s, 1H), 7.24–7.34 (m, 2H), 7.42 (m, 1H), 7.49 (br s, 1H), 8.0–8.3 (br s, 1H), 8.44 (s, 1H), 10.3–10.7 (br s, 1H); Mass Spectrum: M+H$^+$ 640 and 642.

[73] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.39 (s, 9H), 1.41 (s, 3H), 1.9 (m, 2H), 2.31 (s, 3H), 2.56 (t, 4H), 2.8 (t, 2H), 3.33 (t, 2H), 3.52 (q, 2H), 3.6 (t, 4H), 3.8 (s, 3H), 4.27 (t, 2H), 7.12 (s, 1H), 7.2 (t, 1H), 7.27 (t, 1H), 7.31 (d, 2H), 7.64 (s, 1H), 8.46 (s, 1H); Mass Spectrum: M+H$^+$ 608.

The 1-(2-methylphenyl)-3-[6-methoxy-7-(2-morpholinoethoxy)quinazolin-4-yl]thiourea used as a starting material was prepared as follows:—

4-Amino-6-methoxy-7-(2-morpholinoethoxy)quinazoline was reacted with 2-methylphenyl isothiocyanate using an analogous procedure to that described in the last paragraph of the portion of Example 1 which is concerned with the preparation of starting materials. There was thus obtained the required starting material; NMR Spectrum: (CDCl$_3$) 2.44 (s, 3H), 2.66 (t, 4H), 2.96 (t, 2H), 3.76 (t, 4H), 4.09 (s, 3H), 4.37 (t, 2H), 7.11 (s, 1H), 7.33 (m, 4H), 7.76 (d, 1H), 8.71 (s, 1H), 8.86 (s, 1H), 13.73 (s, 1H); Mass Spectrum: M+H$^+$ 454.

[74] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.8 (m, 2H), 2.1 (s, 6H), 2.34 (s, 3H), 2.39 (t, 2H), 2.57 (t, 4H), 2.82 (t, 2H), 3.61 (m, 6H), 3.82 (s, 3H), 4.29 (t, 2H), 7.15(s, 1H), 7.23 (t, 1H), 7.3 (t, 1H), 7.36 (d, 2H), 7.69 (s, 1H), 8.47 (s, 1H); Mass Spectrum: M+H$^+$ 522.

[75] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.79 (m, 2H), 2.1 (s, 6H), 2.34 (s, 3H), 2.39 (t, 2H), 2.58 (t, 4H), 2.82 (t, 2H), 3.6 (t, 6H), 3.77 (s, 3H), 4.26 (t, 2H), 7.11 (s, 1H), 7.28 (t, 1H), 7.33 (d, 1H), 7.42 (d, 1H), 7.53 (s, 1H), 8.47, (s, 1H); Mass Spectrum: M+H$^+$ 556 and 558.

[76] THF was used as the reaction solvent in place of a 1:1 mixture of chloroform and methanol and the reaction was heated to reflux for 2 hours. The product gave the following data: NMR Spectrum:(DMSOd$_6$, 100° C.) 1.39 (s, 9H), 1.91 (m, 2H), 2.33 (s, 3H), 2.55 (t, 4H), 2.8 (t, 2H), 2.84 (s, 3H), 3.32 (t, 2H), 3.53 (q, 2H), 3.6 (t, 4H), 3.77 (s, 3H), 4.27 (t, 2H), 7.11 (s, 1H), 7.26 (t, 1H), 7.32 (d, 1H), 7.41 (d, 1H), 7.5 (s, 1H), 8.46 (s, 1H); Mass Spectrum: M+H$^+$ 642 and 644.

[77] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.81 (m, 2H), 2.14 (s, 6H), 2.4 (t, 2H), 2.56 (t, 4H), 2.81 (t, 2H), 3.6 (m, 6H), 3.81 (s, 3H), 4.29, (t, 2H), 7.14 (s, 1H), 7.29 (t, 1H), 7.41 (t, 1H), 7.57 (d, 1H), 7.61 (d, 2H), 8.49 (s, 1H), 8.6, (br s, 1H); Mass Spectrum: M+H$^+$ 542 and 544.

The 1-(2-chlorophenyl)-3-[6-methoxy-7-(2-morpholinoethoxy)quinazolin-4-yl]thiourea used as a starting material was prepared as follows:—

4-Amino-6-methoxy-7-(2-morpholinoethoxy)quinazoline was reacted with 2-chlorophenyl isothiocyanate using an analogous procedure to that described in the last paragraph of the portion of Example 1 which is concerned with the preparation of starting materials. There was thus obtained the required starting material; NMR Spectrum: (CDCl$_3$) 2.65 (t, 4H), 2.99 (t, 2H), 3.77 (t, 4H), 4.07 (s, 3H), 4.35 (t, 2H), 7.11 (s, 1H), 7.26 (m, 1H), 7.36 (m, 2H), 7.52 (d,1H), 8.4 (d, 1H), 8.76 (s, 1H), 14.37 (s, 1H); Mass Spectrum: M+H$^+$ 474 and 476.

THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 2.3 (s, 6H), 2.53 (t, 4H), 2.64 (t, 2H), 2.81 (t, 2H), 3.6 (m, 6H), 3.7 (s, 3H), 4.25 (t, 2H), 7.12 (s, 1H), 7.33 (m, 2H), 7.57 (m, 2H), 8.47 (s, 1H), 9.0 (br s, 1H); Mass Spectrum: M+H$^+$ 562 and 564.

The 1-(2,6-dichlorophenyl)-3-[6-methoxy-7-(2-morpholinoethoxy)quinazolin-4-yl]thiourea used as a starting material was prepared as follows:—

4-Amino-6-methoxy-7-(2-morpholinoethoxy)quinazoline was reacted with 2,6-dichlorophenyl isothiocyanate using an analogous procedure to that described in the last paragraph of the portion of Example 1 which is concerned with the preparation of starting materials. There was thus obtained the required starting material; NMR Spectrum: (CDCl$_3$) 2.68 (t, 4H), 2.97 (t, 2H), 3.75 (t, 4H), 4.06 (s, 3H), 4.38 (t, 2H), 7.17 (s, 1H), 7.31 (d, 1H), 7.47 (t, 2H), 8.03 (s, 1H), 8.75 (s, 1H), 9.09 (s, 1H), 13.72 (s, 1H); Mass Spectrum: M+H$^+$ 508 and 510.

[79] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.83 (m, 2H), 2.15 (s, 6H), 2.4 (t, 2H), 2.57 (t, 4H), 2.81 (t, 2H), 3.58 (m, 6H), 3.37 (s, 3H), 4.25 (t, 2H), 7.12 (s, 1H), 7.36 (t, 1H), 7.42 (s, 1H), (d, 2H), 8.47 (s, 1H), 8.8 (br s, 1H); Mass Spectrum: M+H$^+$ 576 and 578.

[80] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.4 (s, 9H), 1.91 (m, 2H), 2.55 (t, 4H), 2.79 (t, 2H), 2.83 (s, 3H), 3.35 (t, 2H), 3.52 (q, 2H), 3.61 (t, 4H), 3.75 (s, 3H), 4.29 (t, 2H), 7.14 (s, 1H), 7.38 (s, 1H), 7.44 (s, 1H), 7.58 (d, 2H), 8.47 (s, 1H); Mass Spectrum: M+H$^+$ 662 and 664.

[81] The product gave the following data: NMR Spectrum: (DMSOd$_6$, 100° C.) 0.98 (d, 3H), 2.2 (s, 6H), 2.27 (s, 6H), 2.52 (t, 4H), 2.79 (t, 2H), 2.88 (m, 1H), 3.49–3.52 (m, 2H), 3.59 (t, 4H), 3.76 (s, 3H), 4.23 (m, 2H), 7.1 (s, 1H), 7.16 (m, 3H), 7.54 (s, 1H), 8.41, (s, 1H), 10.67 (br s, 1H); Mass Spectrum: M+H$^+$ 536.

[82] The product gave the following data: NMR Spectrum: (DMSOd$_6$, 100° C.) 1.76 (m, 2H), 2.08 (s, 6H), 2.29 (s, 6H), 2.37 (t, 2H), 3.6 (t, 2H), 3.82 (s, 3H), 5.28 (s, 2H), 7.2 (m, 4H), 7.34 (m, 1H), 7.41 (m, 2H), 7.5 (d, 2H), 7.69 (s, 1H), 8.44 (s, 1H), 8.44 (s, 1H), 10.8 (br s, 1H); Mass Spectrum: M+H$^+$ 513.

The 1-(7-benzyloxy-6-methoxyquinazolin-4-yl)-3-(2,6-dimethylphenyl)thiourea used as a starting material was prepared as follows:—

A mixture of 7-benzyloxy-6-methoxy-3,4-dihydroquinazolin-4-one (International Patent Application WO 97/22596, Example 1 thereof; 25.1 g), thionyl chloride (450 ml) and DMF (1 ml) was stirred and heated to reflux for 2 hours. The mixture was evaporated and the residue was dissolved in toluene and the solution was evaporated. The resultant solid was suspended in methylene chloride (500 ml), solid potassium carbonate (39 g) was added and the mixture was stirred for 10 minutes. Water (500 ml) was added and the mixture stirred for another 10 minutes. The methylene chloride layer was separated, dried over magnesium sulphate and evaporated. The residue was purified by column chromatography on silica using increasingly polar mixtures of methylene chloride and ethyl acetate as eluent. There was thus obtained 7-benzyloxy-4-chloro-6-methoxyquinazoline (21.54 g); NMR Spectrum: (DMSO$_6$) 4.0 (s, 3H), 5.36 (s, 2H), 7.31–7.46 (m, 4H), 7.51 (d, 2H), 7.58 (s, 1H), 8.88 (s, 1H).

A portion (3 g) of the material so obtained was dissolved in a 1M solution of ammonia in isopropanol (50 ml). Liquid ammonia (5 ml) was added and the reaction mixture was sealed in a Carius tube. The reaction mixture was heated to 120° C. for 60 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-7-benzyloxy-6-methoxyquinazoline (2.65 g); NMR Spectrum: (DMSOd$_6$) 3.88 (s, 3H), 3.9 (s, 3H), 7.2 (s, 1H), 7.63 (s, 2H), 7.69 (s, 1H), 8.38 (s, 1H); Mass Spectrum: M+H$^+$ 230.

4-Amino-7-benzyloxy-6-methoxyquinazoline was reacted with 2,6-dimethylphenyl isothiocyanate using an analogous procedure to that described in the last paragraph of the portion of Example 1 which is concerned with the preparation of starting materials. There was thus obtained the required starting material; NMR Spectrum: (DMSOd$_6$) 2.22 (s, 6H), 4.0 (s, 3H), 5.33 (s, 2H), 7.14 (m, 3H), 7.31–7.54 (m, 6H), 8.2 (s, 1H), 8.7 (s, 1H), 11.12 (s, 1H), 13.69 (s, 1H).

[83] The product gave the following data: NMR Spectrum: (DMSOd$_6$, 100° C.) 2.24 (s, 6H), 2.29 (s, 6H), 2.57 (t, 2H), 3.6 (q, 2H), 3.8 (s, 3H), 5.28 (s, 2H), 7.19 (m, 4H), 7.34 (t, 1H) 7.41 (t, 2H), 7.5 (t, 2H), 7.62 (s, 1H), 8.43 (s, 1H); Mass Spectrum: M+H$^+$ 499.

[84] The product gave the following data: NMR Spectrum: (CDCl$_3$) 0.87 (d, 6H), 1.85 (m, 2H), 2.12 (m, 2H), 2.31 (s, 6H), 2.5 (t, 4H), 2.58 (t, 2H), 2.75 (m, 3H), 3.72 (m, 6H), 4.03 (s, 3H), 4.25 (t, 2H), 5.17 (m, 1H), 7.15 (s, 3H), 7.18 (s, 1H), 7.86 (s, 1H), 8.57 (s, 1H), 12.5 (s, 1H); Mass Spectrum: M+H$^+$ 564.

[85] The product gave the following data: NMR Spectrum: (DMSOd$_6$, 100° C.) 1.54 (m, 2H), 1.64–1.78 (m, 4H), 2.27 (s, 6H), 2.47 (t, 2H), 2.54 (t, 4H), 2.8 (t, 2H), 3.52 (q, 2H), 3.61 (t, 4H), 3.77 (s, 3H), 4.26 (t, 2H), 7.11(s, 1H), 7.18 (s, 3H), 7.58 (s, 1H), 8.43 (s, 1H), 10.5 (br s, 1H); Mass Spectrum: M+H$^+$ 546.

[86] The product gave the following data: NMR Spectrum: (DMSOd$_6$, 100° C.) 0.94 (s, 6H), 2.28 (s, 6H), 2.55 (t, 4H), 2.8 (t, 2H), 3.29 (s, 2H), 3.47 (d, 2H), 3.61 (t, 4H), 3.73 (s, 3H), 4.25 (t, 2H), 4.5 (s, 1H), 7.1 (s, 1H), 7.17 (s, 3H), 7.5 (s, 1H), 8.44 (s, 1H), 10.2 (br s, 1H); Mass Spectrum: M+H$^+$ 537.

[87] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 2.29 (s, 6H), 2.32 (s, 3H), 2.55 (t, 4H), 2.6 (t, 2H), 2.8 (t, 2H), 3.61 (m, 6H), 3.8 (s, 3H), 4.26 (t, 2H), 7.14 (s, 1H), 7.2 (t, 1H), 7.28 (t, 1H), 7.36 (t, 2H), 7.67 (s, 1H), 7.85 (br s, 1H), 8.48 (s, 1H); Mass Spectrum: M+H$^+$ 508.

[88] The product gave the following data: NMR Spectrum: (DMSOd$_6$, 100° C.) 1.53 (m, 4H), 1.99 (d, 4H), 2.27 (m, 10H), 2.57 (t, 4H), 2.8 (t, 2H), 3.58 (t, 4H), 3.79 (s, 3H), 4.25 (t, 2H), 5.46 (s, 1H), 7.11 (s, 1H), 7.19 (s, 3H), 7.6 (s, 1H), 8.42 (s, 1H), 10.7 (br s, 1H); Mass Spectrum: M+H$^+$ 559.

[89] The product gave the following data: NMR Spectrum: (DMSOd$_6$, 100° C.) 1.78 (m, 2H), 2.06 (s, 6H), 2.28 (s, 6H), 2.35 (t, 2H), 3.6 (t, 2H), 3.83 (s, 3H), 5.31 (s, 2H), 7.2 (s, 4H), 7.32 (t, 2H), 7.55 (d, 1H), 7.68 (s, 1H), 7.8 (t, 1H), 8.41 (s, 1H), 8.59 (d, 1H), 10.8 (br s, 1H); Mass Spectrum: M+H$^+$ 514.

The 1-(2,6-dimethylphenyl)-3-[6-methoxy-7-(2-pyridylmethoxy)quinazolin-4-yl]thiourea used as a starting material was prepared as follows:—

A mixture of 4-(4-bromo-2-fluorophenoxy)-7-hydroxy-6-methoxyquinazoline (9.0 g), 2-pyridylmethyl chloride hydrochloride (4.49 g), anhydrous potassium carbonate (17.2 g) and NMP (100 ml) was stirred and heated to 85° C. for 16 hours. About half of the solvent was evaporated and the resulting slurry was poured into water (900 ml). The mixture was stirred for two hours and the resultant precipitate was isolated. There was thus obtained 4-(4-bromo-2-fluorophenoxy)-6-methoxy-7-(2-pyridylmethoxy)quinazoline (9.72 g); NMR Spectrum: (CDCl$_3$) 4.11 (s, 3H), 5.47 (s, 2H), 7.27 (m, 2H), 7.42 (m, 3H), 7.6 (d, 2H), 7.76 (m, 1H), 8.6 (s, 1H), 8.66 (s, 1H); Mass Spectrum: M+H$^+$ 456 and 458.

Using an analogous procedure to that described in the second last paragraph of starting materials, 4-(4-bromo-2-fluorophenoxy)-6-methoxy-7-(2-pyridylmethoxy)quinazoline was reacted with ammonia in isopropanol. There was thus obtained 4-amino-6-methoxy-7-(2-pyridylmethoxy) quinazoline; NMR Spectrum: (DMSOd$_6$) 3.9 (s, 3H), 5.31 (s, 2H), 7.13 (s, 1H), 7.39 (m, 3H), 7.56 (d, 1H), 7.62 (s, 1H), 7.86 (m, 1H), 8.24 (s, 1H), 8.61 (d, 1H); Mass Spectrum: M+H$^+$ 283.

The material so obtained was reacted with 2,6-dimethylphenyl isothiocyanate using an analogous procedure to that described in the last paragraph of the portion of Example 1 which is concerned with the preparation of starting materials. There was thus obtained the required starting material; NMR Spectrum: (DMSOd$_6$) 2.23 (s, 6H), 4.04 (s, 3H), 5.4 (s, 2H), 7.14 (s, 3H), 7.39 (m, 2H), 7.59 (d, 1H), 7.88 (m, 1H), 8.21 (s, 1H), 8.61 (d, 1H), 8.69 (d, 1H), 11.14 (s, 1H), 13.67 (s, 1H); Mass Spectrum: M+H$^+$ 446.

[90] The product gave the following data: NMR Spectrum: (DMSOd$_6$, 100° C.) 2.27 (d, 12H), 2.6 (t, 2H), 3.6 (t, 2H), 3.86 (s, 3H), 5.31 (s, 2H), 7.19 (m, 4H), 7.32 (m, 1H), 7.55 (d, 1H), 7.61 (s, 1H), 7.82 (t, 1H), 8.42 (s, 1H), 10.8 (br s, 1H); Mass Spectrum: M+H$^+$ 500.

[91] The product gave the following data: NMR Spectrum: (DMSOd$_6$, 100° C.) 1.52–1.7 (m, 4H), 1.8–1.94 (m, 2H), 2.01 (q, 1H), 2.1 (s, 3H), 2.28 (s, 7H), 2.75 (s, 1H), 3.52 (m, 1H), 3.66 (m, 1H), 3.86 (s, 3H), 5.32 (s, 2H), 7.19 (s, 4H), 7.31 (t, 1H), 7.54 (d, 1H), 7.71 (s, 1H), 7.82 (t, 1H), 8.43 (s, 1H), 8.6 (s, 1H), 11.1 (br s, 1H); Mass Spectrum: M+H$^+$ 540.

[92] The product gave the following data: NMR Spectrum: (DMSOd$_6$, 100° C.) 1.7 (m, 1H), 1.9 (m, 2H), 1.99 (m, 1H) 2.29 (s, 6H), 3.57 (m, 1H), 3.65 (m, 2H), 3.8 (m, 4H), 4.15 (m, 1H), 5.31 (s, 2H), 7.18 (s, 4H), 7.33 (m, 1H), 7.55 (d, 1H), 7.81 (t, 1H), 8.42 (s, 1H), 8.6 (d, 1H), 10.23 (br s, 1H); Mass Spectrum: M+H$^+$ 513.

[93] The product gave the following data: NMR Spectrum: (DMSOd$_6$, 100° C.) 1.69 (m, 1H), 1.88 (m, 2H), 1.99 (m, 1H), 2.29 (s, 6H), 3.52 (m, 1H), 3.65 (m, 2H), 3.79 (m, 3H), 3.84 (m, 1H), 4.15 (m, 1H), 5.31 (s, 2H), 7.19 (s, 4H), 7.33 (t, 1H), 7.54 (d, 2H), 7.81 (t, 1H), 8.43 (s, 1H), 8.6 (d, 1H), 10.25 (br s, 1H); Mass Spectrum: M+H$^+$ 513.

[94] The product gave the following data: NMR Spectrum: (DMSOd$_6$, 100° C.) 2.3 (s, 6H), 3.79 (s, 3H), 4.8 (d, 2H), 5.3 (s, 2H), 7.17 (s, 1H), 7.2 (s, 3H), 7.25 (m, 1H), 7.33 (m, 1H), 7.43 (d, 1H), 7.55 (m, 2H), 7.74 (t, 1H), 7.81 (t, 1H), 8.41 (s, 1H), 8.5 (d, 1H), 8.6 (d, 1H), 11.03 (br s, 1H); Mass Spectrum: M+H$^+$ 520.

[95] The product gave the following data: NMR Spectrum: (DMSOd$_6$, 100° C.) 2.28 (s, 6H), 3.34 (s, 3H), 3.62 (t, 2H), 3.7 (t, 2H), 3.8 (s, 3H), 5.32 (s, 2H), 7.19 (s, 4H), 7.32 (m, 1H), 7.54 (d, 1H), 7.6 (s, 1H), 7.82 (t, 1H), 8.42 (s, 1H), 8.59 (s, 1H), 10.54 (br s, 1H); Mass Spectrum: M+H$^+$ 487.

[96] The product gave the following data: NMR Spectrum: (DMSOd$_6$, 100° C.) 1.52 (m, 2H), 1.68 (m, 4H) 2.27 (s, 6H), 2.48 (m, 2H), 3.51 (q, 2H), 3.8 (s, 3H), 5.31 (s, 2H), 7.18 (s, 4H), 7.32 (t, 1H), 7.55 (d, 1H), 7.61 (s, 1H), 7.82 (t, 1H), 8.41 (s, 1H), 8.6 (d, 1H), 10.5 (br s, 1H); Mass Spectrum: M+H$^+$ 524.

[97] Glycine tert-butylamide (*J. Med. Chem.*, 1979, 22, 931) was used as the appropriate amine and 1,2-dimethoxyethane was used as a co-solvent. The product gave the following data; NMR Spectrum: (DMSOd$_6$, 100° C.) 1.22 (s, 9H), 1.24 (q, 2H), 1.7–2.0 (m, 5H), 2.14 (s, 3H), 2.29 (s, 6H), 2.77 (m, 2H), 3.86 (s, 3H), 3.92 (d, 2H), 3.99 (d, 2H), 7.08–7.13 (m, 2H), 7.19 (s, 3H), 7.33 (br s, 1H), 8.48 (s, 1H); Mass Spectrum: M+H$^+$ 562.

[98] Glycine isopropylamide (*J. Amer. Chem. Soc.*, 1967, 89, 6096was used as the appropriate amine. The product gave the following data: NMR Spectrum: (DMSOd$_6$, 100° C.) 1.04 (d, 6H), 1.36–1.48 (m, 2H), 1.77 (br d, 3H), 1.96 (br t, 2H), 2.19 (s, 3H), 2.28 (s, 6H), 2.78 (br d, 2H), 3.83 (s, 4H), 4.0 (m, 4H), 7.09 (s, 1H), 7.19 (s, 3H), 7.35(m, 1H), 7.7 (s, 1H), 8.45 (s, 1H); Mass Spectrum: M+H$^+$ 548.

[99] Glycine N-(2-dimethylaminoethyl)amide (*J. Amer. Chem. Soc.*, 1967, 89, 7123) was used as the appropriate amine. The product gave the following data: NMR Spectrum: (DMSOd$_6$, 100° C.) 1.3–1.44 (m, 2H), 1.68–1.84 (m, 3H), 1.86–1.95 (m, 2H), 2.02 (s, 6H), 2.15 (s, 3H), 2.2–2.3 (m, 2H), 2.26 (s, 6H), 2.76 (d, 2H), 3.12–3.2 (m, 2H), 3.84 (s, 3H), 3.96–4.02 (m, 4H), 7.06 (s, 1H), 7.16 (s, 3H), 7.4 (s, 1H), 8.46 (s, 1H); Mass Spectrum: M+H$^+$ 577.

[100] (S)-Alanine tert-butyl ester hydrochloride was treated with triethylamine to give the required amine. The product gave the following data: NMR Spectrum: (DMSOd$_6$, 100° C.) 1.3–1.46 (m, 14H), 1.72–1.8 (br d, 3H), 1.88–1.96 (m, 2H), 2.17 (s, 3H), 2.28 (s, 6H), 2.72–2.82 (br d, 2H), 3.88 s, 3H), 3.98 (d, 2H), 4.38 (m, 1H), 7.04 (s, 1H), 7.16 (s, 3H), 7.73 (s, 1H), 8.45 (s, 1H); Mass Spectrum: M+H$^+$ 577.

[101] (R)-Alanine tert-butyl ester hydrochloride was treated with triethylamine to give the required amine. The product gave the following data: NMR Spectrum: (DMSOd$_6$, 100° C.) 1.3–1.46 (m, 4H), 1.72–1.8 (br d, 3H), 1.88 –1.96 (m, 2H), 2.17 (s, 3H), 2.28 (s, 6H), 2.72–2.82 (br d, 2H), 3.88 (s, 3H), 3.98 (d, 2H), 4.38 (m, 1H), 7.04 (s, 1H), 7.16 (s, 3H), 7.73 (s, 1H), 8.45 (s, 1H); Mass Spectrum: M+H$^+$ 577.

[102] (S)-Alanine tert-butyl ester hydrochloride was treated with triethylamine to give the required amine. The product gave the following data: NMR Spectrum: (DMSOd$_6$, 100° C.) 1.36 (s, 9H), 1.42 (d, 3H), 1.72 (m, 4H), 2.32 (s, 6H), 2.65 (m, 4H), 2.91 (t, 2H), 3.88 (s, 3H), 4.24 (t, 2H), 4.48 (q, 1H), 7.12 (s, 1H), 7.19 (s, 3H), 7.77 (s, 1H), 8.47 (s, 1H), 11.4–11.75 (br s, 1H); Mass Spectrum: M+H$^+$ 563.

[103] (R)-Alanine tert-butyl ester hydrochloride was treated with triethylamine to give the required amine. The product gave the following data: NMR Spectrum: (DMSOd$_6$, 100° C.) 1.35 (s, 9H), 1.46 (d, 3H), 1.7 (m, 4H), 2.28 (s, 6H), 2.63 (m, 4H), 2.91 (t, 2H), 3.88 (s, 3H), 4.27 (t, 2H), 4.46 (quintet, 1H), 7.12 (s, 1H), 7.18 (s, 1H), 7.75 (s, 1H), 8.46 (s, 1H), 11.45–11.65 (br s, 1H); Mass Spectrum: M+H$^+$ 563.

[104] The product gave the following data: NMR Spectrum: (DMSOd$_6$, 100° C.) 1.4 (s, 9H), 2.3 (s, 6H), 2.54 (t, 4H), 2.8 (t, 2H), 3.6 (t, 4H), 3.89 (s, 3H), 4.02 (d, 2H), 4.28 (t, 2H), 7.11 (s, 1H), 7.19 (s, 3H), 7.78 (s, 1H), 8.48 (s, 1H), 11.6 (br s, 1H); Mass Spectrum: M+H$^+$ 565.

[105] Glycine isopropylamide was used as the appropriate amine. The product gave the following data: NMR Spectrum: (DMSOd$_6$, 100° C.) 1.05 (d, 6H), 2.27 (s, 6H), 2.48–2.52 (m, 4H), 2.78 (t, 2H), 3.56–3.62 (m, 4H), 3.82–3.9 (m, 4H), 4.02 (d, 2H), 4.25 (t, 2H), 7.15 (s, 1H), 7.20 (s, 3H), 7.35 (br s, 1H), 7.73 (s, 1H), 8.25 (s, 1H); Mass Spectrum: M+H$^+$ 550.

[106] The product gave the following data: NMR Spectrum: (DMSOd$_6$, 100° C.) 1.4 (m, 11H), 1.79 (d, 3H), 1.95 (t, 2H), 2.2 (s, 3H), 2.37 (s, 3H), 3.89 (s, 3H), 4.01 (d, 2H), 4.07 (d, 2H), 7.11 (s, 1H), 7.31 (m, 2H), 7.44 (d, 1H), 7.7 (s, 1H), 8.49 (s, 1H); Mass Spectrum: M+H$^+$ 583 and 585.

[107] Glycine methylamide was used as the appropriate amine. The product gave the following data: NMR Spectrum: (DMSOd$_6$, 100° C.) 1.42 (m, 2H), 1.79 (d, 2H), 1.96 (t, 2H), 2.2 (s, 3H), 2.37 (s, 3H), 2.7 (d, 3H), 2.8 (d, 2H), 3.81 (s, 3H), 4.0 (d, 2H), 4.05 (d, 2H), 7.1 (s, 1H), 7.3 (m, 2H), 7.52 (s, 1H), 7.61 (s, 1H), 8.59 (s, 1H); Mass Spectrum: M+H$^+$ 540 and 542.

[108] Glycine isopropylamide was used as the appropriate amine. The product gave the following data: NMR Spectrum: (DMSOd$_6$, 100° C.) 1.02–1.10 (m, 6H), 1.32–1.44 (m, 2H), 1.76 (br d, 3H), (br t, 2H), 2.19 (s, 3H), 2.34 (s, 3H), 2.78 (d, 2H), 3.79 (s, 3H), 3.82–3.96 (m, 1H), 3.98–4.04 (m, 4H), 7.05 (s, 1H), 7.22–7.34 (m, 3H), 7.41 (d, 1H), 7.6 (s, 1H), 8.4 (s, 1H); Mass Spectrum: M+H$^+$ 568 and 570.

[109] (S)-Alanine tert-butyl ester hydrochloride was treated with triethylamine to give the required amine. The product gave the following data: NMR Spectrum: (DMSOd$_6$, 100° C.) 1.19 (d, 3H), 1.34 (s, 6H), 1.4 (s, 9H), 3.9 (s, 3H), 4.44 (m, 1H), 5.3 (s, 2H), 6.99 (s, 1H), 7.18 (s, 4H), 7.3 (m, 1H), 7.53 (d, 1H), 7.8 (m, 2H), 8.41 (s, 1H), 8.56 (d, 1H), 11.5 (br s, 1H); Mass Spectrum: M+H$^+$ 557.

[110] The product gave the following data: NMR Spectrum: (CDCl$_3$) 2.13 (m, 2.13 (m, 2H), 2.2 (s, 6H), 2.5 (t, 4H), 2.58 (t, 2H), 3.13 (t, 2H), 3.72 (t, 4H), 4.0 (m, 5H), 4.28 (t, 2H), 5.6 (m, 1H), 7.05–7.21 (m, 6H), 7.58 (m, 1H), 7.98 (s, 1H), 8.22 (d, 1H), 8.57 (s, 1H), 12.43 (s, 1H); Mass Spectrum: M+H$^+$ 570.

[111] The product gave the following data: NMR Spectrum: (DMSOd$_6$, 100° C.) 2.29 (s, 6H), 3.3 (s, 3H), 3.5 (t, 2H), 3.64 (t, 2H), 3.76 (s, 3H), 3.84 (t, 2H), 4.26 (t, 2H), 4.8 (d, 2H), 7.1 (s, 1H), 7.2 (s, 3H), 7.25 (m, 1H), 7.45 (d, 1H), 7.54 (s, 1H), 7.77 (t, 1H), 8.48 (s, 1H), 8.51 d, 1H), 11.08 (br s, 1H); Mass Spectrum: M+H$^+$ 531.

The 1-(2,6-dimethylphenyl)-3-[6-methoxy-7-[2-(2-methoxy)ethoxy]quinazolin-4-yl]thiourea used as a starting material was prepared as follows:—

4-(4-Bromo-2-fluorophenoxy)-7-hydroxy-6-methoxyquinazoline was reacted with 2-(2-methoxyethoxy)ethyl tosylate (prepared from 2-2-methoxyethoxy)ethanol and tosyl chloride) using an analogous procedure to that described in the third last paragraph of Note [41] above to give 4-(2-bromo-4-fluorophenoxy)-6-methoxy-7-[2-(2-methoxyethoxy)ethoxy]quinazoline: NMR Spectrum: (CDCl$_3$) 3.4 (s, 3H) 3.6 (m, 2H), 3.76 (m, 2H), 4.03 (m, 5H), 4.39 (t, 2H), 7.21 (m, 1H), 7.34 (s, 1H), 7.41 (t, 2H), 7.51 (s, 1H), 8.6 (s, 1H); Mass Spectrum: M+H$^+$ 467 & 469.

The material so obtained was reacted with ammonia using an analogous procedure to that described in the second last paragraph of the portion of Example 1that is concerned with the preparation of starting materials. There was thus obtained 4-amino-6-methoxy-7-[2-(2-methoxyethoxy)ethoxy]quinazoline; NMR Spectrum: (DMSO$_6$) 3.23 (s, 3H), 3.46 (m, 2H), 3.6 (m, 2H), 3.79 (t, 2H), 3.88 (s, 3H), 4.2 (t, 2H), 7.08 (s, 1H), 7.39 (s, 2H), 7.57 (s, 1H), 8.23 (s, 1H); Mass Spectrometry: M+H$^+$ 249.

The material so obtained reacted with 2,6-dimethylphenyl isothiocyanate using an analogous procedure to that described in the last paragraph of the portion of Example 1 which is concerned with the preparation of starting materials. There was thus obtained the required starting material; NMR Spectrum: (CDCl$_3$) 2.35 (s, 6H), 3.4 (s, 3H), 3.87 (m, 2H), 4.03 (t, 2H), 4.05 (s, 3H), 4.37 (t, 2H), 7.09 (s, 1H), 7.14–7.21 (m, 3H), 7.33 (s, 1H), 8.68 (s, 1H), 8.84 (s, 1H), 13.32 (s, 1H); Mass Spectrum: M+H$^+$ 457.

[112] The product gave the following data: NMR Spectrum: (DMSOd$_6$, 100° C.) 2.26 (s,6H), 3.3 (s, 3H), 3.5 (t, 2H); 3.64 (t, 2H), 3.8 (s, 3H), 3.84 (t, 2H), 4.25 (t, 2H), 4.72 (d, 2H), 7.12 (s, 1H), 7.2 (s, 3H), 7.31 (m, 1H), 7.35 (br s, 1H), 7.6 (s, 1H), 7.8 (m, 1H), 8.44 (m, 2H), 8.68 (s, 1H), 11.4 (br s, 1H); Mass Spectrum: M+H$^+$ 531.

[113] The product gave the following data: NMR Spectrum: (DMSOd$_6$, 100° C.) 2.3 (s, 6H), 3.31 (s, 3H), 3.51 (t, 2H), 3.65 (t, 2H), 3.74 (s, 3H), 3.85 (t, 2H), 4.29 (t, 2H), 4.71 (d, 2H), 7.12 (s, 1H), 7.21 (s, 3H), 7.39 (d, 2H), 7.5 (s, 1H), 8.48 (s, 1H), 8.51 (d, 2H), 11.4 (br s, 1H); Mass Spectrum: M+H$^+$ 531.

[114] The product gave the following data: NMR Spectrum: (DMSOd$_6$, 100° C.) 2.23 (s, 6H), 3.16 (t, 2H), 3.31 (s, 3H), 3.51 (m, 2H), 3.68 (m, 2H), 3.8 (s, 3H), 3.84 (m, 2H), 3.9 (m, 2H), 4.29 (m, 2H), 7.12 (s, 1H), 7.2 (m, 4H), 7.29 (m, 1H), 7.69 (s, 2H), 8.42 (d, 2H), 11.0 (br s, 1H); Mass Spectrum: M+H$^+$ 545.

[115] The product gave the following date: NMR Spectrum: (DMSOd$_6$, 100° C.) 1.41 (m, 2H), 1.79 (d, 3H), 1.97 (t, 2H), 2.2 (s, 3H), 2.3 (s, 3H), 2.8 (d, 2H), 3.74 (s, 3H), 4.0 (d, 2H), 4.71 (d, 2H), 7.02 (t, 1H), 7.10 (s, 1H), 7.21–7.5 (m, 7H), 8.0 (br s, 1H), 8.45 (s, 1H); Mass Spectrum: M+H$^+$ 577 and 579.

[116] The product gave the following data: NMR Spectrum: (DMSOd$_6$, 100° C.) 2.23 (s, 6H), 2.55 (m, 4H), 2.8 (t, 2H), 3.16 (t, 2H), 3.61 (t, 4H), 3.8 (s, 3H), 3.9 (m, 2H), 4.29 (t, 2H), 7.11 (s, 1H), 7.2 (m, 4H), 7.29 (d, 1H), 7.7 (m, 2H), 8.41 (s, 2H), 11.0 (br s, 1H); Mass Spectrum: M+H$^+$ 556.

[117] The product gave the following data: NMR Spectrum: (DMSOd$_6$, 100° C.) (s, 6H), 2.51 (t, 4H), 2.79 (t, 2H), 3.6 (t, 4H), 3.73 (s, 3H), 4.22 (t, 2H), 4.79 (d, 2H), 7.11 (s, 1H), 7.2 (s, 3H), 7.24 (m, 1H), 7.45 (d, 1H), 7.54 (s, 1H), 7.77 (t, 1H), 8.46 (s, 1H), 8.5 (d, 1H), 11.1 (br s, 1H); Mass Spectrum: M+H$^+$ 542.

[118] The product gave the following data: NMR Spectrum: (DMSOd$_6$, 100° C.) 2.22 (d, 9H), 2.54 (t, 4H), 2.8 (t, 2H), 3.6 (m, 4H), 3.8 (s, 3H), 4.27 (t, 2H), 4.65 (d, 2H), 5.99 (m, 1H), 6.2 (d, 1H), 7.12 (s, 1H), 7.16 (s, 3H), 7.62 (s, 1H), 8.45, (s, 1H), 10.79 (br s, 1H); Mass Spectrum: M+H$^+$ 545.

[119] The product gave the following data: NMR Spectrum: (DMSOd$_6$, 100° C.) 2.23 (s, 6H). 2.53 (t, 4H), 2.81 (t, 2H), 3.23 (t, 2H), 3.61 (t, 4H), 3.77 (m, 5H), 4.28 (t, 2H), 6.95 (m, 2H), 7.11 (s, 1H), 7.18 (s, 3H), 7.3 (d, 1H), 7.64 (s, 1H), 8.42 (s, 1H), 11.0 (br s, 1H); Mass Spectrum: M+H$^+$ 561.

[120] The product gave the following data: NMR Spectrum: (DMSOd$_6$, 100° C.) 1.4 (m, 2H), 1.78 (m, 3H), 1.99 (t, 2H), 2.2 (s, 3H), 2.27 (s, 3H), 2.8 (d, 2H), 3.78 (s, 3H), 4.0 (d, 2H), 4.86 (d, 2H), 6.94 (t, 1H), 7.08 (m, 2H), 7.25 (m, 3H), 7.39 (d, 1H), 7.8 (br s, 1H), 8.41 (s, 1H), 11.3 (br s, 1H); Mass Spectrum: M+H$^+$ 565 and 567.

[121] The product gave the following data: NMR Spectrum: (DMSOd$_6$, 100° C.) 1.4 (m, 2H), 1.8 (d, 3H), 1.97 (t, 2H), 2.2 (s, 3H), 2.79 (d, 2H), 3.26 (t, 2H), 3.73 (s, 3H), 3.8 (q, 2H), 4.0 (d, 2H), 6.97 (d, 2H), 7.09 (s, 1H), 7.3 (s, 3H), 7.42 (d, 1H), 7.54 (s, 1H), 8.42 (s, 1H); Mass Spectrum: M+H$^+$ 579 and 581.

[122] The product gave the following data: NMR Spectrum: (DMSOd$_6$, 100° C.) 1.69 (m, 1H), 1.9 (m, 2H), 2.0 (m, 1H), 2.28 (s, 6H), 2.56 (t, 4H), 2.81 (t, 2H), 3.51–3.85 (m, 11H), 4.17 (m, 1H), 4.28 (t, 2H), 7.11 (s, 1H), 7.19 (s, 3H), 7.51 (s, 1H), 8.45 (s, 1H), 10.4 (br s, 1H); Mass Spectrum: M+H$^+$ 535.

[123] The product gave the following data: NMR Spectrum: (DMSOd$_6$, 100° C.) 1.6 (m, 1H), 1.79 (m, 2H), 1.9 (m, 1H), 2.18 (s, 6H), 2.42 (t, 4H), 2.69 (t, 2H), 3.41–3.6 (m, 7H), 3.65 (s, 3H), 3.7 (q, 1H), 4.07 (m, 1H), 4.17 (t, 2H), 7.01 (s, 1H), 7.08 (s, 3H), 7.41 (s, 1H), 8.34 (s, 1H), 10.3 (br s, 1H); Mass Spectrum: M+H$^+$ 535.

[124] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.56–1.74 (m, 4H), 1.9 (m, 2H), 2.09 (m, 1H), 2.16 (s, 3H), 2.29 (m, 1H), 2.32 (s, 3H), 2.58 (t, 4H), 2.8 (t, 3H), 3.6 (m, 6H), 3.78 (s, 3H), 4.27 (t, 2H), 7.11 (s, 1H), 7.28 (m, 1H), 7.35 (d, 1H), 7.43 (d, 1H), 7.59 (s, 1H), 8.12 (br s, 1H), 8.44, (s, 1H); Mass Spectrum: M+H$^+$ 582 and 584.

[125] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.54–1.75 (m, 4H), 1.91 (m, 2H), 2.1 (q, 1H), 2.2 (s, 3H), 2.3 (m, 1H), 2.58 (t, 4H), 2.81 (t, 2H), 2.86 (m, 3.61 ) (m, 6H), 3.84 (s, 3H), 4.28 (t, 2H), 7.14 (s, 1H), 7.29 (t, 1H), 7.41 (t, 1H), 7.59 (d, 2H), 7.67 (s, 1H), 8.34 (br s, 1H), 8.47, (s, 1H); Mass Spectrum: M+H$^+$ 568 and 570.

[126] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.53–1.73 (m, 4H), 1.83–1.97 (m, 2H), 2.06 (q, 1H), 2.17 (s, 3H), 2.28 (m, 1H), 2.32 (s, 3H), 2.55 (t, 4H), 2.8 (m, 3H), 3.6 (m, 6H), 3.82 (s, 3H), 4.29 (t, 2H), 7.14 (s, 1H), 7.2–7.38 (m, 4H), 7.71 (s, 1H), 7.8 (br s, 1H), 8.56 (s, 1H), 11.16 (br s, 1H); Mass Spectrum: M+H$^+$ 548.

[127] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.53–1.75 (m, 4H), 1.91 (m, 2H), 2.1 (m, 1H), 2.2 (s, 3H), 2.3 (m, 1H), 2.56 (t, 4H), 2.81 (t, 2H), 2.88 (m, 1H), 3.6 (m, 6H), 3.77 (s, 3H), 4.27 (t, 2H), 7.11 (s, 1H), 7.35 (t, 1H), 7.49 (s, 1H), 7.6 (d, 2H), 8.45 (s, 1H); Mass Spectrum: M+H$^+$ 602 and 604.

[128] The product gave the following data: NMR Spectrum: (DMSOd$_6$, 100° C.) 1.52–1.71 (m, 4H), 1.8–1.92 (m, 2H), 2.01 (q, 1H), 2.1 (s, 3H), 2.27 (s, 6H), 2.55 (t, 4H), 2.76 (m, 1H), 2.81 (t, 2H), 3.56 (m, 1H), 3.61 (t, 4H), 3.67 (m, 1H), 3.82 (s, 3H), 4.27 (t, 2H), 7.12 (s, 1H), 7.19 (s, 3H), 7.5(br s, 1H), 7.69 (s, 1H), 7.69 (s, 1H), 8.42 (s, 1H), 11.1 (br s, 1H); Mass Spectrum: M+H$^+$ 562.

[129] The product gave the following data: NMR Spectrum: (DMSOd$_6$, 100° C.) 2.21 (s, 6H), 2.53 (t, 4H), 2.8 (t, 2H), 3.58 (t, 4H), 3.8 (s, 3H), 4.23 (t, 2H), 4.82 (d, 2H), 6.92 (t, 1H), 7.04 (d, 1H), 7.12 (s, 1H), 7.15 (s, 3H), 7.2 (br s, 1H), 7.3 (m, 1H), 7.78 (s, 1H), 8.42 (s, 1H), 11.4 (br s, 1H); Mass Spectrum: M+H$^+$ 547.

[130] The product gave the following data: NMR Spectrum: (DMSOd$_6$, 100° C.) 1.61–1.7 (m, 4H), 1.78–1.91 (m, 2H), 2.02 (q, 1H), 2.27 (s, 6H), 2.75 (t, 1H), 3.3 (s, 3H), 3.53 (m, 3H), 3.67 (m, 3H), 3.83 (m, 6H), 4.26 (t, 2H), 7.11 (s, 1H), 7.2 (s, 3H), 7.49 (br s, 1H), 7.72 (s, 1H), 8.44 (s, 1H), 11.1 (br s, 1H); Mass Spectrum: M+H$^+$ 551.

[131] The product gave the following data: NMR Spectrum: (DMSOd$_6$, 100° C.) 1.4 (m, 2H), 1.5–1.7 (m, 4H), 1.75–1.95 (m, 7H), 2.15 (s, 3H), 2.2 (s, 3H), 2.3 (s, 3H), 2.35 (s, 3H), 2.8 (t, 2H), 3.2 (t, 2H), 3.55 (m, 1H), 3.65 (m, 2H), 3.8 (s, 3H), 4.0 (d, 2H), 7.05 (d, 1H), 7.1 (m, 2H), 7.25 (d, 1H), 7.5 (s, 1H), 7.7 (s, 1H), 8.45 (s, 1H), 11.25 (s, 1H); Mass Spectrum: M+H$^+$ 560.

The 1-(2,5-dimethylphenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy)quinazoline was reacted with 2,5-dimethylphenyl isothiocyanate using an analogous procedure to that described in the last paragraph of the portion of Example 1 which is concerned with the preparation of starting materials. There was thus obtained the required starting material: Mass Spectrum: M+H$^+$ 466.

[132] The product gave the following data: NMR Spectrum: (DMSOd$_6$, 100° C.) 1.34 (s, 9H), 1.2–1.45 (m, 3H), 1.48–1.6 (m, 5H), 1.72–2.06 (m, 7H), 2.17 (s, 3H), 2.23 (s, 6H), 2.74–2.8 (m, 3H), 3.38–3.56 (m, 2H), 3.77 (s, 3H), 3.83 (s, 1H), 3.98 (d, 2H), 4.18–4.26 (br s, 1H), 7.05 (s, 1H), 7.16 (s, 3H), 7.6 (s, 1H), 8.41 (s, 1H); Mass Spectrum: M+H$^+$ 660.

[133] The product gave the following data: NMR Spectrum: (DMSOd$_6$, 100° C.) 1.66 (s, 4H), 2.12 (m, 2H), 2.32 (s, 6H), 2.4–2.6 (m, 10H), 2.7 (s, 2H), 3.68 (q, 2H), 3.74 (t, 4H), 4.0 (s, 3H), 4.25 (t, 2H), 4.97 (m, 1H), 7.18 (s, 4H), 7.9 (s, 1H), 8.57 (s, 1H), 12.5 (s, 1H); Mass Spectrum: M+H$^+$ 562.

[134] The product gave the following data: NMR Spectrum: (CDCl$_3$) 1.66 (s, 4H), 1.8 (t, 2H), 2.12 (m, 2H), 2.32 (s, 10H) 2.45–2.63 (m, 8H), 3.74 (t, 6H), 4.0 (s, 3H), 4.25 (t, 2H), 5.77 (m, 1H), 7.12 (s, 4H), 7.9 (s, 1H), 8.55 (s, 1H), 12.5 (s, 1H); Mass Spectrum: M+H$^+$ 576.

[135] The product gave the following data: NMR Spectrum: (CDCl$_3$) 2.11 (m, 2H), 2.35 (s, 10H), 2.5 (m, 6H), 2.58 (t, 2H), 2.68 (s, 4H), 3.62 (q, 2H), 3.72 (t, 4H), 4.0 (s, 3H), 4.25 (t, 2H), 5.12 (m, 1H), 7.18 (s, 4H), 7.9 (s, 1H), 8.57 (s, 1H), 12.5 (s, 1H); Mass Spectrum: M+H$^+$ 577.

[136] The product gave the following data: NMR Spectrum: (CDCl$_3$) 1.82 (m, 2H), 1.82 (m, 2H), 2.12 (m, 4H), 2.15–2.31 (m, 5H), 2.35 (s, 6H), 2.4 (m, 6H), 2.5 (t, 4H), 2.58 (t, 2H), 3.7 (q, 2H), 3.72 (t, 4H), 4.0 (s, 3H), 4.25 (t, 2H), 5.12 (m, 1H), 7.18 (s, 4H), 7.9 (s, 1H), 8.57 (s, 1H), 12.5 (s, 1H); Mass Spectrum: M+H$^+$ 605.

[137] The product gave the following data: NMR Spectrum: (DMSOd$_6$, 100° C.) 1.3–1.5 (m, 2H), 1.7–1.9 (m, 3H), 1.96–2.1 (t, 2H), 2.21 (s, 6H), 2.25 (s, 6H), 2.45–2.5 (m, 4H), 2.86 (d, 2H), 3.23 (s, 3H), 3.42 (t, 2H), 3.56 (q, 2H), 3.72 (s, 3H), 3.94 (d, 2H), 7.04 (s, 3H), 7.15 (s, 3H), 7.53 (s, 1H), 8.4 (s, 1H); Mass Spectrum: M+H$^+$ 564.

The 1-(2,6-dimethylphenyl)-3-[6-methoxy-7-[N-(2-methoxyethyl)piperidin-4-ylmethoxy]quinazolin-4-yl]thiourea used as a starting material was prepared as follows:—

N-tert-Butoxycarbonyl-4-(4-benzenesulphonyloxymethyl)piperidine was obtained by the reaction of N-tert-butoxycarbonyl-4-hydroxymethylpiperdine with benzenesulphonyl chloride using an analogous procedure to that described in the portion of Example 1 that is concerned with the preparation of starting materials which concerns the corresponding reaction with 4-toluenesulphonyl chloride.

A mixture of 4-(2-bromo-4-fluorophenoxy)-7hydroxy-6-methoxyquinazoline (21.9 g), N-tert-butoxycarbonyl-4-(4-benzenesulphonyloxymethyl)piperidine (31 g), anhydrous potassium carbonate (33.1 g) and NMP (200 ml) was stirred and heated to 82° C. for 16 hours. The reaction mixture was allowed to cool to 50° C. and poured into water (1.2 L). The precipitate was isolated, washed with water, triturated under diethyl ether and isolated. There was thus obtained 4-(2-bromo-4-fluorophenoxy)-7-(N-tert-butoxycarbonylpiperidin-4-ylmethoxy)-6-methoxyquinazoline (32.95 g); NMR Spectrum: (DMSOd$_6$) 1.23 (m, 2H), 1.42 (s, 9H), 1.77–2.2 (m, 2H), 2.8 (m, 2H), 3.97 (s, 3H), 3.99 (m, 2H), 4.1 (d, 2H), 7.36–7.42 (m, 2H), 7.52–7.56 (m, 1H), 7.58 (s, 1H), 7.87 (m, 1H), 8.56 (s, 1H); Mass Spectrum: M+H$^+$ 562 and 564.

Using an analogous procedure to that described in the second last paragraph of the portion of Example 1 that is concerned with the preparation of starting materials, 4-(2-bromo-4-fluorophenoxy)-7-(N-tert-butoxycarbonylpiperidin-4-ylmethoxy)-6-methoxyquinazoline was reacted with ammonia to give 4-amino-7-(N-tert-butoxycarbonylpiperidin-4-ylmethoxy)-6-methoxyquinazoline; NMR Spectrum: (DMSOd$_6$) 1.21 (m, 2H), 1.4 (s, 9H), 1.76 (d, 2H), 2.0 (br s, 1H), 2.77 (t, 2H), 3.88 (s, 3H), 3.97 (d, 2H), 3.99 (br s, 2H), 7.05 (s, 1H), 7.36 (br s, 2H), 7.55 (s, 1H), 8.24 (s, 1H); Mass Spectrum: M+H$^+$ 389.

The material so obtained was reacted with 2,6-dimethylphenyl isothiocyanate using an analogous procedure to that described in the last paragraph of the portion of Example 1 which is concerned with the preparation of starting materials. There was thus obtained 1-(2,6-dimethylphenyl)-3-[7-[N-tert-butoxycarbonylpiperidin-4-ylmethoxy]-6-methoxyquinazolin-4-yl]thiourea; NMR Spectrum: (CDCl$_3$) 1.31 (m, 2H), 1.43 (s, 9H), 1.85 (br d, 2H), 2.09 (br s, 1H), 2.29 (s, 6H), 2.74 (t, 2H), 3.96 (m, 5H), 4.14 (m, 2H), 7.0 (s, 1H), 7.09–7.19 (s, 3H), 7.23 (s, 1H), 8.63 (s, 1H), 8.8 (s, 1H), 13.3 (s, 1H); Mass Spectrum: M+H$^+$ 552.

A mixture of the thiourea so obtained (1.5 g), trifluoroacetic acid (15 ml) and methylene chloride (15 ml) was stirred at ambient temperature for 1 hour. The mixture was evaporated and the residue was azeotroped with toluene. The residue was stirred with a saturated aqueous sodium bicarbonate solution and the resultant solid was isolated and washed with water. There was thus obtained 1-(2,6-dimethylphenyl)-3-(6-methoxy-7-piperidin-4-ylmethoxyquinazolin-4-yl)thiourea (1.25 g); NMR Spectrum: (DMSOd$_6$) 1.34–1.48 (m, 2H), 1.87 (d, 2H), 2.2 (s, 6H), 2.81 (t, 2H), 3.21 (d, 3H), 3.99 (s, 3H), 4.06 (d, 2H), 7.14 (s, 3H), 7.33 (s, 1H), 8.14 (s, 1H), 8.65 (s, 1H); Mass Spectrum: M+H$^+$ 452.

Methoxyacetaldehyde (0.314 g) was added to a stirred mixture of 1-(2,6-dimethylphenyl)-3-(6-methoxy-7-piperidin-4-ylmethoxyquinazolin-4-yl)thiourea (1.47 g), 3 Å molecular sieves (1.0 g) and methanol (75 ml) and the mixture was stirred at ambient temperature for 30 minutes. Sodium cyanoborohydride (0.205 g) and acetic acid (0.105 g) were added in turn and the mixture was stirred at ambient temperature for 16 hours. The mixture was acidified to pH 2 by the addition of concentrated hydrochloric acid. The mixture was evaporated, the residue was dissolved in water (10 ml) and the solution was basified to pH10 by the addition of 10N aqueous potassium hydroxide solution. The mixture was extracted with a 10:1 mixture of methylene chloride and methanol and the combined organic extracts were evaporated. The residue was purified by column chromatography on silica using increasingly polar mixtures of methylene chloride and a 2M solution of ammonia gas in methanol as eluent. There was thus obtained 1-(2,6-dimethylphenyl)-3-{6-methoxy-7-[N-(2-methoxyethyl)piperidin-4-ylmethoxy]quinazolin-4yl}thiourea (0.493 g); NMR Spectrum: (CDCl$_3$) 1.45–2.1 (m, 7H), 2.35 (s, 6H), 2.59 (t, 2H), 3.01 (d, 2H), 3.37 (s, 3H), 3.54 (m, 2H), 4.02 (s, 5H), 7.06 (s, 1H), 7.12–7.2 (m, 3H), 7.31 (s, 1H), 8.65 (s, 1H), 8.83 (s, 1H), 13.34 (s, 1H); Mass Spectrum: M+H$^+$ 510.

[138] The product gave the following data: NMR Spectrum: (DMSOd$_6$, 100° C.) 1.3–1.5 (m, 2H), 1.7–1.9 (m, 3H), 2.03 (t, 2H), 2.28 (s, 6H), 2.45–2.53 (m, 2H), 2.85–2.91 (m, 3H), 3.14 (s, 3H), 3.43 (t, 2H), 3.87 (s, 3H), 3.95–4.03 (m, 4H), 7.08 (s, 1H), 7.16 (s, 3H), 7.73 (s, 1H) 8.45 (s, 1H); Mass Spectrum: M+H$^+$ 607.

[139] The product gave the following data: NMR Spectrum: (DMSOd$_6$, 100° C.) 1.3–1.5 (m, 2H), 1.6–2.1 (m, 11H), 2.24 (s, 6H), 2.85 (d, 2H), 3.22 (s, 3H), 3.42 (t, 2H), 3.45–3.86 (m, 7H), 3.95 (d, 2H), 4.14 (m, 1H), 7.03 (s, 1H), 7.14 (s, 3H), 7.48 (s, 1H), 8.41 (s, 1H); Mass Spectrum: M+H$^+$ 577.

[140] The product gave the following data; NMR Spectrum: (CDCl$_3$) 2.13 (s, 6H), 2.26 (s, 6H), 2.42 (m, 2H), 2.69 (m, 1H), 3.06 (m, 1H), 3.45–3.7 (m, 8H), 3.83–4.02 (m, 4H), 4.15 (m, 1H), 4.4 (m, 1H), 4.79 (m, 1H), 7.1 (s, 4H), 7.15–7.34 (m, 5H), 7.83 (s, 1H), 8.5 (s, 1H), 12.5 (s, 1H); Mass Spectrum: M+H$^+$ 598.

The 1-[7-(N-benzylmorpholin-3-ylmethoxy)-6-methoxyquinazolin-4-yl]-3-(2,6-dimethylphenyl)thiourea used as a starting material was prepared as follows:—

Mesyl chloride (1.87 ml) was added a mixture of N-benzylmorpholin-3-ylmethanol (*J. Chem. Soc. Perkin I*, 1985, 2577–2580; 5 g), triethylamine (3.3 ml) and THF (20 ml) which had been cooled in an ice/water bath. The mixture was stirred for 2 hours whilst being allowed to warm to ambient temperature. The mixture was filtered and the filtrate was evaporated. The residual oil was dissolved in DMF (100 ml) and 4-(2-bromo-4-fluorophenoxy)-7-hydroxy-6-methoxyquinazoline (4.56 g) and anhydrous potassium carbonate (5.18 g) were added. The resultant mixture was heated to 70° C. for 16 hours. The mixture was evaporated and the residual oil was triturated under diethyl ether. There was thus obtained 7-(N-benzylmorpholin-3-ylmethoxy)-4-(2-bromo-4-fluorophenoxy)-6-methoxyquinazoline as a solid (4.11 g); NMR Spectrum: (DMSOd$_6$) 2.7 (m, 2H), 2.97 (m, 1H), 3.5–3.7 (m, 4H), 3.89 (m, 1H), 4.0 (s, 3H), 4.09 (d, 1H), 4.31 (m, 1H), 4.52 (m, 1H), 7.18–7.45 (m, 6H), 7.5–7.65 (m, 3H), 7.78 (m, 1H), 8.56 (s, 1H); Mass Spectrum: M+H$^+$ 554 and 556.

The material so obtained was reacted with ammonia using an analogous procedure to that described in the second last paragraph of the portion of Example 1 that is concerned with the preparation of starting materials. There was thus obtained 4-amino-7-(N-benzylmorpholin-3-ylmethoxy)-6-methoxyquinazoline.

The material so obtained was reacted with 2,6-dimethylphenyl isothiocyanate using an analogous procedure to that described in the last paragraph of the portion of Example 1 which is concerned with the preparation of starting materials. There was thus obtained 1-[7-(N-benzylmorpholin-3-ylmethoxy)-6-methoxyquinaolin-4-yl]-3-(2,6-dimethylphenyl)thiourea; Mass Spectrum: M+H⁺ 544.

[141] The product gave the following data: NMR Spectrum: (DMSOd₆, 100° C.) 2.02–2.23 (m, 8H), 2.26 (s, 6H), 2.42 (m, 2H), 2.62 (d, 1H), 2.9 (d, 1H), 3.4–3.62 (m, 4H), 3.68 (t, 1H), 3.89 (d, 3H), 4.04 (d, 2H), 4.17 (m, 1H), 4.79 (m, 1H), 7.08 (s, 3H), 7.15 (s, 1H), 7.2–7.33 (m, 5H), 7.83 (s, 1H), 8.5 (s, 1H), 12.42 (s, 1H); Mass Spectrum: M+H⁺ 598.

The 1-[7-(N-benzylmorpholin-2-ylmethoxy)-6-methoxyquinazolin-4-yl]-3-(2,6-dimethylphenyl)thiourea used as a starting material was prepared as follows:—

Using an analogous procedure to that described in the first paragraph of the portion of Note [140] immediately above which is concerned with the preparation of starting materials, the mesylate of N-benzylmorpholin-2-ylmethanol (*Synth. Commun.* 1980, 10, 59–73) was reacted with 4-(2-bromo-4-fluorophenoxy)-7-hydroxy-6-methoxyquinazoline (4.56 g) to give 7-(N-benzylmorpholin-2-ylmethoxy)-4-(2-bromo-4-fluorophenoxy)-6-methoxyquinazoline; Mass Spectrum: M+H⁺ 554 and 556.

The material so obtained was reacted with ammonia using an analogous procedure to that described in the second last paragraph of the portion of Example 1 that is concerned with the preparation of starting materials. There was thus obtained 4-amino-7-(N-benzylmorpholin-2-ylmethoxy)-6-methoxyquinazoline.

The material so obtained was reacted with 2,6-dimethylphenyl isothiocyanate using an analogous procedure to that described in the last paragraph of the portion of Example 1 which is concerned with the preparation of starting materials. There was thus obtained 1-[7-(N-benzylmorpholin-2-ylmethoxy)-6-methoxyquinazolin-4-yl]-3-(2,6-dimethylphenyl)thiourea; Mass Spectrum: M+H⁺ 544.

[142] Glycine 2-hydroxyethylamide (*Helv. Chim. Acta,* 1955, 38, 1345) was used as the appropriate amine. The product gave the following date: NMR Spectrum: (DMSOd₆, 100° C.) 1.41 (q, 2H), 1.79 (d, 3H), 2.02 (t, 2H), 2.2 (s, 3H), 2.27 (s, 6H), 2.82 (d, 2H), 3.14–3.22 (m, 2H), 3.4 (s, 2H), 3.84 (s, 3H), 3.97 (d, 2H), 4.09 (s, 2H), 4.33 (br s, 1H), 7.1 (s, 1H), 7.18 (s, 3H), 7.58 (s, 1H), 7.68 (s, 1H), 8.46 (s, 1H); Mass Spectrum: M+H⁺ 550.

[143] Glycine 2-hydroxyethylamide was used as the appropriate amine. The product gave the following data: NMR Spectrum: (DMSOd₆, 100° C.) 1.32–1.46 (m, 2H), 1.77 (d, 3H), 2.02 (t, 2H), 2.22 (s, 3H), 2.34 (s, 3H), 2.83 (d, 2H), 3.16–3.24 (m, 2H), 3.42 (s, 2H), 3.78 (s, 3H), 3.97 (d, 2H), 4.06 (s, 2H), 4.33 (s, 1H), 7.04 (s, 1H), 7.22–7.42 (m, 3H), 7.55 (s, 2H), 8.45 (s, 1H); Mass Spectrum: M+H⁺ 570 and 572.

[144] The product gave the following data: NMR Spectrum: (DMSOd₆, 100° C.) 1.42 (m, 2H), 1.82 (m, 3H), 1.93 (m, 2H), 2.18 (s, 3H), 2.79 (m, 2H), 3.38 (s, 3H), 3.86 (s, 3H), 4.01 (d, 2H), 4.13 (m, 2H), 5.18 (m, 1H), 5.31 (m, 1H), 6.06 (m, 1H), 6.98 (m, 1H), 7.09 (s, 1H), 7.12 (m, 1H), 7.19 (m, 1H), 7.59 (m, 1H), 7.74 (s, 1H), 8.0 (br s, 1H), 8.47 (s, 1H); Mass Spectrum: M+H⁺ 491.

The 1-[6-methoxy-7-(N-methylpiperidin-4-ylmethoxy)quinazoline-4-yl]-3-(2-methoxyphenyl)thiourea used as a starting material was prepared by the reaction of 4-amino-6-methoxy-7-(N-methylpiperidin-4-ylmethoxy)quinazoline with 2-methoxyphenyl isothiocyanate using an analogous procedure to that described in the last paragraph of the portion of Example 1 which is concerned with the preparation of starting materials. There was thus obtained 1-[6-methoxy-7-(N-methylpiperidin-4-ylmethoxy)quinazolin-4-yl]-3-(2-methoxyphenyl)thiourea; NMR Spectrum: (DMSOd₆) 1.38 (m,2H), 1.81 (m, 3H), 1.86 (m, 2H), 2.2 (s, 3H), 2.79 (m, 2H), 3.96 (s, 3H), 3.99 (s, 3H), 4.09 (d, 2H), 6.95 (m, 1H), 7.18 (m, 1H), 7.19 (s, 1H), 7.23 (m, 1H), 7.32 (s, 1H), 8.13 (br s, 1H), 8.69 (br s, 1H), 8.78 (s, 1H), 10.96 (br s, 1H), 14.73 (br s, 1H); Mass Spectrum: M+H⁺ 468.

[145] The product gave the following data: NMR Spectrum: (DMSOd₆, 100° C.) 1.44 (m, 2H), 1.83 (m, 2H), 1.85 (m, 1H), 1.98 (m, 2H), 2.21 (s, 3H), 2.82 (m, 2H), 2.97 (m, 2H), 3.80 (t, 2H), 3.89 (s, 3H), 3.93 (s, 3H), 4.04 (d, 2H), 7.04 (m, 1H), 7.14 (s, 1H), 7.17 (m, 1H), 7.25 (br, 0.5H), 7.27 (m, 1H), 7.44 (m, 1H), 7.80 (s, 1H), 8.51 (s, 1H), 11.75 (br s, 1H); Mass Spectrum: M+H⁺ 504.

[146] The product gave the following data: Mass Spectrum: M+H⁺ 522 and 524.

[147] The product gave the following data: Mass Spectrum: (DMSOd₆, 100° C.) 1.41 (m, 2H), 1.79 (m, 3H),1.95 (t, 2H), 2.18 (s, 3H), 2.35 (s, 3H), 2.8 (m, 2H), 3.76 (s, 3H), 4.0 (d, 2H), 4.76 (d, 2H), 6.99 (br s, 1H), 7.11 (s, 1H), 7.15–7.58 (m, 6H), 8.05 (br s, 1H), 8.46 (s, 1H), 11.20 (br s, 1H); Mass Spectrum: M+H⁺ 577.

[148] THF was used as the reaction solvent in place of a 1:1 mixture of chloroform and methanol and the reaction mixture was heated to reflux for 2 hours. The product gave the following data: NMR Spectrum: (DMSOd₆, 100° C.) 1.42 (m, 4H), 1.56 (m, 1H), 1.77 (m, 5H), 1.95 (t, 2H), 2.16 (s, 6H), 2.2 (s, 4H), 2.38 (s, 3H), 2.75 (d, 2H), 3.12 (m, 1H), 3.52 (m, 1H), 3.74 (s, 3H), 3.94 (d, 2H), 6.97 (br s, 1H), 7.07 (m, 1H), 7.27 (t, 1H), 7.29 (d, 1H), 7.38 (d, 1H), 7.46 (br s, 1H), 8.44 (s, 1H), 10.1 (br s, 1H); Mass Spectrum: M+H⁺ 568 and 570.

[149] The product gave the following data: NMR Spectrum: (DMSOd₆, 100° C.) 2.17 (m, 7H), 2.45 (s, 6H), 2.73 (m, 2H), 3.54 (m, 6H), 3.96 (s, 3H), 4.25 (m, 2H), 7.03 (m, 3H), 7.25 (s, 1H), 8.00 (s, 1H), 8.6 (s, 1H), 10.55 (s, 1H), 13.33 (s, 1H); Mass Spectrum: M+H⁺ 547.

[150] THF was used as the reaction solvent in place of a 1:1 mixture of chloroform and methanol and the reaction mixture was heated to reflux for 2 hours. The product gave the following data: NMR Spectrum: (DMSOd₆, 100° C.) 1.5 (m, 2H), 1.71 (m, 2H), 2.12 (s, 6H), 2.3 (m, 8H), 2.55 (m, 4H), 2.78 (m, 2H), 3.55 (br s, 2H), 3.62 (m, 4H), 3.75 (s, 3H), 4.27 (m, 2H), 7.09 (s, 1H), 7.16 (s, 3H), 7.59 (s, 1H), 8.45 (s, 1H), 10.2–10.7 (br s, 1H); Mass Spectrum: M+H⁺ 550.

[151] THF was used as the reaction solvent in place of a 1:1 mixture of chloroform and methanol and the reaction mixture was heated to reflux for 2 hours. The product gave the following data: NMR Spectrum: (DMSOd₆, 100° C.) 2.34 (s, 3H), 2.86 (m, 4H), 3.51 (m, 2H), 3.65 (m, 6H), 3.81 (s, 3H), 4.00 (s, 1H), 4.28 (m, 2H), 4.37 (m, 2H), 4.81 (s, 1H), 7.11 (s, 1H), 7.15–7.45 (m, 4H), 7.65 (d, 1H), 8.48 (s, 1H), 8.82 (s, 1H), 10.7 (br s, 1H), 13.33 (s, 1H); Mass Spectrum: M+H⁺ 511.

[152] THF was used as the reaction solvent in place of a 1:1 mixture of chloroform and methanol and the reaction mixture was heated to reflux for 2 hours. The product gave the following data: NMR Spectrum: (DMSOd₆, 100° C.) 1.04 (t, 3H), 1.74 (m, 2H), 1.85 (q, 1H), 1.89 (m, 1H), 2.04 (s, 6H), 2.25 (s, 6H), 2.32 (q, 2H), 2.64 (m, 1H), 2.74 (m, 2H), 3.22 (t, 2H), 3.32 (t, 2H), 3.55 (q, 2H), 3.78 (s, 3H), 4.99 (m, 1H), 6.99 (s, 1H), 7.17 (s, 3H), 7.63 (br s, 1H), 8.42 (s, 1H),10.5–11.1 (br s, 1H); Mass Spectrum: M+H⁺ 570 and 572.

[153] THF was as the reaction solvent in place of a 1:1 mixture of chloroform and methanol and the reaction mixture was heated to reflux for 2 hours. The product gave the following data: NMR Spectrum: (DMSOd₆, 100° C.) 1.52

(m, 2H), 1.72 (m, 2H), 2.15 (s, 6H), 2.3 (m, 8H), 3.53 (t, 2H), 3.81 (s, 3H), 5.34 (s, 2H), 7.17 (s, 3H), 7.19 (s, 1H), 7.36 (m, 1H), 7.58 (d, 1H), 7.6 (s, 1H), 7.83 (t, 1H), 8.42 (s, 1H), 8.61 (d, 1H), 10.2–10.7 (br s, 1H); Mass Spectrum: M+H$^+$ 528.

[154] THF was used as the reaction solvent in place of a 1:1 mixture of chloroform and methanol and the reaction mixture was heated to reflux for 2 hours. The product gave the following data: NMR Spectrum: (DMSOd$_6$, 100° C.) 1.55 (m, 2H), 1.72 (m, 6H), 1.94 (m,2H), 2.17 (s, 6H), 2.32 (m, 5H), 2.5 (m, 4H), 2.63 (t, 2H), 3.53 (t, 2H), 3.72 (s, 3H), 4.19 (m, 2H), 7.07 (s, 1H), 7.24 (t, 1H), 7.28 (d, 1H), 7.41 (d, 1H), 7.42 (s, 1H), 8.42 (m, 2H), 9.9–10.4 (br s, 1H); Mass Spectrum: M+H$^+$ 568 and 570.

[155] The product gave the following data: NMR Spectrum: (DMSOd$_6$, 100° C.) 1.4 (m, 2H), 1.78 (m, 3H), 1.95 (m, 2H), 2.2 (s, 3H), 2.28 (s, 6H), 2.35 (s, 3H), 2.6 (m, 2H), 2.78 (m, 2H), 3.6 (m, 2H), 3.8 (s, 3H), 3.98 (d, 2H), 7.06 (s, 1H), 7.2 (m, 1H), 7.28 (m, 1H), 7.35 (m, 2H), 7.6 (s, 1H), 8.45 (s, 1H), 10.85 (s, 1H); Mass Spectrum: M+H$^+$ 506.

[156] The product gave the following data: NMR Spectrum: (DMSOd$_6$, 100° C.) 1.2 (t, 3H), 1.4 (m, 2H), 1.8 (m, 3H), 1.95 (m, 2H), 2.2 (s, 3H), 2.26 (s, 6H), 2.6 (m, 2.6 (m, 2H), 2.7 (q, 2H), 2.84 (m, 2H), 3.6 (m, 2H), 3.8 (s, 3H), 4.0 (d, 2H), 7.1 (s, 1H), 7.26 (m, 2H), 7.36 (m, 2H), 7.7 (s, 1H), 8.55 (s, 1H), 11.2 (s, 1H); Mass Spectrum M+H$^+$ 520.

The 1-(2-ethylphenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy)quinazoline was reacted with 2-ethylphenyl isothiocyanate using an analogous procedure to that described in the last paragraph of the portion of Example 1 which is concerned with the preparation of starting materials. There was thus obtained the required starting material: Mass Spectrum: M+H$^+$ 466.

[157] The product gave the following data: NMR Spectrum: (DMSOd$_6$, 100° C.) 1.43 (m, 2H), 1.5–1.65 (m, 4H), 1.72–2.0 (m, 7H), 2.15 (s, 3H), 2.2 (s, 3H), 2.28 (s, 3H), 2.36 (s, 3H), 2.8 (m, 2H), 3.2 (m, 2H), 3.5 (m, 1H), 3.65 (m, 2H), 3.85 (s, 3H), 4.0 (d, 2H), 7.05 (d, 1H), 7.1 (m, 2H), 7.25 (d, 1H), 7.4–7.68 (s, 1H), 7.7 (s, 1H), 8.4 (s, 1H), 11.2 (s, 1H): Mass Spectrum M+H$^+$ 560.

[158] The product gave the following data: NMR Spectrum: (DMSOd$_6$, 100° C.) 1.42 (m, 2H), 1.8 (m, 3H), 1.95 (m, 2H), 2.2 (s, 3H), 2.25 (m, 9H), 2.3 (s, 3H), 2.55 (m, 2H), 2.8 (m, 2H), 3.6 (m, 2H), 3.8 (s, 3H), 4.0 (d, 2H), 7.0 (d, 1H), 7.06 (s, 1H), 7.15 (s, 1H), 7.2 (d, 1H), 7.3–7.6 (s, 1H), 8.4 (s, 1H), 11.1 (s, 1H); Mass Spectrum: M+H$^+$ 520.

[159] The product gave the following data: Mass Spectrum M+H$^+$ 580.

[160] The product gave the following data: Mass Spectrum M+H$^+$ 600.

[161] The product gave the following data: Mass Spectrum M+H$^+$ 584.

The 1-(2-bromophenyl)-3-[6-methoxy-7-(N-methylpiperidin-4-ylmethoxy)quinazolin-4-yl]thiourea used as a starting material was prepared as follows:—

4-Amino-6-methoxy-7-(N-methylpiperidin-4-ylmethoxy)quinazoline was reacted with 2-bromo isothiocyanate using an analogous procedure to that described in the last paragraph of the portion of Example 1 which is connected with the preparation of starting materials. There was thus obtained the required starting material, which was used without further purification.

[162] The product gave the following data: NMR Spectrum (DMSOd$_6$, 100° C.) 1.2 (m, 1H), 1.55 (m, 1H), 1.7–1.85 (m, 4H), 1.9–2.15 (m, 9H), 2.2 (s, 3H), 2.25 (s, 6H), 2.35 (t, 2H), 2.6 (m, 1H), 2.8 (m, 1H), 3.6 (t, 2H), 3.8 (s, 3H), 4.05 (d, 2H), 7.05 (s, 1H), 7.2 (m, 3H), 7.7 (s, 1H), 8.4 (s, 1H), 10.8 (s, 1H); Mass Spectrum M+H$^+$ 534.

The 1-(2,6-dimethylphenyl)-3-[6-methoxy-7-(N-methylpiperidin-3-ylmethoxy)quinazolin-4-yl]thiourea used as a starting material was prepared as follows:—

4-Amino-6-methoxy-7-(N-methylpiperidin-3-ylmethoxy)quinazoline was prepared by reaction of 4-amino-6-methoxy-7-hydroxyquinazoline with 1-methyl-3-piperidinemethanol under analogous conditions to those described Example 2, Note[11]:—Mass Spectrum: M+H$^+$ 303.

4-Amino-6-methoxy-7-(N-methylpiperidin-3-ylmethoxy)quinazoline was reacted with 2,6-dimethylphenyl isothiocyanate using an analogous procedure to that described in the last paragraph of the portion of Example 1 which is concerned with the preparation of starting materials. There was thus obtained the required starting material.

[163] The product gave the following data: NMR Spectrum: (DMSOd$_6$) 0.86 (t, 6H), 1.46 (m, 4H), 2.25 (s, 6H), 2.5 (m, 6H), 2.91 (t, 2H), 3.64–4.0 (m, 7H), 6.7 (br s, 1H), 7.2 (s, 3H), 7.66 (s, 1H), 7.85 (s, 1H), 8.48 (s, 1H), 12.2 (br s, 1H): Mass Spectrum: M+H$^+$ 512.

The 4-amino-7-(3-dipropylamino-1-propynyl)-6-methoxyquinaozline used as a starting material was prepared as follows:—

4-(2-Bromo-4-fluorophenoxy)-6-methoxy-7-trifluoromethanesulphonyloxyquinazoline was reacted with 3-dipropylamino-1-propynyl to give 4-(2-bromo-4-fluorophenoxy)-7-(3-dipropylamino-1-propynyl)-6-methoxyquinazoline. The material so obtained was reacted with ammonia using an analogous procedure to that disclosed in International Patent Application WO 01/04102 (Example 2, third paragraph of the portion of Note [115] that is concerned with the preparation of starting materials) to give the required starting material.

EXAMPLE 3

N-(2-chloro-6-methylphenyl)-N'-[6-methoxy-7-(N-methylpiperidin-4-ylmethoxy)quinazolin-4-yl]-N''-(1,4-tetramethylene)guanidine Using an analogous procedure to that described in Example 1, 3-[6-methoxy-7-(N-methylpiperidin-4-ylmethoxy)quinazolin-4-yl]thiourea was reacted with pyrrolidine to give the title compound in 37% yield; NMR Spectrum: (DMSOd$_6$, 100° C.) 1.41 (m, 2H), 1.76–1.9 (m, 10H), 1.99 (t, 2H), 2.2 (s, 3H), 2.8 (d, 2H), 3.35 (t, 4H), 3.9 (s, 3H), 4.01 (t, 2H), 7.1 (s, 1H), 7.14 (s, 1H), 7.21 (d, 1H), 7.32 (d, 1H), 7.69 (s, 1H), 8.4 (s, 1H), 11.8 (br s, 1H); Mass Spectrum: M+H$^+$ 523 and 525.

EXAMPLE 4

N-carboxymethyl-N'-(2,6-dimethylphenyl)-N''-[6-methoxy-7-(N-methylpiperidin-4-ylmethoxy)quinazolin-4-yl] guanidine A mixture of N-(tert-butoxycarbonylmethyl)-N'-(2,6-dimethylphenyl)-N''-[6-methoxy-7-(N-methylpiperidin-4-ylmethoxy)quinazolin-4-yl]guanidine (0.09 g), trifluoroacetic acid (1 ml) and methylene chloride (1 ml) was stirred at ambient temperature for 3 hours. The reaction mixture was evaporated and the residue was purified by column chromatography on silica using increasingly polar mixture of methylene chloride and a 2M solution of ammonia gas in methanol as eluent. There was thus obtained the title compound in 67% yield: NMR Spectrum: (DMSOd$_6$, 100° C.) 1.2–1.5 (m, 3H), 1.7–1.9 (m, 2H), 2.0–2.1 (m, 2H), 2.14 (s, 3H), 2.19 (s, 6H), 2.84 (d, 2H), 3.82 (s, 3H), 3.95–4.05 (m, 4H), 7.08 (s, 1H), 7.17 (s, 3H), 7.71 (s, 1H), 8.43 (s, 1H); Mass Spectrum: M+H$^+$ 507.

EXAMPLE 5

N-carboxymethyl-N'-(2,6-dimethylphenyl)-N"-[6-methoxy-7-(2-pyrrolidin-1-ylethoxy)quinazolin-4-yl]guanidine Using an analogous procedure to that described in Example 4, N-(tert-butoxycarbonylmethyl)-N'-(2,6-dimethylphenyl)-N"-[6-methoxy-7-(2-pyrrolidin-1-ylethoxy)quinazolin-4-yl]guanidine was reacted with trifluoroacetic acid to give the title compound in 65% yield; NMR Spectrum: (DMSOd$_6$, 100° C.) 1.78 (m, 4H), 2.32 (s, 6H), 2.67 (m, 4H), 2.94 (t, 2H), 3.85 (s, 3H), 4.09 (s, 2H), 4.28 (t, 2H), 7.1 (s, 1H), 7.19 (s, 3H), 7.74 (s, 1H), 8.48 (s, 1H), 10.8–11.7 (br s, 1H); Mass Spectrum: M+H$^+$ 493.

EXAMPLE 6

N-(2-aminoethyl)-N'-(2,6-dimethylphenyl)-N"-[6-methoxy-7-(N-methylpiperidin-4-ylmethoxy)quinazolin-4-yl]guanidine A mixture of N-(2-tert-butoxycarbonylaminoethyl)-N'-(2,6-dimethylphenyl)-N"-[6-methoxy-7-(N-methylpiperidin-4-ylmethoxy)quinazolin-4-yl]guanidine (0.31 g), trifluoroacetic acid (1 ml) and methylene chloride (1 ml), was stirred at ambient temperature for 20 minutes. The reaction mixture was evaporated and the residue was dissolved in water (4 ml) and the solution was basified to pH10 by the addition of 10N aqueous potassium hydroxide solution. The mixture was extracted with a 19:1 mixture of methylene chloride and methanol. The organic extract was dried over magnesium sulphate and evaporated. There was thus obtained the title compound (0.16 g); NMR Spectrum: (DMSOd$_6$) 1.2–1.4 (m, 2H), 1.65–1.94 (m, 5H),2.12 (s, 3H), 2.21 (s, 6H), 2.7–2.9 (m, 4H), 3.22 (br s, 3H), 3.4–3.8 (m, 4H), 3.91 (d, 2H), 7.0 (s, 1H), 7.13 (s, 3H), 8.4 (s, 1H); Mass Spectrum: M+H$^+$ 492.

EXAMPLE 7

N-(2-chloro-6-methylphenyl)-N'-[6-methoxy-7-(3-pyrrolidin-1-ylpropoxy)quinazolin-4-yl]-N"-(3-methylaminopropyl)guanidine A mixture of N-[3-(N-tert-butoxycarbonyl)-N-methylaminopropyl)-N'-(2-chloro-6-methylphenyl)-N"-[6-methoxy-7-(3-pyrrolidin-1-ylpropoxy)quinazolin-4-yl]guanidine (0.42 g), trifluoroacetic acid (1.35 ml) and methylene chloride (15 ml) was stirred at ambient temperature for 3 hours. The reaction mixture was evaporated and the residue was dissolved in water (6 ml) and the solution was basified by the addition of a saturated aqueous sodium bicarbonate solution. The mixture was extracted with a 19:1 mixture of methylene chloride and methanol. The organic extract was dried over magnesium sulphate and evaporated. The residue was purified by column chromatography on silica using increasingly polar mixtures of methylene chloride and a 2M solution of ammonia gas in methanol as eluent. There was thus obtained the title compound (0.12 g); NMR Spectrum: (DMSOd$_6$, 100° C.) 1.72 (m, 4H), 1.82 (m, 2H), 1.96 (m, 2H), 2.29 (s, 3H), 2.32 (s, 3H), 2.63 (t, 2H), 2.45–2.55 (m, 4H), 2.69 (t, 2H), 3.61 (t, 2H), 3.73 (s, 3H), 4.19 (t, 2H), 7.09 (s, 1H), 7.27 (t, 1H), 7.34 (d, 1H), 7.41 (d, 1H), 7.48 (s, 1H), 8.46 (s, 1H); Mass Spectrum: M+H$^+$ 540 and 542.

EXAMPLE 8

Using an analogous procedure to that described in Example 7, the appropriate N-tert-butoxycarbonyl protected guanidine derivative was reacted with trifluoroacetic acid to give the compounds described in Table II.

TABLE II

| No. & Note | R$^6$ | R$^1$ | (R$^2$)$_n$ |
|---|---|---|---|
| [1] | 3-methylaminopropyl | 2-morpholinoethoxy | 2-methyl |
| [2] | 3-methylaminopropyl | 2-morpholinoethoxy | 2-chloro-6-methyl |
| [3] | 3-methylaminopropyl | 2-morpholinoethoxy | 2,6-dichloro |
| [4] | 2-piperidin-2-ylethyl | N-methylpiperidin-4-ylmethoxy | 2,6-dimethyl |

Notes

[1] The product gave the following data: NMR Spectrum: (DMSOd$_6$, 100° C.) 2.01 (m, 2H), 2.45 (s, 3H), 2.5 (s, 3H), 2.68 (t, 4H), 2.92 (m, 4H), 3.73 (m, 6H), 3.95 (s, 3H), 4.4 (t, 2H), 7.27 (s, 1H), 7.33 (t, 1H), 7.41 (t, 1H), 7.48 (d, 2H), 7.69 (s, 1H), 8.6 (s, 1H); Mass Spectrum: M + H$^+$ 508.
[2] The product gave the following data: NMR Spectrum: (DMSOd$_6$, 100° C.) 1.69 (m, 2H), 2.16 (d, 6H), 2.39 (t, 4H), 2.6 (t, 2H), 2.65 (t, 2H), 3.42 (m, 6H), 3.59 (s, 3H), 4.1 (t, 2H), 6.95 (s, 1H), 7.09 (t, 1H), 7.16 (d, 1H), 7.25 (d, 1H), 7.31, (s, 1H), 8.29 (s, 1H); Mass Spectrum: M + H$^+$ 542 and 544.
[3] The product gave the following data: NMR Spectrum: (DMSOd$_6$, 100° C.) 1.89 (m, 2H), 2.4 (s, 3H), 2.51 (t, 4H), 2.79 (m, 4H), 3.58 (m, 6H), 3.73 (s, 3H), 4.26 (t, 2H), 7.11 (s, 1H), 7.34 (t, 1H), 7.4 (s, 1H), 7.58 (d, 2H), 8.47 (s, 1H); Mass Spectrum: M + H$^+$ 562 and 564.
[4] The product gave the following data: NMR Spectrum: (DMSOd$_6$ and CD$_3$CO$_2$D, 100° C.) 1.34–1.48 (m, 2H), 1.52–1.76 (m, 5H), 1.8–2.11 (m, 6H), 2.21 (s, 6H), 2.26 (s, 1H), 2.64 (s, 3H), 2.75–2.86 (m, 3H), 3.0–3.06 (m, 1H), 3.2 (d, 2H), 3.31 (d, 2H), 3.53–3.67 (m, 2H), 3.8 (s, 3H), 4.04 (s, 2H), 7.08–7.22 (m, 3H), 7.62 (s, 1H), 8.45 (s, 1H); Mass Spectrum: M + H$^+$ 560.

EXAMPLE 9

N-(2-amidinoethyl)-N'-(2,6-dimethylphenyl-N"-[6-methoxy-7-(3-morpholinopropoxy)quinazolin-4-yl]guanidine A 4M solution of hydrogen chloride in dioxane (0.75 ml) was added to a mixture of N-(2-cyanoethyl)-N'-(2,6-dimethylphenyl)-N"-[6-methoxy-7-(3-morpholinopropoxy)quinazolin-4-yl]guanidine (0.025 g), methanol (0.002 ml), dioxane (0.5 ml) and methylene chloride (0.25 ml). The resultant suspension was stirred at ambient temperature for 16 hours. A further aliquot of methanol (0.002 ml) was added and the mixture was stirred at ambient temperature for a further 16 hours. The mixture of evaporated and the residue was dissolved in a 2M solution of ammonia in ethanol. The resultant solution was allowed to stand for 2 days. The mixture was evaporated. There was thus obtained the title compound (0.022 g); Mass Spectrum: M+H$^+$ 535.

EXAMPLE 10

N-(3-dimethylaminopropyl)-N'-(2,6-dimethylphenyl)-N"-(7-hydroxy-6-methoxyquinazolin-4-yl)guanidine A mixture of N-(7-benzyloxy-6-methoxyquinazolin-4-yl)-N'-(3-dimethylaminopropyl)-N"-(2,6-dimethylphenyl)guanidine (2.21 g) and trifluoroacetic acid (40 ml) was stirred and heated to 70° C. for 16 hours. The reaction mixture was evaporated and the residue was partitioned between ethyl acetate and a saturated aqueous sodium bicarbonate solution. The organic layer was dried over magnesium sulphate, filtered and evaporated and the residue was purified by column chromatography on silica using increasingly polar mixtures of methylene chloride and a 2M solution of ammonia gas in methanol as eluent. There was thus obtained the title compound (1.66 g); NMR Spectrum: (DMSOd$_6$, 100° C.) 1.77 (m, 2H), 2.07 (s, 6H), 2.29 (s, 6H), 2.36 (t, 2H), 3.59 (t, 2H), 3.81 (s, 3H), 7.0 (s, 1H), 7.19 (m, 3H), 7.67 (s, 1H), 8.4 (s, 1H), 9.4 (br s, 1H), 10.8 (br s, 1H); Mass Spectrum: M+H$^+$ 423.

EXAMPLE 11

N-(6,7-dimethoxyquinazolin-4-yl)-N'-(3-dimethylaminopropyl)-N"-(2,6-dimethylphenyl)guanidine An aliquot (0.15 ml) of a 2M solution of trimethylsilyldiazomethane in hexane was added to a mixture of N-(3-dimethylaminopropyl)-N'-(2,6-dimethylphenyl)-N"-(7-hydroxy-6-methoxyquinazolin-4-yl)guanidine (0.1 g), N,N-diisopropylethylamine (0.06 ml), acetonitrile (1.8 ml) and methanol (0.2 ml). The resultant reaction mixture was stirred at ambient temperature for 16 hours. The mixture was evaporated and the residue was purified by column chromatography on silica using increasingly polar mixtures of methylene chloride and a 2M solution of ammonia gas in methanol as eluent. There was obtained the title compound (0.059 g); NMR Spectrum: (DMSOd$_6$, 100° C.) 1.78 (m, 2H), 2.06 (s, 6H), 2.3 (s, 6H), 2.38 (t, 2H), 3.6 (q, 2H), 3.81 (s, 3H), 3.93 (s, 3H), 7.11 (s, 1H), 7.2 (s, 3H), 7.66 (s, 1H), 8.47 (s, 1H), 10.9 (br s, 1H); Mass Spectrum: M+H$^+$ 473.

EXAMPLE 12

N-(2-dimethylaminoethyl)-N'-(2,6-dimethylphenyl)-N"-(7-hydroxy-6-methoxyquinazolin-4-yl)guanidine Using an analogous procedure to that described in Example 10, N-(7-benzyloxy-6-methoxyquinazolin-4-yl)-N'-(2-dimethylaminoethyl)-N"-(2,6-dimethylphenyl)guanidine was reacted with trifluoroacetic acid to give the title compound in 68% yield; NMR Spectrum: (DMSOd$_6$, 100° C.) 2.22 (s, 6H), 2.26 (s, 6H), 2.55 (t, 2H), 3.6 (t, 2H), 3.79 (s, 3H), 6.99 (s, 1H), 7.17 (s, 3H), 7.6 (s, 1H), 8.39 (s, 1H), 9.4 (br s, 1H), 10.8 (br s, 1H); Mass Spectrum: M+H$^+$ 409.

EXAMPLE 13

N-(6,7-dimethoxyquinazolin-4-yl)-N'-(2-dimethylaminoethyl)-N"-(2,6-dimethylphenyl)guanidine Using an analogous procedure to that described in Example 11, N-(2-dimethylaminoethyl)-N'-(2,6-dimethylphenyl)-N"-(7-hydroxy-6-methoxyquinazolin-4-yl)guanidine was reacted with trimethylsilyldiazomethane to give the title compound in 63% yield; NMR Spectrum: (DMSOd$_6$, 100° C.) 2.21 (s, 6H), 2.24 (s, 6H), 2.54 (t, 2H), 3.57 (q, 2H), 3.75 (s, 3H), 3.9 (s, 3H), 7.08 (s, 1H), 7.17 (s, 3H), 7.58 (s, 1H), 8.43 (s, 1H), 10.8 (br s, 1H); Mass Spectrum: M+H$^+$ 423.

EXAMPLE 14

N-(3-dimethylaminopropyl)-N'-(2,6-dimethylphenyl)-N"-[6-methoxy-7-(N-methylpyrrolidin-3-yloxy)quinazolin-4-yl]guanidine 1,1'-(Azodicarbonyl)dipiperidin (0.36 g) was added to a mixture of N-(3-dimethylaminopropyl)-N'-(2,6-dimethylphenyl)-N"-(7-hydroxy-6-methoxyquinazolin-4-yl)guanidine (0.1 g), 3-hydroxy-N-methylpyrrolidine (0.143 g), tributylphosphine (0.35 ml) and THF (15 ml). The resultant mixture was stirred at ambient temperature for 2 days. The mixture was filtered and the filtrate was evaporated. The residue so obtained was purified by column chromatography on silica using increasingly polar mixtures of methylene chloride and a 2M solution of ammonia gas in methanol as eluent. There was thus obtained the title compound (0.052 g); NMR Spectrum: (DMSOd$_6$, 100° C.) 0.89 (t, 2H), 1.75 (m, 2H), 2.1 (s, 6H), 2.37 (s, 6H), 2.32 (s, 3H), 2.27 (m, 2H), 3.21 (t, 2H), 3.31 (t, 2H), 3.55 (t, 2H), 3.77 (s, 3H), 5.0 (t, 1H), 6.98 (s, 1H), 7.17 (s, 3H), 7.61 (s, 1H), 8.4 (s, 1H), 10.8 (br s, 1H); Mass Spectrum: M+H$^+$ 506.

EXAMPLE 15

Using an analogous procedure to that described in Example 14, the appropriate N-(7-hydroxyquinazolin-4-yl)guanidine was reacted with the appropriate alkylating agent to give the compounds described in Table III.

TABLE III

| No. & Note | $R^6$ | $R^1$ | $(R^2)_n$ |
|---|---|---|---|
| [1] | 3-methylaminopropyl | 2-(2-oxopyrrolidin-1-yl)ethoxy | 2,6-dimethyl |
| [2] | 3-methylaminopropyl | 2-(N-benzyl-N-methylamino)-ethoxy | 2,6-dimethyl |
| [3] | 3-methylaminopropyl | 1-dimethylaminomethylethoxy | 2,6-dimethyl |
| [4] | 3-dimethylaminopropyl | N-ethylpyrrolidin-3-yloxy | 2,6-dimethyl |
| [5] | 3-dimethylaminopropyl | N-methylpiperidin-2-ylmethoxy | 2,6-dimethyl |

Notes

[1] The product gave the following data: NMR Spectrum: (DMSOd$_6$, 100° C.) 1.75 (m, 2H), 1.94 (m, 2H), 2.02 (s, 6H), 2.2 (t, 2H), 2.24 (s, 6H), 2.33 (t, 2H), 3.56–3.62 (m, 6H), 3.8 (s, 3H), 4.25 (t, 2H), 7.1 (s, 1H), 7.18 (s, 3H), 7.64 (s, 1H), 8.41 (s, 1H), 10.84 (br s, 1H); Mass Spectrum: M + H$^+$ 534.

[2] The product gave the following data: NMR Spectrum: (DMSOd$_6$, 100° C.) 1.7 (m, 2H), 2.01 (s, 6H), 2.24 (s, 6H), 2.28 (s, 3H), 2.32 (m, 2H), 2.86 (t, 2H), 2.52 (m, 2H), 3.62 (s, 2H), 3.88 (s, 3H), 4.22 (t, 2H), 7.08 (s, 1H), 7.15 (m, 3H), 7.3 (m, 5H), 7.62 (s, 1H), 8.41 (s, 1H), 10.85 (br s, 1H); Mass Spectrum: M + H$^+$ 570.

[3] The product gave the following data: NMR Spectrum: (DMSOd$_6$, 100° C.) 1.32 (d, 3H), 1.75 (m, 2H), 1.94 (m, 2H), 2.03 (s, 6H), 2.23 (s, 12H), 2.32 (t, 2H), 3.56 (t, 2H), 3.77 (s, 3H), 4.7 (m, 1H), 7.11 (s, 1H), 7.18 (s, 3H), 7.62 (s, 1H), 8.41 (s, 1H), 10.8 (br s, 1H); Mass Spectrum: M + H$^+$ 508.

[4] The product gave the following data: NMR Spectrum: (DMSOd$_6$, 100° C.) 1.04 (t, 3H), 1.74 (m, 2H), 1.85 (q, 1H), 1.89 (m, 1H), 2.04 (s, 6H), 2.25 (s, 6H), 2.32 (q, 2H), 2.64 (m, 1H), 2.74 (m, 2H), 3.22 (t, 2H), 3.32 (t, 2H), 3.55 (q, 2H), 3.78 (s, 3H), 4.99 (m, 1H), 6.99 (s, 1H), 7.17 (s, 3H), 7.63 (br s, 1H), 8.42 (s, 1H), 10.5–11.1 (br s, 1H); Mass Spectrum: M + H$^+$ 520.

[5] The product gave the following data: NMR Spectrum: (DMSOd$_6$, 100° C.) 1.75 (m, 2H), 2.07 (s, 6H), 2.23 (s, 3H), 2.28 (s, 6H), 2.35 (t, 2H), 3.19 (m, 4H), 3.32 (m, 4H), 3.54 (m, 1H), 3.56 (t, 2H), 3.81 (s, 3H), 4.03 (m, 1H), 4.26 (m, 1H), 7.06 (s, 1H), 7.18 (s, 3H), 7.63 (br s, 1H), 8.21 (s, 1H), 8.45 (s, 1H), 10.6–11.1 (br s, 1H); Mass Spectrum: M + H$^+$ 534.

EXAMPLE 16

Using an analogous procedure to that described in Example 1, the appropriate 1-aryl-3-quinazolin-4-ylthiourea was reacted with the appropriate amine to give the compounds described in Table IV.

TABLE IV

| No. & Note | $R^6$ | $R^1$ | $(R^2)_n$ |
|---|---|---|---|
| [1] | 2-dimethylaminoethyl | 1,4-benzodioxan-2-ylmethoxy | 2,6-dimethyl |
| [2] | 2-dimethylaminoethyl | cyclohex-1-en-4-ylmethoxy | 2,6-dimethyl |
| [3] | 2-dimethylaminoethyl | tetrahydropyran-4-yloxy | 2,6-dimethyl |
| [4] | 2-dimethylaminoethyl | tetrahydropyran-2-ylmethoxy | 2,6-dimethyl |
| [5] | 2-dimethylaminoethyl | tetrahydrofuran-3-yloxy | 2,6-dimethyl |
| [6] | 2-dimethylaminoethyl | tetrahydrofuran-2-ylmethoxy | 2,6-dimethyl |
| [7] | 2-dimethylaminoethyl | tetrahydrofuran-3-ylmethoxy | 2,6-dimethyl |
| [8] | 2-dimethylaminoethyl | 2-(2-methoxyethoxy)ethoxy | 2,6-dimethyl |
| [9] | 2-(N-methylpyrrolidin-2-yl)ethyl | tetrahydrofuran-3-ylmethoxy | 2,6-dimethyl |

TABLE IV-continued

| No. & Note | R⁶ | R¹ | (R²)ₙ |
|---|---|---|---|
| [10] | tetrahydrofuran-2-ylmethyl | 3-morpholinopropoxy | 2,6-dimethyl |
| [11] | 2-cyanoethyl | 3-morpholinopropoxy | 2,6-dimethyl |
| [12] | 2-dimethylaminoethyl | 3-morpholinopropoxy | 2,6-dimethyl |
| [13] | 3-hydroxypropyl | 3-morpholinopropoxy | 2,6-dimethyl |
| [14] | 2,3-dihydroxypropyl | 3-morpholinopropoxy | 2,6-dimethyl |
| [15] | 2-dimethylaminoethyl | 2,2-dimethyl-1,3-dioxolan-4-ylmethoxy | 2,6-dimethyl |
| [16] | 2-dimethylaminoethyl | 2,3-dihydroxypropoxy | 2,6-dimethyl |
| [17] | 2-morpholinoethyl | tetrahydrofuran-3-yloxy | 2,6-dimethyl |

Notes
[1] The product gave the following data: NMR Spectrum: (DMSOd₆) 2.2 (s, 12H), 3.56 (m, 2H), 3.9 (s, 3H), 4.18 (q, 1H), 4.43 (m, 1H), 4.65 (m, 1H), 6.8–7.2 (m, 9H), 8.41 (s,1H), 12.1–12.4 (br m, 1H); Mass Spectrum: M + H⁺ 557.

The 1-[6-(1,4benzodioxan-2-ylmethoxy)-7-methoxyquinazolin-4-yl]-3-(2,6-dimethylphenyl)thiourea used as a starting material was prepared as follows;—

A mixture of 6-acetoxy-7-methoxyquinazolin-4-one (International Patent Application WO 96/15118, Example 39 thereof; (15 g), thionyl chloride (215 ml) and DMF (4.3 ml) was stirred and heated to 90° for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 6-acetoxy-4-chloro-7-methoxyquinazoline (14.8 g) which was used without further purification.

Sodium hydride (60% dispersion in mineral oil; 4.8 g) was added portionwise to a stirred solution of 4-chloro-2-fluorophenol (17.5 g) in DMF (100 ml) which had been cooled in an ice bath. The mixture was allowed to warm to ambient temperature and was stirred for 0.5 hours. 6-Acetoxy-4-chloro-7-methoxyquinazoline (10 g) was added and the mixture was stirred and heated to 100° C. for 5 hours. The mixture was evaporated under vacuum and the residue was partitioned between ethyl acetate and a dilute aqueous citric acid solution. The resultant solid was isolated and washed in turn with water and diethyl ether. The material so obtained was dried under vacuum at 80° C. There was thus obtained 4-(4-chloro-2-fluorophenoxy)-6-hydroxy-7-methoxyquinazoline (5.3 g); NMR Spectrum: (DMSOd₆) 3.99 (s, 3H), 7.3"7.7 (m, 5H), 8.5 (s, 1H), 10.4 (s, 1H); Mass Spectrum: M+H⁺ 321.

Diisopropyl azodicarboxylate (0.8 ml) was added dropwise during 10 minutes to a stirred mixture of 4-(4-chloro-2-fluorophenoxy)-6-hydroxy-7-methoxyquinazoline (0.4 g), 2-hydroxymethyl-1,4-benzodioxan (0.62 g), triphenylphosphine (0.99 g) and toluene (25 ml) that had been cooled in an ice bath. The temperature was maintained at approximately 10° C. during the addition. The reaction mixture was allowed to warm to ambient temperature and was stirred for a further 3 hours. The mixture was partitioned between ethyl acetate and a dilute aqueous potassium carbonate solution. The organic solution was washed with brine, dried over magnesium sulphate and evaporated. The residue was purified by column chromatography on silica using increasingly polar mixtures of isohexane and ethyl acetate as eluent. There was thus obtained 6-(1,4-benzodioxan-2-ylmethoxy)-4-(4-chloro-2-fluorophenoxy)-7-methoxyquinazoline (0.55 g); NMR Spectrum: (DMSOd₆) 4.01 (s, 3H), 4.19 (m, 1H), 4.46 (m, 3H), 4.66 (m, 1H), 6.8–6.95 (m, 4H), 7.4–7.5 (m, 5H), 8.59 (s, 1H); Mass Spectrum: M+H⁺ 469.

The material so obtained was reacted with ammonia using an analogous procedure to that described in the second last paragraph of the portion of Example 1 that is concerned with the preparation of starting materials. There was thus obtained 4-amino-6-(1,4-benzodioxan-2-ylmethoxy)-7-methoxyquinazoline which was reacted with 2,6-dimethylphenyl isothiocyanate using an analogous procedure to that described in the last paragraph of the portion of Example 1 that is concerned with the preparation of starting materials. There was thus obtained 1-[6-(1,4-benzodioxan-2-ylmethoxy)-7-methoxyquinazolin-4-yl]-3-(2,6-dimethylphenyl)thiourea; Mass Spectrum: M+H⁺ 503.

[2] The product gave the following data: NMR Spectrum: (CDCl₃) 1.45 (m, 1H), 1.96 (m, 2H), 2.1–2.38 (br, m, 16H), 2.5 (m, 2H), 3.6 (m, 2H), 4.0 (s, 3H), 4.04 (m, 2H), 5.73 (s, 2H), 7.15 (m, 5H), 8.55 (m, 1H); Mass Spectrum: M+H⁺ 503.

The 1-(6-cyclohexyl-1-en-4-ylmethoxy-7-methoxyquinazolin-4-yl)-3-(2,6-dimethylphenyl)thiourea used as a starting material was prepared as follows:—

4-(4-Chloro-2-fluorophenoxy)-6-hydroxy-7-methoxyquinazoline was reacted with cyclohex-1-en-4-ylmethanol using an analgous procedure to that described in the second last paragraph of Note [1] immediately above that is concerned with the preparation of starting materials. There was thus obtained 6-cyclohex-1-en-4-ylmethoxy-4-(4-chloro-2-fluorophenoxy)-7-methoxyquinazoline; NMR Spectrum: (CDCl₃) 1.46 (m, 1H), 1.98 (m, 2H), 2.13 (m, 2H), 2.3 (m, 2H), 4.03 (s, 3H), 4.04 (m, 2H), 5.72 (q, 2H), 7.2–7.35 (m, 4H), 7.51 (s, 1H), 8.6 (s, 1H); Mass Spectrum: M+H⁺ 415.

The material so obtained was reacted with ammonia using an analogous procedure to that described in the second last paragraph of the portion of Example 1 that is concerned with the preparation of starting materials. There was thus obtained 4-amino-6-cyclohex-1-en-4-ylmethoxy)-7-methoxyquinazoline which, in turn, was reacted with 2,6-dimethylphenyl isothiocyanate using an analogous procedure to that described in the last paragraph of the portion of Example 1, that is concerned with the preparation of starting materials. There was thus obtained 1-(6-cyclohex-1-en-4-ylmethoxy-7-methoxyquinazolin-4-yl)-3-(2,6-dimethylphenyl)thiourea; Mass Spectrum: M+H$^+$ 503.

[3] The product gave the following data: NMR Spectrum: (DMSOd$_6$) 1.6 (br m, 2H), 1.97 (br m, 2H), 2.2 (s, 12H), 3.4–3.6 (m, 4H), 3.85 (m, 2H), 3.9 (s, 3H), 7.17 (s, 3H), 8.43 (s, 1H); Mass Spectrum: M+H$^+$ 493.

The 1-(2,6-dimethylphenyl)-3-(7-methoxy-6-tetrahydropyran-4-yloxyquinazolin-4-yl)thiourea used as a starting material was prepared as follows:—

6-Acetoxy-4-chloro-7-methoxyquinzoline (10 g), was added portionwise to a solution of 4-methoxybenzylamine (15.5 ml) in isopropanol (100 ml) and the resultant mixture was stirred and heated to reflux for 4 hours. The mixture was filtered and the filtrate was evaporated. The residue was partitioned between ethyl acetate and brine. The organic solution was evaporated and the crude product was purified by column chromatography on silica using increasingly polar mixtures of methylene chloride and methanol as eluent. There was thus obtained 6-hydroxy-4-(4-methoxybenzylamino)-7-methoxyquinaozline (8.6 g); NMR Spectrum: (DMSOd$_6$) 3.7 (s, 3H), 3.91 (s, 3H), 4.63 (d, 2H), 6.82 (d, 2H), 7.08 (s, 1H), 7.25 (d, 2H), 7.49 (s, 1H), 8.18 (t, 1H), 8.25 (s, 1H), 9.38 (s, 1H); Mass Spectrum: M+H$^+$ 312.

The material so obtained was reacted with 4-hydroxytetrahydropyran using an analogous procedure to that described in the second last paragraph of Note [1] immediately above that is concerned with the preparation of starting materials. There was thus obtained 4-(4-methoxybenzylamino)-7-methoxy-6-tetrahydropyran-4-yloxyquinazoline; NMR Spectrum: (CDCl$_3$) 1.83 (m, 2H), 2.0 (m, 2H), 3.5 (m, 2H), 3.8 (s, 3H), 3.96 (s, 3H), 4.0 (m, 2H), 4.5 (m, 1H), 4.78 (d, 2H), 5.6 (t, 1H), 6.88 (d, 2H), 7.02 (s, 1H), 7.2 (s, 1H), 7.32 (d, 2H), 8.58 (s, 1H); Mass Spectrum: M+H$^+$ 396.

A portion (0.54 g) of the material so obtained was dissolved in a solution of trifluoroacetic acid (5 ml) containing anisole (0.2 ml) and concentrated sulphuric acid (3 drops) and the resultant mixture was stirred and heated to 60° C. for 16 hours. The mixture was evaporated. The residue was partitioned between diethyl ether and a dilute aqueous potassium carbonate solution. A solid was precipitated which was isolated and washed in turn with water and diethyl ether. The solid was dried under vacuum at 70° C. There was thus obtained 4-amino-7-methoxy-6-tetrahydropyran-4-yloxyquinazoline which was used without further purification.

The material so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-(7-methoxy-6-tetrahydropyran-4-yloxyquinazolin-4-yl) thiourea; Mass Spectrum: M+H$^+$ 439.

[4] The product gave the following data: NMR Spectrum: (DMSOd$_6$) 1.32 (m, 1H), 1.5 (m, 3H), 1.65 (m, 1H), 1.85 (m, 1H), 2.2 (s, 12H), 3.4 (m, 2H), 3.55 (m, 2H), 3.66 (m, 1H), 3.88 (s, 3H), 3.93 (m, 2H), 5.76 (s, 1H), 7.02–7.2 (m, 4H), 8.4 (s, 1H); Mass Spectrum: M+H$^+$ 507.

The 1-(2,6-dimethylphenyl)-3-(7-methoxy-6-tetrahydrofuran-2-ylmethoxyquinazolin-4-yl)thiourea used as a starting material was prepared as follows:—

6-Hydroxy-4-(4-methoxybenzylamino)-7-methoxyquinazoline was reacted with tetrahydropyran-2-ylmethanol using an analogous procedure to that described in the second last paragraph of Note [1] immediately above that is concerned with the preparation of starting materials. There was thus obtained 4-(4methoxybenzylamino)-7-methoxy-6-tetrahydropyran-2-methoxyquinazoline; NMR Spectrum: (CDCl$_3$) 1.3–2.0 (m, 6H), 3.5 (m, 2H), 3.8 (s, 3H), 3.98 (s, 3H), 4.0–4.15 (m, 3H), 4.76 (d, 2H), 5.62 (t, 1H), 6.9 (d, 2H), 6.95 (s, 1H), 7.19 (s, 1H), 7.32 (d, 2H), 8.59 (s, 1H); Mass Spectrum: M+H$^+$ 410.

The material so obtained was reacted with trifluoroacetic acid and concentrated sulphuric acid using an analogous procedure to that described in the second last paragraph of Note [3] immediately above that is concerned with the preparation of starting materials. There was thus obtained 4-amino-7-methoxy-6-tetrahydrofuran-2-ylmethoxyquinazoline which was used without further purification.

The material so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-(7-methoxy-6-tetrahydropyran-2-ylmethoxyquinazolin-4-yl)thiourea; Mass Spectrum: M+H$^+$ 453.

[5] The product gave the following data: NMR Spectrum: (CDCl$_3$) 2.1–2.35 (m, 14H), 2.46 (m, 2H), 3.6 (m, 2H), 3.9–4.2 (br m, 7H), 4.9 (m, 1H), 5.1 (m, 1H), 7.15 (s, 4H), 7.87 (br s, 1H), 8.55 (s, 1H), 12.5 (br s, 1H); Mass Spectrum: M+H$^+$ 479.

The 1-(2,6-dimethylphenyl)-3-(7-methoxy-6-tetrahydrofuran-3-yloxyquinazolin-4-yl)thiourea used as a starting material was prepared as follows:—

6-Hydroxy-4-(4-(4-methoxybenzylamino)-7-methoxyquinaozline was reacted with 3-hydroxytetrahydrofuran using an analogous procedure to that described in the second last paragraph of Note [1] immediately above that is concerned with the preparation of starting materials. There was thus obtained 4-(4-methoxybenzylamino)-7-methoxy-6-tetrahydrofuran-3-yloxyquinazoline; NMR Spectrum: (CDCl$_2$) 2.2 (m, 2H), 3.81 (s, 3H), 3.85–4.1 (m, 7H), 4.77 (d, 2H), 5.11 (m, 1H), 5.6 (t, 1H), 6.9 (m, 3H), 7.2 (s, 1H), 7.32 (d, 2H), 8.6 (s, 1H); Mass Spectrum: M+H$^+$ 382.

The material so obtained was reacted with triflouroacetic and concentrated sulphuric acid using an analogous procedure to that described in the second last paragraph of Note [3] immediately above that is concerned with the preparation of starting materials. There was thus obtained 4-amino-7-methoxy-6-tetrahydrofuran-3-yloxyquinazoline which was used without further purification.

The material so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-(7-methoxy-6-tetrahydrofuran-3-yloxyquinazolin-4-yl) thiourea; Mass Spectrum: M+H$^+$ 425.

[6] The product gave the following data: NMR Spectrum: (DMSO$_6$) 1.6–1.2 (m, 4H), 2.2 (s, 12H), 3.55 (m, 2H), 3.68–3.95 (m, 7H), 4.2 (m, 1H), 7.0–7.2 (m, 5H), 8.4 (s, 1H); Mass Spectrum: M+H$^+$ 493.

The 1-(2,6-dimethylphenyl)-3-(7-methoxy-6-tetrahydrofuran-2-ylmethoxyquinazolin-4-yl)thiourea used as a starting material was prepared as follows:—

6-Hydroxy-4-(4-(4-methoxybenzylamino)-7-methoxyquinazoline was reacted with tetrahydrofuran-2-ylmethanol using an analogous procedure in that described in the second last paragraph of Note [1] immediately above that is concerned with the preparation of starting materials. There was thus obtained 4-(4-methoxybenzylamino)-7-methoxy-6-tetrahydrofuran-2-ylmethoxyquinazoline; NMR Spectrum: (CDCl$_3$) 1.7–2.2 (m, 4H), 3.82 (s, 3H), 3.85–3.95 (m, 2H), 3.98 (s, 3H), 4.05 (d, 2H), 4.35 (m, 1H), 4.76 (d, 2H), 5.6 (t, 1H), 6.9 (m, 3H), 7.18 (s, 1H), 7.35 (d, 2H), 8.59 (s, 1H); Mass Spectrum: M+H$^+$ 396.

The material so obtained was reacted with trifluoroacetic acid and concentrated sulphuric acid using an analogous procedure to that described in the second last paragraph of Note [3] immediately above that is concerned with the preparation of starting materials. There was thus obtained 4-amino-7-methoxy-6-tetrahydrofuran-2-ylmethoxyquinazoline which was used without further purification.

The materials so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-(7-methoxy-6-tetrahydrofuran-2-ylmethoxyquinazolin-4-yl)thiourea; Mass Spectrum: M+H$^+$ 439.

[7] The product gave the following data: NMR Spectrum: (DMSOd$_6$) 1.65 (m, 1H), 2.05 (m, 1H), 2.22 (s, 12H), 2.7 (m, 2H), 3.5–3.95 (m, 11H), 7.02–7.2 (m, 4H), 8.4 (s, 1H); Mass Spectrum: M+H$^+$ 493.

The 1-(2,6-dimethylphenyl)-3-(7-methoxy-6-tetrahydrofuran-3-ylmethoxyquinazolin-4-yl)thiourea used as a starting material was prepared as follows:—

6-Hydroxy-4-(4-methoxybenzylamino)-7-methoxyquinazoline was reacted with tetrahydrofuran-3-ylmethanol using an analogous procedure to that described in the second last paragraph of Note [1] immediately above that is concerned with the preparation of starting materials. There was thus obtained 4-(4-methoxybenzylamino)-7-methoxy-6-tetrahydrofuran- 3-ylmethoxyquinazoline; NMR Spectrum: CDCl$_3$) 1.75 (m, 1H), 2.13 (m, 1H), 1.82 (m, 1H), 3.75 (m, 2H), 3.81 (s, 3H), 3.85 (m, 4H), 3.95 (s, 3H), 4.77 (d, 2H), 5.63 (t, 1H), 6.9 (m, 3H), 7.2 (s, 1H), 7.35 (d, 2H), 8.59 (s, 1H); Mass Spectrum: M+H$^+$ 396.

The material so obtained was reacted with trifluoroacetic acid and concentrated sulphuric acid using an analogous procedure to that described in the second last paragraph of Note [3] immediately above that is concerned with the preparation of starting materials. There was thus obtained 4-amino-7-methoxy-6-tetrahydrofuran-3-ylmethoxyquinazoline which was used without further purification.

The material so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-(7-methoxy-6-tetrahydrofuran-3-ylmethoxyquinazolin-4-yl)thiourea; Mass Spectrum: M+H$^+$ 439.

[8] The product gave the following data: NMR Spectrum: (CDCl$_3$) 2.18 (br s, 6H), 2.29 (s, 6H), 2.5 (m, 2H), 3.4 (s, 3H), 3.6 (m, 4H), 3.75 (m, 2H), 3.96 (m, 5H), 4.32 (m, 2H), 4.9 (br s, 1H), 7.15 (s, 4H), 7.9 (s, 1H), 8.56 (s, 1H), 12.5 (br s, 1H); Mass Spectrum: M+H$^+$ 511.

The 1-(2,6-dimethylphenyl)-3-{7-methoxy-6-[2-(2-methoxyethoxy)ethoxy]quinazolin-4-yl}thiourea used as a starting material was prepared as follows:—

6-Hydroxy-4-(4-methoxybenzylamino)-7-methoxyquinazoline was reacted with 2-(2-methoxyethoxy)ethanol using an analogous procedure to that described in the second last paragraph of Note [1] immediately above that is concerned with the preparation of starting materials. There was thus obtained (4-(4-methoxybenzylamino)-7-methoxy-6-[2-(2-methoxyethoxy)ethoxy]quinazoline; NMR Spectrum: (CDCl$_3$) 3.51 (m, 2H), 3.68 (m, 2H), 3.82 (s, 3H), 3.88 (m, 2H), 3.96 (s, 3H), 4.26 (m, 2H), 4.76 (d, 2H), 5.87 (t, 1H), 6.89 (d, 2H), 7.13 (s, 1H), 7.19 (s, 1H), 7.34 (d, 2H), 8.59 (s, 1H); Mass Spectrum: M+H$^+$ 414.

The material so obtained was reacted with trifluoroacetic acid and concentrated sulphuric acid using an analogous procedure to that described in the second last paragraph of Note [3] immediately above that is concerned with the preparation of starting materials. There was this obtained 4-amino-7-methoxy-6-[2-(2-methoxyethoxy)ethoxy] quinazoline which was used without further purification.

The material so obtained was reacted with 2,6-dimethylphenyl isothiocyanate using an analogous procedure to that described in the last paragraph of the portion of Example 1 that is concerned with the preparation of starting materials. There was thus obtained 1-(2,6-dimethylphenyl)-3-{7-methoxy-6-[2-(2-methoxyethoxy]quinazolin-4-yl}thiourea; Mass Spectrum: M+H$^+$ 457.

[9] The product gave the following data: NMR Spectrum: (CDCl$_3$) 1.5–2.0 (m, 12H), 2.15 (m, 1H), 2.29 (d, 6H),2.52 (m, 1H), 2.9 (m, 1H), 3.55 (m, 1H), 3.8 (m, 2H), 3.85 (m, 6H), 4.1 (m, 2H), 7.0 (br s, 1H), 7.16 (s, 4H), 7.91 (s, 1H), 8.5 (s, 1H); Mass Spectrum: M+H$^+$ 533.

[10] The product gave the following data: NMR Spectrum: (CDCl$_3$) 1.8–2.2 (m, 6H), 2.3 (s, 6H), 2.46 (m, 4H), 2.58 (m, 2H), 3.5–3.9 (m, 8H), 4.0 (s, 3H), 4.1–4.3 (m, 3H), 4.6 (br m, 1H), 7.15 (m, 4H), 7.9 (br m, 1H), 12.55 (br m, 1H); Mass Spectrum: M+H$^+$ 549.

The 1-(2,6-dimethylphenyl)-3-(7-methoxy-6-(3-morpholinopropoxy)quinazolin-4-yl)thiourea used as a starting material was obtained by the reaction of 4-amino-7-methoxy-6-(3-morpholinopropoxy)quinazoline (International Patent Appn. WO 01/04102, Example 25 thereof) with 2,6-dimethylphenyl isothiocyanate using an analogous procedurre to that described in the last paragraph of the portion of Example 1 that is concerned with the preparation of starting material.

[11] The product gave the following data: NMR Spectrum: (CDCl$_3$) 2.13 (m, 2H), 2.3 (s, 6H), 2.4–2.6 (m, 6H), 3.0 (m, 2H), 3.7–3.8 (m, 6H), 4.0 (s, 3H), 4.25 (t, 2H), 4.65 (br m, 1H), 7.19 (m, 4H), 7.82 (s, 1H), 8.6 (s, 1H), 12.55 (s, 1H); Mass Spectrum: M+H$^+$ 518.

[12] The product gave the following data: NMR Spectrum: (CDCl$_3$) 2.0–2.25 (m, 8H), 2.3 (s, 6H), 2.45–2.6 (m, 8H), 3.61 (m, 2H), 3.71 (m, 4H), 4.0 (s, 3H), 4.2 (br m, 2H), 4.8 (br m, 1H), 7.15 (m, 4H), 7.9 (br m, 1H), 8.55 (s, 1H), 12.55 (br m, 1H); Mass Spectrum: M+H$^+$ 536.

[13] The product gave the following data: NMR Spectrum: (CDCl$_3$) 1.78 (t, 2H), 2.14 (t, 2H), 2.34 (s, 6H), 2.5 (m, 4H), 2.6 (m, 2H), 3.65–3.8 (m, 8H), 4.0 (s, 3H), 4.28 (t, 2H), 4.45 (br m, 1H), 7.19 (s, 1H), 7.2 (s, 3H), 7.86 (s, 1H), 8.55 (s, 1H), 12.7 (s, 1H); Mass Spectrum: M+H$^+$ 523.

[14] The product was obtained as a dihydrochloride salt by the reaction of N-(2,2-dimethyl-1,3-dioxolan-4-ylmethyl)-N'-(2,6-diimethylphenyl)-N"-[6-methoxy-7-(3-morpholinopropoxy)quinazolin-4-yl]guanidine with a saturated solution of hydrogen chloride in methanol at ambient temperature for 1 hour and gave the following data: Mass Spectrum: M+H$^+$ 539.

The N-(2,2-dimethyl-1,3-dioxanolan-4-ylmethyl)-N'-(2,6-dimethylphenyl)-N"-[6-methoxy-7-(3-morpholinopropoxy)quinazolin-4-yl]guanidine used as a starting material was prepared by the reaction of 1-(2,6-dimethylphenyl)-3-[7-methoxy- 6-(3-morpholinopropoxy)quinazolin-4-yl]thiourea with 2,2-dimethyl-1,3-dioxolan-4-ylmethylamine using an analogous procedure to that described in Example 1. The material so obtained gave the following data: NMR Spectrum: (CDCl$_3$) 1.17 (s, 3H), 1.3 (s, 3H), 2.11 (m, 2H), 2.32 (m, 6H), 2.5 (m, 4H), 2.58 (m, 2H), 3.7–3.9 (m, 7H), 4.0–4.05 (m, 4H), 4.2 (m, 2H), 4.36 (m, 1H), 4.6 (br m, 1H), 7.19 (m, 4H), 7.85 (m, 1H), 8.58 (s, 1H), 12.55 (br m, 1H); Mass Spectrum: M+H$^+$ 579.

[15] The product gave the following data: NMR Spectrum: (CDCl$_3$) 1.4 (s, 3H), 1.5 (s, 3H), 2.2 (s, 6H), 2.3 (s, 6H), 2.49 (br m, 2H), 3.62 (m, 2H), 3.9–4.0 (m, 5H), 4.2 (m, 2H), 4.59 (m, 1H), 4.85 (br m, 1H), 7.1–7.2 (m, 4H), 7.95 (br m, 1H), 8.57 (s, 1H), 12.5 (br m, 1H); Mass Spectrum: M+H$^+$ 523.

The 1-(2,6-dimethylphenyl)-3-[7-methoxy-6-(2,2-dimethyl-1,3-dioxolan-4-ylmethoxy)quinazolin-4-yl]thiourea used as a starting material was prepared as follows:—

4-(4-Chloro-2-fluorophenoxy)-6-hydroxy-7-methoxyquinazoline was reacted with 2,2-dimethyl-1,3-dioxolan-4-ylmethanol using analogous conditions to those described in the third paragraph of the portion of Note [1] immediately above that is concerned with the preparation of starting materials. There was thus obtained 4-(4-chloro-2-fluorophenoxy)-6-(2,2-dimethyl-1,3-dioxolan-4-ylmethoxy)-7-methoxyquinazoline; NMR Spectrum: 1,4 (s, 3H) 1.5 (s, 3H), 3.95–4.05 (m, 4H), 4.1–4.3 (m, 3H), 4.65 (m, 1H), 7.15–7.3 (m, 4H), 7.6 (s, 1H), 8.6 (s, 1H); Mass Spectrum: M+H$^+$ 435.

The material so obtained was reacted with ammonia using an analogous procedure to that described in the second last paragraph of the portion of Example 1 that is concerned with the preparation of starting materials. There was obtained 4-amino-6-(2,2-dimethyl-1,3-dioxolan-4-ylmethoxy)-7-methoxyquinazoline which was reacted with 2,6-dimethylphenyl isothiocyanate using an analogous procedure to that described in the last paragraph of the portion of Example 1 that is concerned with the preparation of starting materials. There was thus obtained the required starting material.

[16] The product of Example 16[15] was reacted with sulphuric acid using an analogous procedure to that described in Note [14] immediately above to give the stated product as a dihydrochloride salt which gave the following data: NMR Spectrum: (DMSOd$_6$, 100° C.) 2.3 (s, 6H), 2.85 (s, 6H), 3.35 (m, 2H), 3.56 (m, 2H), 3.85–3.95 (m, 3H), 3.99 (s, 3H), 4.05–4.15 (br m, 1H), 7.1–7.25 (m, 4H), 7.65 (br m, 1H), 8.54 (s, 1H); Mass Spectrum: M+H$^+$ 483.

[17] The product gave the following data: NMR Spectrum: (CDCl$_3$) 2.32 (s, 6H), 2.3–2.4 (m, 6H), 2.54 (br m, 2H), 3.46 (m, 4H), 3.62 (m, 2H), 3.9–4.18 (m, 8H), 5.1 (br m, 2H), 7.18 (m, 4H), 7.86 (br m, 1H), 8.56 (s, 1H); Mass Spectrum: M+H$^+$ 521.

EXAMPLE 17

N-(2-carboxyethyl)-N'-(2,6-dimethylphenyl)-N''-[6-methoxy-7-(3-morpholinopropoxy)quinazolin-4-yl]guanidine A mixture of N-(2-methoxycarbonylethyl)-N'-(2,6-dimethylphenyl)-N''-[6-methoxy-7-(3-morpholinopropoxy) quinazolin-4-yl]guanidine (0.038 g), lithium hydroxide monohydrate (0.0063 g), THF (1 ml), methanol (0.5 ml) and water (0.5 ml) was stirred at ambient temperature for 16 hours. The mixture was evaporated and the residue was partitioned between water and methylene chloride. The aqueous layer was acidified by the addition of glacial acetic acid and evaporated. The resultant residue was extracted with methylene chloride. The organic extract was filtered and evaporated. There was thus obtained the title compound (0.034 g); NMR Spectrum: (CDCl$_3$) 2.15 (m, 2H), 2.28 (s, 6H), 2.58 (s, 3H), 2.6–2.73 (m, 7H), 3.73 (t, 4H), 3.83 (s, 2H), 4.0 (s, 4H), 4.2 (t, 2H), 7.14 (s, 3H), 7.2 (s, 1H), 7.87 (s, 1H), 8.51 (s, 1H), 12.5 (s, 1H); Mass Spectrum: M+H$^+$ 538.

EXAMPLE 18

N-[(S)-1-carboxyethyl]-N'-(2,6-dimethylphenyl)-N''-[6-methoxy-7-(2-pyrrolidin-1-ylethoxy) quinazolin-4-yl] guanidine Using an analogous procedure to that described in Example 4, N-[(S)-1-tert-butoxycarbonylethyl]-N'-(2,6-dimethylphenyl)-N''-[6-methoxy-7-(2-pyrrolidin-1ylethoxy)quinazolin-4-yl]guanidine was reacted with trifluoroacetic acid to give the title compound in 68% yield; NMR Spectrum: (DMSOd$_6$, 100° C.) 1.47 (d, 3H), 1.75 (m, 4H), 2.33 (s, 6H), 2.67 (m, 4H), 2.93 (t, 2H), 3.88 (s, 3H), 4.28 (t, 2H), 4.58 (q, 1H), 7.13 (s, 1H), 7.19 (s, 3H), 7.75 (s, 1H), 8.48 (s, 1H),11.5 (br s, 1H); Mass Spectrum: M+H$^+$ 505.

EXAMPLE 19

N-[(R)-1-carboxyethyl]-N'-(2,6-dimethylphenyl)-N''-[6-methoxy-7-(2-pyrrolidin-1-ylethoxy)quinazolin-4-yl]guanidine Using an analogous procedure to that described in Example 4,N-[(R)-1-tert-butoxycarbonylethyl]-N'-(2,6-dimethylphenyl)-N''-[6-methoxy-7-(2-pyrrolidin-1-ylethoxy)quinazolin-4-yl]guanidine was reacted with trifluoroacetic acid to give the title compound in 59% yield; NMR Spectrum: (DMSOd$_6$, 100° C.) 1.48 (d, 3H), 1.76 (m, 4H), 2.32 (s, 6H), 2.69 (m, 4H), 2.98 (t, 2H), 3.88 (s, 3H), 4.27 (t, 2H), 4.59 (q, 1H), 7.15 (s, 1H), 7.18 (s, 3H), 7.76 (s, 1H), 8.49 (s, 1H), 11.45 (br s, 1H); Mass Spectrum: M+H$^+$ 505.

EXAMPLE 20

N-carboxymethyl-N'-(2,6-dimethylphenyl)-N''-[6-methoxy-7-(2-morpholinoethoxy)quinazolin-4-yl]guanidine Using an analogous procedure to that described in Example 4, N-(tert-butoxycarbonylmethyl)-N'-(2,6-dimethylphenyl)-N''-[6-methoxy-7-(2-morpholinoethoxy)quinazolin-4-yl]guanidine was reacted with trifluoroacetic acid to give the title compound in 74% yield; NMR Spectrum: (DMSOd$_6$, 100° C.) 2.17 (s, 6H), 3.27 (t, 4H), 3.5 (t, 2H), 3.6 (s, 3H), 3.8 (t, 4H), 4.48 (m, 4H), 7.15 (s, 1H), 7.2 (d, 2H), 7.26 (t, 2H), 8.7 (s, 1H); Mass Spectrum: M+H$^+$ 509.

EXAMPLE 21

N-(2-dimethylaminoethyl)-N'-(2,6-dimethylphenyl)-N''-(6-methoxy-7-morpholin-3-ylmethoxyquinazolin-4-yl) guanidine A mixture of N-(2-dimethylaminoethyl)-N'-(2,6-dimethylphenyl)-N''-[7-(N-benzylmorpholin-3-ylmethoxy)-6-methoxyquinazolin-4-yl]guanidine (0.1 g), trifluoroacetic acid (0.091 ml), 10% palladium on carbon catalyst (0.03 g) and ethanol (12 ml) was stirred under an atmosphere pressure of hydrogen for 18 hours. The reaction was filtered and the filtrate was evaporated. The resulting gum was triturated under diethyl ether to give a solid which was dissolved in methylene chloride. The solution was washed with cooled 1N aqueous sodium hydroxide solution and with water. The organic solution was dried over magnesium sulphate and evaporated. There was thus obtained the title compound (0.069 g): NMR Spectrum: (CDCl$_3$) 2.1 (s, 6H), 2.26 (s, 6H), 2.39 (m, 2H), 2.9 (m, 2H), 3.36 (m, 2H), 3.55 (m, 3H), 3.78 (d, 2H), 3.80–4.08 (m, 5H), 4.79 (s, 1H), 7.1 (s, 4H), 7.85 (s, 1H), 8.47 (s, 1H), 12.5 (s, 1H); Mass Spectrum: M+H$^+$ 508.

EXAMPLE 22

N-(2-dimethylaminoethyl)-N'-(2,6-dimethylphenyl)-N''-(6-methoxy-7-morpholin-2-ylmethoxyquinazolin-4-yl) guanidine Using an analogous procedure to that described in Example 21, N-(2-dimethylaminoethyl)-N'-(2,6-dimethylphenyl)-N''-[7-(N-benzylmorpholin-2-ylmethoxy)-6-methoxyquinazolin-4-yl]guanidine was hydrogenated to give the title compound in 74% yield; NMR Spectrum: (CDCl$_3$) 2.19 (s, 6H), 2.31 (s, 6H), (m, 2H), 2.76–2.91 (m, 2H), 2.91–3.01 (m, 1H), 3.1 (d, 1H), 3.59–3.76 (m, 4H), 3.88–4.14 (m, 6H), 4.19 (m, 1H), 4.85 (s, 1H), 7.17 (s, 4H), 7.9 (s, 1H), 8.54 (s, 1H), 12.55 (s, 1H); Mass Spectrum: M+H$^+$ 508.

EXAMPLE 23

N-(6,7-dimethoxyquinazolin-4-yl)-N'-(2,6-dimethylphenyl)-N''-[2-(N-methylpyrrolidin-2-yl)ethyl]guanidine Using an analogous procedure to that described in Example 11. N-(7-hydroxy-6-methoxyquinazolin-4-yl)-N'-(2,6-dimethylphenyl)-N''-[2-(N-methylpyrrolidin-2-yl) ethyl]guanidine was reacted with trimethylsilyldiazomethane to give the title compound; NMR Spectrum: (DMSOd$_6$, 100° C.) 1.65 (m, 3H), 1.68 (m, 1H), 1.8–1.96 (m, 2H), 2.07 (q, 1H), 2.15 (s, 3H), 2.32 (s, 6H), 2.32 (s, 6H), 2.79 (br t, 1H), 2.59 (m, 1H), 2.69 (m, 1H), 3.84 (s, 3H), 3.95 (s, 3H), 7.08 (s, 1H), 7.20 (m, 4H), 7.74 (s, 1H), 8.47 (s, 1H), 10.9–11.3 (br s, 1H); Mass Spectrum: M+H$^+$ 463.

The N-(7-hydroxy-6-methoxyquinazolin-4-yl)-N'-(2,6-dimethylphenyl)-N''-[2-(N-methylpyrrolidin-2-yl)ethyl] guanidine starting material was prepared as follows:—

Using an analogous procedure to that described in Example 1, the 1-(7-benzyloxy-6-methoxyquinazolin-4-yl)-3-(2,6-dimethylphenyl)thiourea (0.8 g) was reacted with 2-(N-methylpyrrolidin-2-yl)ethylamine (0.78 ml). There was thus obtained N-(7-benzyloxy-6-methoxyquinazolin-4-yl)-N'-(2,6-dimethylphenyl)-N''-[2-(N-methylpyrrolidin-2-yl)ethyl]guanidine (0.6 g); NMR Spectrum: (DMSOd$_6$, 100° C.) 1.61 (m, 3H), 1.71 (m, 1H), 1.8–1.93 (m, 2H), 2.01 (q, 1H), 2.11 (s, 3H), 2.26 (m, 7H), 2.79 (br t, 1H), 3.54 (m, 1H), 3.65 (m, 1H), 3.84 (s, 3H), 5.30 (s, 2H), 7.20 (s, 4H), 7.35 (m, 1H), 7.41 (t, 2H), 7.51 (d, 2H), 7.7 (s, 1H), 8.42 (s, 1H), 10.8–11.3 (br s, 1H); Mass Spectrum: M+H$^+$ 539.

A portion (0.5 g) of this product was treated with trifluoroacetic acid (50 ml) using an analogous procedure to that described in Example 2 (Note[11]). There was thus obtained the required starting material; NMR Spectrum: (DMSOd$_6$, 100° C.) 1.58 (m, 3H), 1.66 (m, 1H), 1.76–1.9 (m, 2H), 2.0 (q, 1H), 2.09 (s, 3H), 2.24 (m, 7H), 2.74 (m, 1H), 3.50 (, 1H), 3.65 (m, 1H), 3.81 (s, 3H), 6.98 (s, 1H), 7.18 (s, 3H), 7.42 (br s, 1H), 7.67 (s, 1H), 8.38 (s, 1H), 9.5 (br s, 1H), 11.1 (br s, 1H); Mass Spectrum: M+H$^+$ 449.

EXAMPLE 24

N-(2,5-dimethylphenyl)-N'-(1,5-ethyleneoxyethylene)-N''-[6-methoxy-7-(N-methylpiperidin-4-ylmethoxy) quinazolin-4-yl]guanidine Using an analogous procedure to that described in Example 1,3-[6-methoxy-7-(N-methylpiperidin-4-yl-methoxy)quinazolin-4-yl]thiourea was reacted with morpholine to give the title compound in 94% yield; NMR Spectrum: (DMSOd$_6$, 100° C.) 1.4 (m, 2H), 1.8 (m, 3H), 1.95 (m, 2H), 2.2 (m, 6H), 2.3 (s, 3H), 2.84 (m, 2H), 3.5 (m, 4H), 3.65 (m, 4H), 3.9 (s, 3H), 4.0 (d, 2H), 6.8 (d, 1H), 6.98 (s, 1H), 6.98 (s, 1H), 7.05 (d, 1H), 7.12 (s, 1H), 7.7 (s, 1H), 8.48 (s, 1H), 11.45 (s, 1H), Mass Spectrum: M+H$^+$ 519.

EXAMPLE 25

N-(2-carbamoylethyl-N'-(2,6-dimethylphenyl)-N''-[6-methoxy-7-(3-morpholinopropoxy)quinazolin-4-yl]guanidine A mixture of N-(2-cyanoethyl)-N'-(2,6-dimethylphenyl-N''-[6-methoxy-7-(3-morpholinopropoxy)quinazolin-4-yl] guanidine (0.05 g) and concentrated sulphuric acid (0.5 ml) was stirred at ambient temperature for 4 hours. The reaction mixture was added dropwise to an ice cold saturated sodium bicarbonate solution and the resulting mixture was extracted with methylene chloride. The organic phase was dried and evaporated. There was thus obtained the title compound (0.025 g); NMR Spectrum: (CDCl$_3$) 2.13 (m, 2H), 2.31 (s, 6H), 2.5 (t, 4H), 2.59 (t, 2H), 2.7 (s, 2H), 3.72 (t, 4H), 3.89 (q, 2H), 4.01 (s, 3H), 4.26 (t, 2H), 4.86 (s, 1H), 5.3 (s, 1H), 6.28 (s, 1H), 7.19 (d, 4H), 7.87 (s, 1H), 8.59 (s, 1H), 12.54 (s, 1H); Mass Spectrum: M+H$^+$ 536.

EXAMPLE 26

N-(2-cyanoethyl-N'-(2,6-dimethylphenyl)-N''-[7-(2-morpholinoethoxy)quinazolin-4-yl]guanidine Using an analogous procedure to that described in Example 1, 3-[7-(2-morpholinoethoxy)quinazolin-4-yl]thiourea was reacted with 3-aminopropionitrile to give the title compound: NMR Spectrum: (CDCl$_3$) 2.27 (s, 6H), 2.55 (t, 4H), 2.86 (q, 4H), 3.69 (m, 6H), 4.21 (t, 2H), 4.63 (t, 1H), 7.08 (m, 1H), 7.16 (m, 4H), 8.3 (d, 1H), 8.59 (s, 1H), 12.5(s, 1H); Mass Spectrometry: M+H$^+$ 474.

The 3-[7-morpholinoethoxy)quinazoline-4-yl]thiourea used as a starting material was prepared as follows:—

4-Fluoroanthranilic acid (5 g) and formamidine acetate (6.71 g) in 2-methoxyethanol (40 ml) were heated to reflux for 16 hours. The solvent was evaporated and the residue was stirred with 0.02N aqueous ammonium hydroxide solution (100 ml). The resultant solid was filtered off, washed with water and dried. The solid was triturated under diethyl ether. There was thus obtained 7-fluoro- (4.88 g); NMR Spectrum: (DMSOd$_6$) 7.4 (m, 2H), 8.17 (m, 2H), 12.3 (s, 1H); Mass Spectrum: M+H$^+$ 165.

A mixture of N-(2-hydroxyethyl)morpholine (2.66 ml), sodium hydride (60% dispersion in mineral oil, 0.88 g) and DMF (25 ml) was warmed to 50° C. for 3 minutes. The resulting solution was allowed to cool for 10 minutes before a solution of 7-fluoro-3,4-dihydroquinazolin-4-one (1.64 g) in DMF (25 ml) was added and the resultant mixture was heated to 125° C. for 18 hours. The solvent was evaporated and the residue was partitioned between methylene chloride and 2N hydrochloric acid solution. The organic phase was dried and evaporated to give 7-(2-morpholinoethoxy)-3,4-dihydroquinazolin-4-one (1.58 g); NMR Spectrum: (CDCl$_3$)

2.6 (t, 4H), 2.87 (t, 2H), 3.73 (t, 4H), 4.25 (t, 2H), 7.12 (m, 2H), 8.07 (s, 1H), 8.19 (d, 1H); Mass Spectrum: M+H+ 276.

The material so obtained was reacted with thionyl chloride using an analogous procedure to that described in Example 1 which is concerned with the preparation of starting materials to give 4-chloro-7-(2-morpholinoethoxy) quinazoline (0.77 g); NMR Spectrum: (CDCl$_3$) 2.6 (t, 4H), 2.9 (t, 2H), 3.74 (t, 4H), 4.28 (t, 2H), 7.35 (m, 2H), 8.17 (d, 1H), 8.9 (s, 1H); Mass Spectrum: M+H+ 294.

A portion (0.67 g) of the material so obtained was reacted with ammonia using an analogous procedure to that described in the portion of Example 1 which is concerned with the preparation of starting material to give 4-amino-7-(2-morpholinoethoxy)quinazoline (0.67 g); Mass Spectrum: M+H+ 275.

A portion (0.2 g) of the material so obtained was reacted with 2,6-dimethylphenyl isothiocyanate using an analogous procedure to that described in the portion of Example 1 which is concerned with the preparation of starting materials to give 1-(2,6-dimethylphenyl)-3-[7-(2-morpholinoethoxy) quinazolin-4-yl]thiourea (0.14 g); NMR Spectrum: (CDCl$_3$) 2.37 (s, 6H), 2.61 (t, 4H), 2.92 (t, 2H), 3.75 (t, 4H), 4.3 (t, 2H), 7.20 (m, 3H), 7.35 (m, 2H), 7.89 (d, 1H), 8.77 (s, 1H), 8.91 (s, 1H); Mass Spectrum: M+H+ 438.

The invention claimed is:

1. A quinazoline derivative of the Formula I

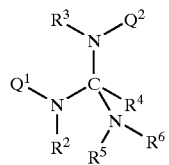

I wherein Q$^1$ is a quinazoline ring of the formula Ia

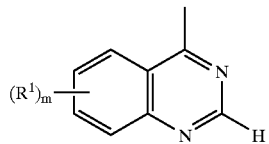

Ia wherein:

m is 0, 1, 2, 3 or 4;

each R$^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

Q$^3$—X$^1$— wherein X$^1$ is a direct bond or is selected from O, S, SO, SO$_2$, N(R$^7$), CO, CH(OR$^7$), CON(R$^7$), N(R$^7$)CO, SO$_2$N(R$^7$), N(R$^7$)SO$_2$, OC(R$^7$)$_2$, SC(R$^7$)$_2$ and N(R$^7$)C(R$^7$)$_2$, wherein R$^7$ is hydrogen or (1-6C)alkyl, and Q$^3$ is aryl, aryl-(1-6C)alkyl, (3-7C)cycloalkyl, (3-7C)cycloalkyl-(1-6C)alkyl, (3-7C) cycloalkenyl, (3-7C)cycloalkenyl-(1-6C) alkyl, heteroaryl, heteroaryl-(1-6C)alkyl, heterocyclyl or heterocyclyl-(1-6C)alkyl, or (R$^1$)$_m$ is (1-3C)alkylenedioxy, and wherein adjacent carbon atoms in any (2-6C)alkylene chain within a R$^1$ substituent are optionally separated by the insertion into the chain of a group selected from O, S, SO, SO$_2$, N(R$^8$), CO, CH(OR$^8$), CON(R$^8$), N(R$^8$)CO, SO$_2$N(R$^8$), N(R$^8$)SO$_2$, CH=CH and C≡C wherein R$^8$ is hydrogen or (1-6C)alkyl, and wherein any CH$_2$=CH— or HC≡C— group within a R$^1$ substituent optionally bears at the terminal CH$_2$= or HC≡ position a substituent selected from halogeno, carboxy, carbamoyl, (1-6C)alkoxycarbonyl, N-(1-6C) alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

Q$^4$—X$^2$— wherein X$^2$ is a direct bond or is selected from CO and N(R$^9$)CO, wherein R$^9$ is hydrogen or (1-6C)alkyl, and Q$^4$ is aryl, aryl-(1-6C)alkyl, heteroaryl, heteroaryl-(1-6C)alkyl, heterocyclyl or heterocyclyl-(1-6C)alkyl, and wherein any CH$_2$ or CH$_3$, group within a R$^1$ substituent optionally bears on each said CH$_2$ or CH$_3$ group one or more halogeno substituents or a substituent selected from hydroxy, cyano, amino, carboxy, carbamoyl, (1-6C)alkyl, (1-6C)alkoxy, (1-6C)alkylthio, (1-6C) alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C) alkyl-(1-6C)alkanesulphonylamino, or from a group of the formula:

—X$^3$—Q$^5$ wherein X$^3$ is a direct bond or is selected from O, S, SO, SO$_2$, N(R$^{10}$), CO, CH(OR$^{10}$), CON(R$^{10}$), N(R$^{10}$)CO, SO$_2$N(R$^{10}$), N(R$^{10}$)SO$_2$, C(R$^{10}$)$_2$O, C(R$^{10}$)$_2$S and N(R$^{10}$)C(R$^{10}$)$_2$, wherein R$^{10}$ is hydrogen or (1-6C)alkyl, and Q$^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C) alkyl, heteroaryl, heteroaryl-(1-6C)alkyl, heterocyclyl or heterocyclyl-(1-6C)alkyl, and wherein any aryl, heteroaryl or heterocyclyl group within a substituent on R$^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C) alkenyloxy, (2-6C)alkynyloxy, (1-6C)alkylthio, (1-6C) alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^4-R^{11}$$

wherein $X^4$ is a direct bond or is selected from O and $N(R^{12})$, wherein $R^{12}$ is hydrogen or (1-6C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoylalkyl, N-(1-6C)alkylcarbamoyl-(1-6C)alkyl or N,N-di-[(1-6C)alkyl]carbamoyl-(1-6C)alkyl, or from a group of the formula:

$$-X^5-Q^6$$

wherein $X^5$ is a direct bond or is selected from O and $N(R^{13})$, wherein $R^{13}$ is hydrogen or (1-6C)alkyl, and $Q^6$ is aryl, aryl-(1-6C)alkyl, heteroaryl, heteroaryl-(1-6C)alkyl, heterocyclyl or heterocyclyl-(1-6C)alkyl, and any $Q^6$ group optionally bears 1 or 2 substituents, which may be the same or different, selected from halogeno, (1-6C)alkyl and (1-6C)alkoxy, and wherein any heterocyclyl group within a substituent or $R^1$ optionally bears 1 or 2 oxo or thioxo substituents;

$R^2$ is hydrogen or (1-6C)alkyl and $R^3$ is hydrogen or (1-6C)alkyl, or $R^2$ and $R^3$ together form a $CH_2$, $(CH_2)_2$ or $(CH_2)_3$ group, $R^5$ is hydrogen or (1-6C)alkyl, $R^5$ and $R^6$ together with the N atom to which they are attached from a 4- to 7-membered heterocyclic ring optionally containing a further heteroatom selected from O, N and S, provided that one of the pairs of groups $R^2$ and $R^4$ together, $R^3$ and $R^4$ together and $R^5$ and $R^4$ together forms a bond;

$Q^2$ is aryl, aryl-(1-3C)alkyl, aryl-(3-7C)cycloalkyl, heteroaryl, heteroaryl-(1-3C)alkyl or heteroaryl-(3-7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituted with 1, 2, 3 or 4 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^6-R^{14}$$

wherein $X^6$ is a direct bond or is selected from O and $N(R^{15})$, wherein $R^{15}$ is hydrogen or (1-6C)alkyl, and $R^{14}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

$$-X^7-Q^7$$

wherein $X^7$ is a direct bond or is selected from O, S, SO, $SO_2$, $N(R^{16})$, CO, $CH(OR^{16})$, $CON(R^{16})$, $N(R^{16})CO$, $SO_2N(R^{16})$, $N(R^{16})SO_2$, $C(R^{16})_2O$, $C(R^{16})_2S$ and $C(R^{16})_2N(R^{16})$, wherein each $R^{16}$ is hydrogen or (1-6C)alkyl, and $Q^7$ is aryl, aryl-(1-6C)alkyl, heteroaryl, heteroaryl-(1-6C)alkyl, heterocyclyl or heterocyclyl-(1-6C)alkyl, or $Q^2$ is optionally substituted with a (1-3C)alkylenedioxy group, and wherein any aryl, heteroaryl or heterocyclyl group within a substituent on $Q^2$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^8-R^{17}$$

wherein $X^8$ is a direct bond or is selected from O and $N(R^{18})$, wherein $R^{18}$ is hydrogen or (1-6C)alkyl, and $R^{17}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within a substituent on $Q^2$ optionally bears 1 or 2 oxo or thioxo substituents; and $R^6$ is an optionally substituted group selected from (2-6C)alkenyl, (2-6C)alkynyl, (3-7C)cycloalkyl and (3-7C)cycloalkenyl, or $R^6$ is a substituted (1-6C)alkyl group, and wherein adjacent carbon atoms in any (2-6C)alkylene chain within a $R^6$ group are optionally separated by the insertion into the chain of a group selected from O, S, SO, $SO_2$, $N(R^{19})$, CO, $CH(OR^{19})$, $CON(R^{19})$, $N(R^{19})CO$, $SO_2N(R^{19})$, $N(R^{19})SO_2$, CH=CH and C≡C wherein $R^{19}$ is hydrogen or (1-6C)alkyl, and wherein any $CH_2$=CH— or HC≡C group within a $R^6$ group optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^8-X^9-$$

wherein $X^9$ is a direct bond or is selected from CO and $N(R^{20})$, CO, wherein $R^{20}$ is hydrogen or (1-6C)alkyl, and $Q^8$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^6$ group optionally bears on each said $CH_2$ or $CH_3$ group one or more of the following substituents, provided that the $R^6$ group when it is (1-6C)alkyl must bear at least one such substituent, one or more halogeno substituents or a substituent selected from hydroxy, cyano, amidino, amino, carboxy, carbamoyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)

alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, (1-6C)alkoxycarbonylamino, N-(1-6C)alkyl-(1-6C)alkoxycarbonylamino, N-[hydroxy-(2-6C)alkyl]carbamoyl, N-[(1-6C)alkoxy-(2-6C)alkyl]carbamoyl, N-[amino-(2-6C)alkyl]carbamoyl, N-[(1-6C)alkylamino-(2-6C)alkyl]carbamoyl, N-{di-[(1-6C)alkyl]amino-(2-6C)alkyl}carbamoyl, N,N-di-[hydroxy-(2-6C)alkyl]carbamoyl, N,N-di-[(1-6C)alkoxy-(2-6)alkyl]carbamoyl, N,N-[amino-(2-6C)alkyl]carbamoyl, N,N-di-[(1-6C)alkylamino-(2-6C)alkyl]carbamoyl and N,N-di-{di-[(1-6C)alkyl]amino-(2-6C)alkyl}carbamoyl, or from a group of the formula:

$$-X^{10}-Q^9$$

wherein $X^{10}$ is a direct bond or is selected from O, S, SO, $SO_2$, $N(R^{21})$, CO, $CH(OR^{21})$, $CON(R^{21})$, $N(R^{21})CO$, $SO_2N(R^{21})$, $N(R^{21})SO_2$, $C(R^{21})_2O$, $C(R^{21})_2S$ and $N(R^{21})C(R^{21})_2$, wherein $R^{21}$ is hydrogen or (1-6C)alkyl, and $Q^9$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a $R^6$ group, or any heterocyclic group formed when $R^5$ and $R^6$ together with the N atom to which they are attached form a ring, optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^{11}-R^{22}$$

wherein $X^{11}$ is a direct bond or is selected from O and $N(R^{23})$, wherein $R^{23}$ is hydrogen or (1-6C)alkyl, and $R^{22}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl, or from a group of the formula:

$$-X^{12}-Q^{10}$$

wherein $X^{12}$ is a direct bond or is selected from O and $N(R^{24})$, wherein $R^{24}$ is hydrogen or (1-6C)alkyl, and $Q^{10}$ is aryl, aryl-(1-6C)alkyl, heteroaryl, heteroaryl-(1-6C)alkyl, heterocyclyl or heterocyclyl-(1-6C)alkyl, and any $Q^{10}$ group optionally bears 1 or 2 substituents, which may be the same or different, selected from halogeno, (1-6C)alkyl and (1-6C)alkoxy, and wherein any heterocyclyl group within a $R^6$ group, or the heterocyclic group formed when $R^5$ and $R^6$ together with the N atom to which they are attached form a ring, optionally bears 1 or 2 oxo or thioxo substituents;

or a tautomer thereof or a pharmaceutically-acceptable salt thereof.

2. A quinazoline derivative of the Formula I according to claim 1 wherein:

m is 1 and the $R^1$ group is located at the 6- or 7-position and is selected from methoxy, benzyloxy, cyclopropylmethoxy, 2-dimethylaminoethoxy, 2-diethylaminoethoxy, 3-dimethylaminopropoxy, 3-diethylaminopropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-propoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 2-(2-oxoimidazolidin-1-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1yl)propoxy, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 2-methylsulphonylethoxy, 3-methylsulphonylpropoxy, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(pyrrolidin-1yl)-1-hexynyl, 6-(piperidino)-1-hexynyl, 6-(morpholino)-1-hexynyl, 6-(4-methylpiperazin-1-yl)-1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, or m is 2 and the $R^1$ groups are located at the 6- and 7-positions, one $R^1$ group is located at the 6- or 7-position and is selected from the groups defined immediately hereinbefore and the other $R^1$ group is a methoxy group;

each of $R^2$, $R^3$ and $R^5$ is hydrogen except that one of the pairs of the groups $R^2$ and $R^4$ together, $R^3$ and $R^4$ together and $R^5$ and $R^4$ together forms a bond;

$Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is an optionally substituted group selected from allyl, 2-propynyl, cyclopropyl, cyclobutyl, cyclopentyl and cyclohexyl, or $R^6$ is a substituted methyl, ethyl, propyl or butyl group, and wherein adjacent atoms in any (2-6C)alkylene chain within a $R^6$ group are optionally separated by the insertion into the chain of a group selected from O, NH, CH=CH and C≡C, and wherein any $CH_2$ or $CH_3$ group within a $R^6$ group optionally bears on each said $CH_2$ or $CH_3$ group one or more of the following substituents, provided that the $R^6$ group when it is a methyl, ethyl, propyl or butyl group must bear at least one such substituent, one, two, or three fluoro substituents or a substituent selected from hydroxy, cyano, amidino, amino, carboxy, methoxy, methylthio, methylsulphinyl, methylsulphonyl, methylamino, dimethylamino, methoxycarbonyl, ethoxycarbonyl, propoxycarbonyl, tert-butoxycarbonyl, acetamido, phenyl, cyclopropyl, cyclobutyl, cyclopentyl, cyclohexyl, 1-imidazolyl, 2-imidazolyl, 4-imidazolyl, 2-pyridyl, 3-pyridyl, 4-pyridyl, tetrahydrofuran-2-yl, pyrrolidin-1-yl, 1,4-dioxan-2-yl, morpholino, piperidino, piperazin-1-yl, homopiperidin-1-yl and homopiperazin-1-yl, and wherein any phenol, imidazolyl, pyridyl or heterocyclyl group within a $R^6$ group optionally bears 1 or 2 substituents, which may be the same or different, selected from fluoro, chloro, trifluoromethyl, hydroxy, amino, carbamoyl, methyl, ethyl and methoxy, and wherein any heterocyclyl group within a $R^6$ group optionally bears 1 or 2 oxo substituents, or a pharmaceutically-acceptable acid-addition salt thereof.

3. A quinazoline derivative of the Formula I according to claim 1 wherein:— m is 1 and the $R^1$ group is located at the 6- or 7-position and is selected from 2-(2-methoxyethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, N-methylpyrrolidin-3-yloxy, 2-pyrrolidin-1-ylethoxy, 3-pyrrolidin-1-ylpropoxy, 3-morpholinylmethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, N-(2-methoxyethyl)piperidin-4-ylmethoxy, 2-(4-methylpiperazin-1-yl)ethoxy, 3-(4-methylpiperazin-1-yl)propoxy, benzyloxy, cyclopropylmethoxy, 3-methylsulphonylpropoxy and 2-[N-(2-methoxyethyl)-N-methylamino]ethoxy;

or m is 2 and one $R^1$ group is located at the 7-position and is selected from the groups defined immediately hereinbefore and the other $R^1$ group is a 6-methoxy group;

or m is 2 and one $R^1$ group is located at the 6-position and is selected from the groups defined immediately hereinbefore and the other $R^1$ group is a 7-methoxy group;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl which bears 1, 2 or 3 substituents, which may be the same or different, selected from fluoro, chloro, bromo, trifluoromethyl, nitro, methyl, ethyl and methoxy provided that at least one substituent is located at an ortho position; and $R^6$ is allyl, 2-propynyl, cyclopropyl, cyclopropylmethyl, cyclobutyl, cyclopentyl or 4-hydroxycyclohexyl, or $R^6$ is a substituted methyl, ethyl, propyl or butyl group, and wherein adjacent carbon atoms in any propyl or butyl group are optionally separated by the insertion into the chain of an O group, and wherein any $CH_2$ or $CH_3$ group within a $R^6$ group when it is a methyl, ethyl, propyl or butyl group bears one, two or three fluoro substituents or a substituent selected from hydroxy, cyano, amidino, amino, carboxy, methoxy, ethoxy, methylthio, methylsulphinyl, methylsulphonyl, methylamino, ethylamino, isopropylamino, dimethylamino, methoxycarbonyl, ethoxycarbonyl, propoxycarbonyl, tert-butoxycarbonyl, N-methylcarbamoyl, N-ethylcarbamoyl, N-isopropylcarbamoyl, N-tert-butylcarbamoyl, acetamido, phenyl, cyclopropyl, 2-furyl, 2-thienyl, 4-imidazolyl, 2-pyridyl, 3-pyridyl, 4-pyridyl, tetrahydrofuran-2-yl, pyrrolidin-1-yl, pyrrolidin-2-yl, 2-oxopyrrolidin-1-yl, 1,4-dioxan-2-yl, morpholino, piperidino, piperidin-2-yl and piperazin-1-yl, and wherein any phenyl, heteroaryl or heterocyclyl group within a $R^6$ group optionally bears 1 or 2 substituents, which may be the same or different, selected from fluoro, chloro, trifluoromethyl, hydroxy, methyl ethyl and methoxy;

or a pharmaceutically-acceptable acid-addition salt thereof.

4. A quinazoline derivative of the Formula I according to claim 1 wherein:— m is 2 and one $R^1$ group is a 6-methoxy group and the other $R^1$ group is located at the 7-position and is selected from 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-piperidinoethoxy, 3-piperidinopropoxy, N-methylpiperidin-4-ylmethoxy, N-(2-methoxyethyl)piperidin-4-ylmethoxy, 2-(4-methylpiperazin-1-yl)ethoxy and 3-(4-methylpiperazin-1-yl)propoxy;

each of $R^2$, $R^3$ and $R^5$ is hydrogen except that one of the pairs of groups $R^2$ and $R^4$ together, $R^3$ and $R^4$ together and $R^5$ and $R^4$ together forms a bond;

$Q^2$ is phenyl which bears 1, 2 or 3 substituents, which may be the same or different, selected from fluoro, chloro, bromo and methyl provided that at least one substituent is located at an ortho position; and $R^6$ is allyl, 2-propynyl, cyclopropyl, cyclopropylmethyl, cyclobutyl, 4-hydroxycyclohexyl, 2,2,2-trifluoromethyl, 2,3-dihydroxypropyl, 2-aminoethyl, 3-aminopropyl, 2-methylaminoethyl, 3-methylaminopropyl, 2-dimethylaminoethyl, 3-dimethylaminopropyl, 2-hydroxyethyl, 3-hydroxypropyl, 2-methoxyethyl, 3-methoxypropyl, 2-methylthioethyl, 3-methylthiopropyl, 2-methylsulphonylethyl, 3-methylsulphonylpropyl, 2-(2-hydroxyethoxy)ethyl, 2-cyanoethyl, 5-cyanopentyl, 2-amidinoethyl, carboxymethyl, 2-carboxyethyl, methoxycarbonylmethyl, 2-methoxycarbonylethyl, tert-butoxycarbonylmethyl, 2-(tert-butoxycarbonyl)ethyl, N-methylcarbamoylmethyl, N-isopropylcarbamoylmethyl, N-tert-butylcarbamoylmethyl, benzyl, 2-fluorobenzyl, 3-fluorobenzyl, 2,6-difluorobenzyl, phenethyl, 2-furylmethyl, 2-thienylmethyl, 2-imidazol-4-ylethyl, 2-pyridylmethyl, 3-pyridylmethyl, 4-pyridylmethyl, 2-pyrid-2-ylethyl, tetrahydrofuran-2-ylmethyl, 1,4-dioxan-2-ylmethyl, 2-pyrrolidin-1-ylethyl, 2-(2-oxopyrrolidin-1-yl)ethyl, 2-(N-methylpyrrolidin-2-yl)ethyl, 3-pyrrolidin-1-ylpropyl, 3-(2-oxopyrrolidin-1-yl)propyl, 2-morpholinoethyl, 3-morpholinopropyl, 2-piperdinoethyl, 3-piperidinopropyl, 2-(4-methylpiperazin-1-yl)ethyl, 3-(4-methylpiperazin-1-yl)propyl, N-methylpiperidin-3-ylmethyl or N-methylpiperidin-4-ylmethyl;

or a pharmaceutically-acceptable acid-addition salt thereof.

5. A quinazoline derivative of the Formula I according to claim 1 selected from:—

N-(2-chloro-6-methylphenyl)-N'-(2-hydroxyethyl)-N"-[6-methoxy-7-(N-methylpiperidin-4-ylmethoxy)quinazolin-4-yl]guanidine, N-allyl-N'-(2-chloro-6-methylphenyl)-N"-[6-methoxy-7-(3-pyrrolidin-1-ylpropoxy)quinazolin-4-yl]guanidine, N-allyl-N'-(2,6-dimethylphenyl)-N"-[6-methoxy-7-(N-methylpiperidin-4-ylmethoxy)quinazolin-4-yl]guanidine, and N-(2-chloro-6-methylphenyl)-N'-[6-methoxy-7-(N-methylpiperidin-4-ylmethoxy)quinazolin-4-yl]-N"-(2-propynyl)guanidine;

or a pharmaceutically-acceptable acid-addition salt thereof.

6. A process for the preparation of a quinazoline derivative of the Formula I, or a pharmaceutically-acceptable salt thereof, according to claim 1 which comprises:—

(a) the reaction of a thiourea of the Formula VI

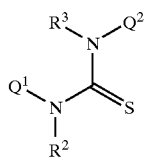

VI wherein $Q^1$, $R^2$, $Q^2$ and $R^3$ have any of the meanings defined in claim 1 except that any functional group is protected if necessary, with an amine of the Formula VII

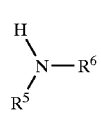

VII wherein $R^5$ and $R^6$ have any of the meanings defined in claim 1 except that any functional group is protected if necessary, whereafter any protecting group that is present is removed by conventional means;

(b) for the production of those compounds of the Formula I wherein $Q^1$, $R^6$ or $Q^2$ contains a carboxy group, the cleavage of the corresponding compound of Formula I wherein $Q^1$, $R^6$ and $Q^2$ contains a protected carboxy group;

(c) for those compounds of the Formula I wherein $R^6$ or a substituent on $Q^1$ or $Q^2$ contains an alkylcarbamoyl groups or a substituted alkylcarbamoyl group, the reaction of the corresponding compound of Formula I wherein $R^6$ or a substituent on $Q^1$ or $Q^2$ is a carboxy group, or a reactive derivative thereof, with an amine or substituted amine as appropriate;

(d) for those compounds of the Formula I wherein a substituent on $Q^1$ or $Q^2$ contains an amino-(1-6C)alkyl group or $R^6$ an amino-(1-6C)alkyl group, the cleavage of the corresponding compound of Formula I wherein a substituent on $Q^1$ or $Q^2$ is a protected amino-(1-6C)alkyl group or $R^6$ is a protected amino-(1-6C)alkyl group as appropriate;

(e) for those compounds of the Formula I wherein a substituent on $Q^1$ or $Q^2$ contains an amino group, the reduction of a corresponding compound of Formula I wherein a substituent on $Q^1$ or $Q^2$ contains a nitro group; or (f) for the production of those compounds of the Formula I wherein $Q^1$ contains a $R^1$ group in a quinazoline-like ring of the formula Ia that is linked via an oxygen atom, the alkylation of the corresponding compound of Formula I wherein the $R^1$ group in $Q^1$ is a hydroxy group;

and optionally forming a pharmaceutically-acceptable salt thereof.

7. A pharmaceutical composition which comprises a quinazoline derivative of the Formula I, or a pharmaceutically-acceptable salt thereof, according to claim 1 in association with a pharmaceutically-acceptable diluent or carrier.

8. A method for the treatment of rheumatoid arthritis in a warm-blooded animal in need thereof, which comprises administering to said animal an effective amount of a quniazoline derivative of the Formula I, according to claim 1 or a pharmaceutically-acceptable salt thereof.

9. A method for the treatment of transplant rejection in a warm-blooded animal in need thereof, which comprises administering to said animal an effective amount of a quinazoline derivative of the Formula I, according to claim 1 or a pharmaceutically-acceptable salt thereof.

* * * * *